United States Patent
Goode, Jr. et al.

(10) Patent No.: US 8,491,474 B2
(45) Date of Patent: *Jul. 23, 2013

(54) SYSTEMS AND METHODS FOR REPLACING SIGNAL ARTIFACTS IN A GLUCOSE SENSOR DATA STREAM

(75) Inventors: Paul V. Goode, Jr., Cherry Hill, NJ (US); James H. Brauker, Addison, MI (US); Apurv U. Kamath, San Diego, CA (US); James Patrick Thrower, Oakland, NJ (US); Victoria Carr-Brendel, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 152 days.

This patent is subject to a terminal disclaimer.

(21) Appl. No.: 13/015,208

(22) Filed: Jan. 27, 2011

(65) Prior Publication Data

US 2011/0118579 A1    May 19, 2011

Related U.S. Application Data

(62) Division of application No. 12/353,799, filed on Jan. 14, 2009, now Pat. No. 7,935,057, which is a division of application No. 10/648,849, filed on Aug. 22, 2003, now Pat. No. 8,010,174.

(51) Int. Cl.
  *A61B 5/00* (2006.01)
  *A61B 5/05* (2006.01)
(52) U.S. Cl.
  USPC .............. 600/365; 600/345; 600/347
(58) Field of Classification Search
  USPC .......................... 600/345, 347, 365
  See application file for complete search history.

(56) References Cited

U.S. PATENT DOCUMENTS

| | | | |
|---|---|---|---|
| 3,210,578 | A | 10/1965 | Sherer |
| 3,219,533 | A | 11/1965 | Mullins |

(Continued)

FOREIGN PATENT DOCUMENTS

| | | |
|---|---|---|
| CA | 2127172 | 7/1998 |
| EP | 0 098 592 | 1/1984 |

(Continued)

OTHER PUBLICATIONS

Moussy et al. 1993. Performance of subcutaneously implanted needle-type glucose sensors employing a novel trilayer coating, Anal Chem. 85: 2072-2077.

(Continued)

*Primary Examiner* — Patricia Mallari
*Assistant Examiner* — Christian Jang
(74) *Attorney, Agent, or Firm* — Knobbe Martens Olson & Bear LLP

(57) ABSTRACT

Systems and methods for minimizing or eliminating transient non-glucose related signal noise due to non-glucose rate limiting phenomenon such as ischemia, pH changes, temperatures changes, and the like. The system monitors a data stream from a glucose sensor and detects signal artifacts that have higher amplitude than electronic or diffusion-related system noise. The system replaces some or the entire data stream continually or intermittently including signal estimation methods that particularly address transient signal artifacts. The system is also capable of detecting the severity of the signal artifacts and selectively applying one or more signal estimation algorithm factors responsive to the severity of the signal artifacts, which includes selectively applying distinct sets of parameters to a signal estimation algorithm or selectively applying distinct signal estimation algorithms.

16 Claims, 20 Drawing Sheets

U.S. PATENT DOCUMENTS

| | | | |
|---|---|---|---|
| 3,775,182 A | 11/1973 | Patton et al. | |
| 3,780,727 A | 12/1973 | King | |
| 3,898,984 A | 8/1975 | Mandel et al. | |
| 3,929,971 A | 12/1975 | Roy | |
| 3,943,918 A | 3/1976 | Lewis | |
| 3,964,974 A | 6/1976 | Banauch et al. | |
| 3,979,274 A | 9/1976 | Newman | |
| 4,024,312 A | 5/1977 | Korpman | |
| 4,076,656 A | 2/1978 | White et al. | |
| 4,197,840 A | 4/1980 | Beck et al. | |
| 4,215,703 A | 8/1980 | Willson | |
| 4,240,889 A | 12/1980 | Yoda et al. | |
| 4,253,469 A | 3/1981 | Aslan | |
| 4,255,500 A | 3/1981 | Hooke | |
| 4,259,540 A | 3/1981 | Sabia | |
| 4,374,013 A | 2/1983 | Enfors | |
| 4,403,984 A | 9/1983 | Ash et al. | |
| 4,415,666 A | 11/1983 | D'Orazio et al. | |
| 4,431,004 A | 2/1984 | Bessman et al. | |
| 4,436,094 A | 3/1984 | Cerami | |
| 4,454,295 A | 6/1984 | Wittmann et al. | |
| 4,494,950 A | 1/1985 | Fischell | |
| 4,506,680 A | 3/1985 | Stokes | |
| RE31,916 E | 6/1985 | Oswin et al. | |
| 4,554,927 A | 11/1985 | Fussell | |
| 4,577,642 A | 3/1986 | Stokes | |
| RE32,361 E | 2/1987 | Duggan | |
| 4,655,880 A | 4/1987 | Liu | |
| 4,663,824 A | 5/1987 | Kenmochi | |
| 4,671,288 A | 6/1987 | Gough | |
| 4,680,268 A | 7/1987 | Clark, Jr. | |
| 4,703,756 A | 11/1987 | Gough et al. | |
| 4,711,251 A | 12/1987 | Stokes | |
| 4,721,677 A | 1/1988 | Clark | |
| 4,731,726 A | 3/1988 | Allen | |
| 4,757,022 A | 7/1988 | Shults et al. | |
| 4,759,828 A | 7/1988 | Young et al. | |
| 4,781,798 A | 11/1988 | Gough | |
| 4,805,625 A | 2/1989 | Wyler | |
| 4,849,458 A | 7/1989 | Reed et al. | |
| 4,852,573 A | 8/1989 | Kennedy | |
| 4,858,615 A | 8/1989 | Meinema | |
| 4,863,265 A | 9/1989 | Flower et al. | |
| 4,871,440 A | 10/1989 | Nagata et al. | |
| 4,883,057 A | 11/1989 | Broderick | |
| 4,890,620 A | 1/1990 | Gough | |
| 4,890,621 A | 1/1990 | Hakky | |
| 4,907,857 A | 3/1990 | Giuliani et al. | |
| 4,919,141 A | 4/1990 | Zier et al. | |
| 4,927,407 A | 5/1990 | Dorman | |
| 4,927,516 A | 5/1990 | Yamaguchi et al. | |
| 4,944,299 A | 7/1990 | Silvian | |
| 4,953,552 A | 9/1990 | DeMarzo | |
| 4,975,636 A | 12/1990 | Desautels | |
| 4,986,671 A | 1/1991 | Sun et al. | |
| 4,988,341 A | 1/1991 | Columbus et al. | |
| 4,994,167 A | 2/1991 | Shults et al. | |
| 5,002,572 A | 3/1991 | Picha | |
| 5,030,333 A | 7/1991 | Clark, Jr. | |
| 5,050,612 A | 9/1991 | Matsumura | |
| 5,067,491 A | 11/1991 | Taylor, II et al. | |
| 5,068,536 A | 11/1991 | Rosenthal | |
| 5,077,476 A | 12/1991 | Rosenthal | |
| 5,097,834 A | 3/1992 | Skrabal | |
| 5,101,814 A | 4/1992 | Palti | |
| 5,108,819 A | 4/1992 | Heller et al. | |
| 5,137,028 A | 8/1992 | Nishimura | |
| 5,140,985 A | 8/1992 | Schroeder et al. | |
| 5,160,418 A | 11/1992 | Mullen | |
| 5,165,407 A | 11/1992 | Wilson et al. | |
| 5,171,689 A | 12/1992 | Kawaguri et al. | |
| 5,190,041 A | 3/1993 | Palti | |
| 5,198,771 A | 3/1993 | Fidler et al. | |
| 5,208,147 A | 5/1993 | Kagenow et al. | |
| 5,216,598 A | 6/1993 | Branstetter et al. | |
| 5,243,983 A | 9/1993 | Tarr et al. | |
| 5,264,104 A | 11/1993 | Gregg et al. | |
| 5,266,179 A | 11/1993 | Nankai et al. | |
| 5,269,891 A | 12/1993 | Colin | |
| 5,282,848 A | 2/1994 | Schmitt | |
| 5,285,513 A | 2/1994 | Kaufman et al. | |
| 5,287,753 A | 2/1994 | Routh et al. | |
| 5,299,571 A | 4/1994 | Mastrototaro | |
| 5,304,468 A | 4/1994 | Phillips et al. | |
| 5,307,263 A | 4/1994 | Brown | |
| 5,310,469 A | 5/1994 | Cunningham et al. | |
| 5,312,361 A | 5/1994 | Zadini et al. | |
| 5,316,008 A | 5/1994 | Suga et al. | |
| 5,324,322 A | 6/1994 | Grill et al. | |
| 5,330,521 A | 7/1994 | Cohen | |
| 5,330,634 A | 7/1994 | Wong et al. | |
| 5,331,555 A | 7/1994 | Hashimoto et al. | |
| 5,337,747 A | 8/1994 | Neftel | |
| 5,342,409 A | 8/1994 | Mullett | |
| 5,343,869 A | 9/1994 | Pross et al. | |
| 5,368,224 A | 11/1994 | Richardson et al. | |
| 5,372,133 A | 12/1994 | Hogen Esch | |
| 5,376,070 A | 12/1994 | Purvis et al. | |
| 5,384,028 A | 1/1995 | Ito | |
| 5,390,671 A | 2/1995 | Lord et al. | |
| 5,391,250 A | 2/1995 | Cheney, II et al. | |
| 5,398,682 A | 3/1995 | Lynn | |
| 5,411,647 A | 5/1995 | Johnson et al. | |
| 5,411,866 A | 5/1995 | Luong | |
| 5,429,735 A | 7/1995 | Johnson et al. | |
| 5,431,160 A | 7/1995 | Wilkins | |
| 5,434,412 A | 7/1995 | Sodickson et al. | |
| 5,448,992 A | 9/1995 | Kupershmidt | |
| 5,462,051 A | 10/1995 | Oka et al. | |
| 5,462,064 A | 10/1995 | D'Angelo et al. | |
| 5,469,846 A | 11/1995 | Khan | |
| 5,474,552 A | 12/1995 | Palti | |
| 5,484,404 A | 1/1996 | Schulman et al. | |
| 5,491,474 A | 2/1996 | Suni et al. | |
| 5,494,562 A | 2/1996 | Maley et al. | |
| 5,496,453 A | 3/1996 | Uenoyama et al. | |
| 5,497,772 A | 3/1996 | Schulman et al. | |
| 5,502,396 A | 3/1996 | Desarzens et al. | |
| 5,507,288 A | 4/1996 | Bocker et al. | |
| 5,508,203 A | 4/1996 | Fuller et al. | |
| 5,513,636 A | 5/1996 | Palti | |
| 5,518,601 A | 5/1996 | Foos et al. | |
| 5,531,878 A | 7/1996 | Vadgama et al. | |
| 5,540,828 A | 7/1996 | Yacynych | |
| 5,553,616 A | 9/1996 | Ham et al. | |
| 5,568,806 A | 10/1996 | Cheney, II et al. | |
| 5,569,186 A | 10/1996 | Lord et al. | |
| 5,571,395 A | 11/1996 | Park et al. | |
| 5,575,930 A | 11/1996 | Tietje-Girault et al. | |
| 5,582,184 A | 12/1996 | Ericson et al. | |
| 5,584,813 A | 12/1996 | Livingston et al. | |
| 5,584,876 A | 12/1996 | Bruchman et al. | |
| 5,586,553 A | 12/1996 | Halili et al. | |
| 5,590,651 A | 1/1997 | Shaffer et al. | |
| 5,624,537 A | 4/1997 | Turner et al. | |
| 5,640,470 A | 6/1997 | Iyer et al. | |
| 5,653,863 A | 8/1997 | Genshaw et al. | |
| 5,660,163 A | 8/1997 | Schulman et al. | |
| 5,683,562 A | 11/1997 | Schaffar et al. | |
| 5,686,829 A | 11/1997 | Girault | |
| 5,695,623 A | 12/1997 | Michel et al. | |
| 5,711,861 A | 1/1998 | Ward et al. | |
| 5,730,654 A | 3/1998 | Brown | |
| 5,743,262 A | 4/1998 | Lepper, Jr. et al. | |
| 5,749,907 A | 5/1998 | Mann | |
| 5,755,226 A | 5/1998 | Carim et al. | |
| 5,779,665 A | 7/1998 | Mastrototaro et al. | |
| 5,781,455 A | 7/1998 | Hyodo et al. | |
| 5,787,900 A | 8/1998 | Butler et al. | |
| 5,791,344 A | 8/1998 | Schulman et al. | |
| 5,795,774 A | 8/1998 | Matsumoto et al. | |
| 5,800,420 A | 9/1998 | Gross | |
| 5,806,517 A | 9/1998 | Gerhardt et al. | |

| Patent | Type | Date | Inventor |
|---|---|---|---|
| 5,807,375 | A | 9/1998 | Gross et al. |
| 5,814,599 | A | 9/1998 | Mitragotri et al. |
| 5,822,715 | A | 10/1998 | Worthington et al. |
| 5,833,603 | A | 11/1998 | Kovacs et al. |
| 5,836,887 | A | 11/1998 | Oka et al. |
| 5,836,989 | A | 11/1998 | Shelton |
| 5,837,728 | A | 11/1998 | Purcell |
| 5,851,197 | A | 12/1998 | Marano et al. |
| 5,861,019 | A | 1/1999 | Sun et al. |
| 5,871,514 | A | 2/1999 | Wiklund et al. |
| 5,882,494 | A | 3/1999 | Van Antwerp |
| 5,897,578 | A | 4/1999 | Wiklund et al. |
| 5,899,855 | A | 5/1999 | Brown |
| 5,904,708 | A | 5/1999 | Goedeke |
| 5,913,998 | A | 6/1999 | Butler et al. |
| 5,914,026 | A | 6/1999 | Blubaugh, Jr. et al. |
| 5,917,346 | A | 6/1999 | Gord |
| 5,919,215 | A | 7/1999 | Wiklund et al. |
| 5,928,130 | A | 7/1999 | Schmidt |
| 5,928,155 | A | 7/1999 | Eggers et al. |
| 5,931,814 | A | 8/1999 | Alex et al. |
| 5,933,136 | A | 8/1999 | Brown |
| 5,944,661 | A | 8/1999 | Swette et al. |
| 5,957,854 | A | 9/1999 | Besson et al. |
| 5,957,903 | A | 9/1999 | Mirzaee et al. |
| 5,961,451 | A | 10/1999 | Reber et al. |
| 5,964,993 | A | 10/1999 | Blubaugh et al. |
| 5,965,380 | A | 10/1999 | Heller et al. |
| 5,971,922 | A | 10/1999 | Arita et al. |
| 5,976,085 | A | 11/1999 | Kimball et al. |
| 5,995,860 | A | 11/1999 | Sun et al. |
| 5,999,848 | A | 12/1999 | Gord et al. |
| 6,001,067 | A | 12/1999 | Shults et al. |
| 6,001,471 | A | 12/1999 | Bries et al. |
| 6,011,984 | A | 1/2000 | Van Antwerp et al. |
| 6,013,113 | A | 1/2000 | Mika |
| 6,016,448 | A | 1/2000 | Busacker et al. |
| 6,027,445 | A | 2/2000 | Von Bahr |
| 6,036,924 | A | 3/2000 | Simons et al. |
| 6,049,727 | A | 4/2000 | Crothall |
| 6,059,946 | A | 5/2000 | Yukawa et al. |
| 6,063,637 | A | 5/2000 | Arnold et al. |
| 6,081,735 | A | 6/2000 | Diab et al. |
| 6,081,736 | A | 6/2000 | Colvin et al. |
| 6,083,523 | A | 7/2000 | Dionne et al. |
| 6,083,710 | A | 7/2000 | Heller et al. |
| 6,088,608 | A | 7/2000 | Schulman et al. |
| 6,091,975 | A | 7/2000 | Daddona et al. |
| 6,093,172 | A | 7/2000 | Funderburk et al. |
| 6,103,033 | A | 8/2000 | Say et al. |
| 6,107,083 | A | 8/2000 | Collins et al. |
| 6,115,634 | A | 9/2000 | Donders et al. |
| 6,121,009 | A | 9/2000 | Heller et al. |
| 6,122,536 | A | 9/2000 | Sun et al. |
| 6,123,827 | A | 9/2000 | Wong et al. |
| 6,134,461 | A | 10/2000 | Say et al. |
| 6,135,978 | A | 10/2000 | Houben et al. |
| 6,144,869 | A | 11/2000 | Berner et al. |
| 6,162,611 | A | 12/2000 | Heller et al. |
| 6,167,614 | B1 | 1/2001 | Tuttle et al. |
| 6,168,568 | B1 | 1/2001 | Gavriely |
| 6,175,752 | B1 | 1/2001 | Say et al. |
| 6,180,416 | B1 | 1/2001 | Kurnik et al. |
| 6,187,062 | B1 | 2/2001 | Oweis et al. |
| 6,189,536 | B1 | 2/2001 | Martinez et al. |
| 6,201,980 | B1 | 3/2001 | Darrow et al. |
| 6,201,993 | B1 | 3/2001 | Kruse et al. |
| 6,206,856 | B1 | 3/2001 | Mahurkar |
| 6,208,894 | B1 | 3/2001 | Schulman et al. |
| 6,212,416 | B1 | 4/2001 | Ward et al. |
| 6,212,424 | B1 | 4/2001 | Robinson |
| 6,214,185 | B1 | 4/2001 | Offenbacher et al. |
| 6,223,083 | B1 | 4/2001 | Rosar |
| 6,230,059 | B1 | 5/2001 | Duffin |
| 6,233,080 | B1 | 5/2001 | Brenner et al. |
| 6,233,471 | B1 * | 5/2001 | Berner et al. ............ 600/345 |
| 6,241,863 | B1 | 6/2001 | Monbouquette |
| 6,248,067 | B1 | 6/2001 | Causey, III et al. |
| 6,256,522 | B1 | 7/2001 | Schultz |
| 6,259,937 | B1 | 7/2001 | Schulman et al. |
| 6,272,364 | B1 | 8/2001 | Kurnik |
| 6,272,480 | B1 | 8/2001 | Tresp et al. |
| 6,275,717 | B1 | 8/2001 | Gross et al. |
| 6,284,478 | B1 | 9/2001 | Heller et al. |
| 6,293,925 | B1 | 9/2001 | Safabash et al. |
| 6,299,578 | B1 | 10/2001 | Kurnik et al. |
| 6,300,002 | B1 | 10/2001 | Webb et al. |
| 6,302,855 | B1 | 10/2001 | Lav et al. |
| 6,309,351 | B1 | 10/2001 | Kurnik et al. |
| 6,309,884 | B1 | 10/2001 | Cooper et al. |
| 6,325,978 | B1 | 12/2001 | Labuda et al. |
| 6,325,979 | B1 | 12/2001 | Hahn et al. |
| 6,326,160 | B1 | 12/2001 | Dunn et al. |
| 6,329,161 | B1 | 12/2001 | Heller et al. |
| 6,329,929 | B1 | 12/2001 | Weijand et al. |
| 6,330,464 | B1 | 12/2001 | Colvin, Jr. et al. |
| 6,343,225 | B1 | 1/2002 | Clark, Jr. |
| 6,356,776 | B1 | 3/2002 | Berner et al. |
| 6,366,794 | B1 | 4/2002 | Moussy et al. |
| 6,368,274 | B1 | 4/2002 | Van Antwerp et al. |
| 6,370,941 | B2 | 4/2002 | Nakamura et al. |
| 6,379,301 | B1 | 4/2002 | Worthington et al. |
| 6,400,974 | B1 | 6/2002 | Lesho |
| 6,405,066 | B1 | 6/2002 | Essenpreis et al. |
| 6,409,674 | B1 | 6/2002 | Brockway et al. |
| 6,413,393 | B1 | 7/2002 | Van Antwerp et al. |
| 6,416,651 | B1 | 7/2002 | Millar |
| 6,424,847 | B1 | 7/2002 | Mastrototaro et al. |
| 6,447,448 | B1 | 9/2002 | Ishikawa et al. |
| 6,454,710 | B1 | 9/2002 | Ballerstadt et al. |
| 6,461,496 | B1 | 10/2002 | Feldman et al. |
| 6,466,810 | B1 | 10/2002 | Ward et al. |
| 6,471,689 | B1 | 10/2002 | Joseph et al. |
| 6,475,750 | B1 | 11/2002 | Han et al. |
| 6,477,392 | B1 | 11/2002 | Honigs et al. |
| 6,477,395 | B2 | 11/2002 | Schulman et al. |
| 6,481,440 | B2 | 11/2002 | Gielen et al. |
| 6,484,046 | B1 | 11/2002 | Say et al. |
| 6,498,043 | B1 | 12/2002 | Schulman et al. |
| 6,510,329 | B2 | 1/2003 | Heckel |
| 6,512,939 | B1 | 1/2003 | Colvin et al. |
| 6,520,326 | B2 | 2/2003 | McIvor et al. |
| 6,526,298 | B1 | 2/2003 | Khalil et al. |
| 6,527,729 | B1 | 3/2003 | Turcott |
| 6,544,212 | B2 | 4/2003 | Galley et al. |
| 6,546,268 | B1 | 4/2003 | Ishikawa et al. |
| 6,546,269 | B1 | 4/2003 | Kurnik |
| 6,547,839 | B2 | 4/2003 | Zhang et al. |
| 6,551,496 | B1 | 4/2003 | Moles et al. |
| 6,553,241 | B2 | 4/2003 | Mannheimer et al. |
| 6,553,244 | B2 | 4/2003 | Lesho et al. |
| 6,558,320 | B1 | 5/2003 | Causey et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,978 | B1 | 5/2003 | Conn et al. |
| 6,565,509 | B1 | 5/2003 | Say et al. |
| 6,569,521 | B1 | 5/2003 | Sheridan et al. |
| 6,572,545 | B2 | 6/2003 | Knobbe et al. |
| 6,574,490 | B2 | 6/2003 | Abbink et al. |
| 6,575,905 | B2 | 6/2003 | Knobbe et al. |
| 6,579,498 | B1 | 6/2003 | Eglise |
| 6,579,690 | B1 | 6/2003 | Bonnecaze et al. |
| 6,585,644 | B2 | 7/2003 | Lebel et al. |
| 6,585,763 | B1 | 7/2003 | Keilman et al. |
| 6,589,229 | B1 | 7/2003 | Connelly et al. |
| 6,591,125 | B1 | 7/2003 | Buse et al. |
| 6,595,919 | B2 | 7/2003 | Berner et al. |
| 6,605,072 | B2 | 8/2003 | Struys et al. |
| 6,607,509 | B2 | 8/2003 | Bobroff et al. |
| 6,613,379 | B2 | 9/2003 | Ward et al. |
| 6,618,934 | B1 | 9/2003 | Feldman et al. |
| 6,633,772 | B2 | 10/2003 | Ford et al. |
| 6,641,533 | B2 | 11/2003 | Causey et al. |
| 6,642,015 | B2 | 11/2003 | Vachon et al. |
| 6,645,181 | B1 | 11/2003 | Lavi et al. |
| 6,648,821 | B2 | 11/2003 | Lebel et al. |
| 6,654,625 | B1 | 11/2003 | Say et al. |

| Patent/Publication | Date | Inventor |
|---|---|---|
| 6,673,022 B1 | 1/2004 | Bobo et al. |
| 6,673,596 B1 | 1/2004 | Sayler et al. |
| 6,683,535 B1 | 1/2004 | Utke |
| 6,694,191 B2 | 2/2004 | Starkweather et al. |
| 6,695,860 B1 | 2/2004 | Ward et al. |
| 6,699,188 B2 | 3/2004 | Wessel |
| 6,699,218 B2 | 3/2004 | Flaherty et al. |
| 6,702,857 B2 | 3/2004 | Brauker et al. |
| 6,702,972 B1 | 3/2004 | Markle |
| 6,721,587 B2 | 4/2004 | Gough |
| 6,731,976 B2 | 5/2004 | Penn et al. |
| 6,740,075 B2 | 5/2004 | Lebel et al. |
| 6,741,877 B1 | 5/2004 | Shults et al. |
| 6,810,290 B2 | 10/2004 | Lebel et al. |
| 6,869,413 B2 | 3/2005 | Langley et al. |
| 6,892,085 B2 | 5/2005 | McIvor et al. |
| 6,895,263 B2 | 5/2005 | Shin et al. |
| 6,925,393 B1 | 8/2005 | Kalatz et al. |
| 6,931,327 B2 | 8/2005 | Goode et al. |
| 6,952,604 B2 | 10/2005 | DeNuzzio et al. |
| 6,998,247 B2 | 2/2006 | Monfre et al. |
| 7,011,630 B2 | 3/2006 | Desai et al. |
| 7,025,743 B2 | 4/2006 | Mann et al. |
| 7,029,444 B2 | 4/2006 | Shin et al. |
| 7,060,059 B2 | 6/2006 | Keith et al. |
| 7,074,307 B2 | 7/2006 | Simpson et al. |
| 7,098,803 B2 | 8/2006 | Mann et al. |
| 7,108,778 B2 | 9/2006 | Simpson et al. |
| 7,134,999 B2 | 11/2006 | Brauker et al. |
| 7,169,289 B2 | 1/2007 | Schulein et al. |
| 7,192,450 B2 | 3/2007 | Brauker et al. |
| 7,229,288 B2 | 6/2007 | Stuart et al. |
| 7,261,690 B2 | 8/2007 | Teller et al. |
| 7,267,665 B2 | 9/2007 | Steil et al. |
| 7,276,029 B2 | 10/2007 | Goode et al. |
| 7,278,983 B2 | 10/2007 | Ireland et al. |
| 7,295,867 B2 | 11/2007 | Berner et al. |
| 7,354,420 B2 | 4/2008 | Steil et al. |
| 7,359,723 B2 | 4/2008 | Jones |
| 7,402,153 B2 | 7/2008 | Steil et al. |
| 7,417,164 B2 | 8/2008 | Suri |
| 7,426,408 B2 | 9/2008 | DeNuzzio et al. |
| 7,433,727 B2 | 10/2008 | Ward et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,618,368 B2 | 11/2009 | Brown |
| 7,624,028 B1 | 11/2009 | Brown |
| 7,640,032 B2 | 12/2009 | Jones |
| 7,640,048 B2 | 12/2009 | Dobbles et al. |
| 7,647,237 B2 | 1/2010 | Malave et al. |
| 7,998,071 B2 | 8/2011 | Goode et al. |
| 8,005,525 B2 | 8/2011 | Goode et al. |
| 8,010,174 B2 | 8/2011 | Goode et al. |
| 8,073,519 B2 | 12/2011 | Goode et al. |
| 8,073,520 B2 | 12/2011 | Kamath et al. |
| 8,128,562 B2 | 3/2012 | Goode et al. |
| 8,150,488 B2 | 4/2012 | Goode et al. |
| 8,167,801 B2 | 5/2012 | Goode et al. |
| 8,195,265 B2 | 6/2012 | Goode et al. |
| 8,229,536 B2 | 7/2012 | Goode et al. |
| 8,233,959 B2 | 7/2012 | Kamath et al. |
| 8,260,393 B2 | 9/2012 | Kamath et al. |
| 8,292,810 B2 | 10/2012 | Goode et al. |
| 8,346,338 B2 | 1/2013 | Goode et al. |
| 8,412,301 B2 | 4/2013 | Goode et al. |
| 8,423,113 B2 | 4/2013 | Shariati et al. |
| 8,435,179 B2 | 5/2013 | Goode et al. |
| 2001/0016682 A1 | 8/2001 | Berner et al. |
| 2001/0041830 A1 | 11/2001 | Varalli et al. |
| 2001/0051768 A1 | 12/2001 | Schulman et al. |
| 2002/0019022 A1 | 2/2002 | Dunn et al. |
| 2002/0026110 A1 | 2/2002 | Parris et al. |
| 2002/0026111 A1 | 2/2002 | Ackerman |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0065453 A1 | 5/2002 | Lesho et al. |
| 2002/0068860 A1 | 6/2002 | Clark, Jr. |
| 2002/0099282 A1* | 7/2002 | Knobbe et al. ............... 600/365 |
| 2002/0111547 A1 | 8/2002 | Knobbe et al. |
| 2002/0115920 A1 | 8/2002 | Rich et al. |
| 2002/0119711 A1 | 8/2002 | VanAntwerp et al. |
| 2002/0155615 A1 | 10/2002 | Novikov et al. |
| 2002/0161288 A1 | 10/2002 | Shin et al. |
| 2002/0198513 A1 | 12/2002 | Lebel et al. |
| 2003/0004432 A1 | 1/2003 | Assenheimer |
| 2003/0004457 A1 | 1/2003 | Andersson |
| 2003/0006669 A1 | 1/2003 | Pei et al. |
| 2003/0023171 A1 | 1/2003 | Sato et al. |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0050546 A1* | 3/2003 | Desai et al. ............... 600/347 |
| 2003/0070548 A1 | 4/2003 | Clausen |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0097082 A1 | 5/2003 | Purdy et al. |
| 2003/0100821 A1 | 5/2003 | Heller et al. |
| 2003/0120152 A1 | 6/2003 | Omiya |
| 2003/0125612 A1 | 7/2003 | Fox et al. |
| 2003/0125613 A1 | 7/2003 | Enegren et al. |
| 2003/0130616 A1* | 7/2003 | Steil et al. ............... 604/66 |
| 2003/0134347 A1 | 7/2003 | Heller et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0211625 A1 | 11/2003 | Cohan |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0217966 A1 | 11/2003 | Tapsak et al. |
| 2003/0225437 A1 | 12/2003 | Ferguson |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0024327 A1 | 2/2004 | Brodnick |
| 2004/0030285 A1 | 2/2004 | Lavi et al. |
| 2004/0030294 A1 | 2/2004 | Mahurkar |
| 2004/0039298 A1 | 2/2004 | Abreu |
| 2004/0039406 A1 | 2/2004 | Jessen |
| 2004/0045879 A1 | 3/2004 | Shults et al. |
| 2004/0068230 A1 | 4/2004 | Estes et al. |
| 2004/0078219 A1 | 4/2004 | Kaylor |
| 2004/0106857 A1 | 6/2004 | Gough |
| 2004/0143173 A1 | 7/2004 | Reghabi et al. |
| 2004/0152187 A1 | 8/2004 | Haight et al. |
| 2004/0152622 A1 | 8/2004 | Keith et al. |
| 2004/0167801 A1 | 8/2004 | Say et al. |
| 2004/0186362 A1 | 9/2004 | Brauker et al. |
| 2004/0186365 A1 | 9/2004 | Jin et al. |
| 2004/0199059 A1 | 10/2004 | Brauker et al. |
| 2004/0219664 A1 | 11/2004 | Heller et al. |
| 2004/0220517 A1 | 11/2004 | Starkweather et al. |
| 2005/0010265 A1 | 1/2005 | Baru Fassio et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0096519 A1 | 5/2005 | DeNuzzio et al. |
| 2005/0101847 A1 | 5/2005 | Routt et al. |
| 2005/0113653 A1 | 5/2005 | Fox et al. |
| 2005/0115832 A1 | 6/2005 | Simpson et al. |

| | | |
|---|---|---|
| 2005/0121322 A1 | 6/2005 | Say |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0187720 A1 | 8/2005 | Goode et al. |
| 2005/0192557 A1 | 9/2005 | Brauker et al. |
| 2005/0203360 A1 | 9/2005 | Brauker et al. |
| 2005/0211571 A1 | 9/2005 | Schulein et al. |
| 2005/0215871 A1 | 9/2005 | Feldman et al. |
| 2005/0215872 A1 | 9/2005 | Berner et al. |
| 2005/0239154 A1 | 10/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0100588 A1 | 5/2006 | Brunnberg et al. |
| 2006/0183984 A1 | 8/2006 | Dobbles et al. |
| 2006/0183985 A1 | 8/2006 | Brister et al. |
| 2006/0222566 A1 | 10/2006 | Brauker et al. |
| 2006/0258929 A1 | 11/2006 | Goode et al. |
| 2007/0016381 A1 | 1/2007 | Kamath et al. |
| 2007/0032706 A1 | 2/2007 | Kamath et al. |
| 2007/0049873 A1 | 3/2007 | Hansen et al. |
| 2007/0066873 A1 | 3/2007 | Kamath et al. |
| 2007/0203410 A1 | 8/2007 | Say et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2008/0021666 A1 | 1/2008 | Goode et al. |
| 2008/0033254 A1 | 2/2008 | Kamath et al. |
| 2008/0071157 A1 | 3/2008 | Mcgarraugh et al. |
| 2008/0071158 A1 | 3/2008 | Mcgarraugh et al. |
| 2008/0072663 A1 | 3/2008 | Keenan et al. |
| 2008/0183061 A1 | 7/2008 | Goode et al. |
| 2008/0183399 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0189051 A1 | 8/2008 | Goode et al. |
| 2008/0194936 A1 | 8/2008 | Goode et al. |
| 2008/0194937 A1 | 8/2008 | Goode et al. |
| 2008/0195967 A1 | 8/2008 | Goode et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0305009 A1 | 12/2008 | Gamsey et al. |
| 2008/0305506 A1 | 12/2008 | Suri |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0018418 A1 | 1/2009 | Markle et al. |
| 2009/0018426 A1 | 1/2009 | Markle et al. |
| 2009/0036758 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0061528 A1 | 3/2009 | Suri |
| 2009/0062635 A1 | 3/2009 | Brauker et al. |
| 2009/0076361 A1 | 3/2009 | Kamath et al. |
| 2009/0081803 A1 | 3/2009 | Gamsey et al. |
| 2009/0124877 A1 | 5/2009 | Goode, Jr. et al. |
| 2009/0124878 A1 | 5/2009 | Goode, Jr. et al. |
| 2009/0156924 A1 | 6/2009 | Shariati et al. |
| 2009/0177143 A1 | 7/2009 | Markle et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0264719 A1 | 10/2009 | Markle et al. |
| 2009/0287074 A1 | 11/2009 | Shults et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0022855 A1 | 1/2010 | Brauker et al. |
| 2010/0030053 A1 | 2/2010 | Goode, Jr. et al. |
| 2010/0030484 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0045465 A1 | 2/2010 | Brauker et al. |
| 2010/0081908 A1 | 4/2010 | Dobbles et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0234707 A1 | 9/2010 | Goode, Jr. et al. |
| 2010/0235106 A1 | 9/2010 | Goode, Jr. et al. |
| 2010/0240975 A1 | 9/2010 | Goode, Jr. et al. |
| 2010/0240976 A1 | 9/2010 | Goode, Jr. et al. |
| 2011/0118579 A1 | 5/2011 | Goode, Jr. et al. |
| 2011/0124997 A1 | 5/2011 | Goode, Jr. et al. |
| 2011/0125410 A1 | 5/2011 | Goode et al. |
| 2011/0130970 A1 | 6/2011 | Goode, Jr. et al. |
| 2011/0137601 A1 | 6/2011 | Goode, Jr. et al. |
| 2011/0218414 A1 | 9/2011 | Kamath et al. |
| 2011/0270062 A1 | 11/2011 | Goode et al. |

FOREIGN PATENT DOCUMENTS

| | | |
|---|---|---|
| EP | 0 107 634 | 5/1984 |
| EP | 0 127 958 | 12/1984 |
| EP | 0 286 118 | 10/1988 |
| EP | 0 288 793 | 11/1988 |
| EP | 0 320 109 | 6/1989 |
| EP | 0 352 610 | 1/1990 |
| EP | 0 352 631 | 1/1990 |
| EP | 0 353 328 | 2/1990 |
| EP | 0 390 390 | 10/1990 |
| EP | 0 406 473 | 1/1991 |
| EP | 0 440 044 | 8/1991 |
| EP | 0 441 252 | 8/1991 |
| EP | 0 467 078 | 1/1992 |
| EP | 0 534 074 | 3/1993 |
| EP | 0 563 795 | 10/1993 |
| EP | 0 323 605 | 1/1994 |
| EP | 0 647 849 | 4/1995 |
| EP | 0 424 633 | 1/1996 |
| EP | 0 776 628 | 6/1997 |

| | | |
|---|---|---|
| EP | 0 817 809 | 1/1998 |
| EP | 0 838 230 | 4/1998 |
| EP | 0 880 936 | 12/1998 |
| EP | 0 885 932 | 12/1998 |
| EP | 0 995 805 | 4/2000 |
| EP | 1 077 634 | 2/2001 |
| EP | 1 078 258 | 2/2001 |
| EP | 1 153 571 | 11/2001 |
| EP | 2 226 086 | 8/2010 |
| EP | 2 223 710 | 9/2010 |
| FR | 2656423 | 6/1991 |
| FR | 2760962 | 9/1998 |
| GB | 1 442 303 | 7/1976 |
| GB | 2149918 | 6/1985 |
| JP | 62083849 | 4/1997 |
| WO | WO 89/02720 | 4/1989 |
| WO | WO 90/00738 | 1/1990 |
| WO | WO 90/10861 | 9/1990 |
| WO | WO 92/13271 | 8/1992 |
| WO | WO 93/14693 | 8/1993 |
| WO | WO 94/22367 | 10/1994 |
| WO | WO 95/07109 | 3/1995 |
| WO | WO 96/14026 | 5/1996 |
| WO | WO 96/25089 | 8/1996 |
| WO | WO 96/30431 | 10/1996 |
| WO | WO 97/01986 | 1/1997 |
| WO | WO 97/28737 | 8/1997 |
| WO | WO 97/43633 | 11/1997 |
| WO | WO 98/24358 | 6/1998 |
| WO | WO 98/42249 | 10/1998 |
| WO | WO 99/56613 | 4/1999 |
| WO | WO 99/48419 | 9/1999 |
| WO | WO 99/58051 | 11/1999 |
| WO | WO 99/58973 | 11/1999 |
| WO | WO 00/12720 | 3/2000 |
| WO | WO 00/13002 | 3/2000 |
| WO | WO 00/13003 | 3/2000 |
| WO | WO 00/19887 | 4/2000 |
| WO | WO 00/32098 | 6/2000 |
| WO | WO 00/33065 | 6/2000 |
| WO | WO 00/59373 | 10/2000 |
| WO | WO 00/74753 | 12/2000 |
| WO | WO 00/78210 | 12/2000 |
| WO | WO 01/12158 | 2/2001 |
| WO | WO 01/16579 | 3/2001 |
| WO | WO 01/20019 | 3/2001 |
| WO | WO 01/20334 | 3/2001 |
| WO | WO 01/34243 | 5/2001 |
| WO | WO 01/43660 | 6/2001 |
| WO | WO 01/52727 | 7/2001 |
| WO | WO 01/58348 | 8/2001 |
| WO | WO 01/68901 | 9/2001 |
| WO | WO 01/69222 | 9/2001 |
| WO | WO 01/88524 | 11/2001 |
| WO | WO 01/88534 | 11/2001 |
| WO | WO 02/24065 | 3/2002 |
| WO | WO 02/082989 | 10/2002 |
| WO | WO 02/089666 | 11/2002 |
| WO | WO 02/100266 | 12/2002 |
| WO | WO 03/101862 | 12/2003 |
| WO | WO 2004/052190 | 6/2004 |
| WO | WO 2004/060455 | 7/2004 |
| WO | WO 2004/110256 | 12/2004 |
| WO | WO 2005/011489 | 2/2005 |
| WO | WO 2005/012873 | 2/2005 |
| WO | WO 2005/026689 | 3/2005 |
| WO | WO 2005/032400 | 4/2005 |
| WO | WO 2005/057168 | 6/2005 |
| WO | WO 2005/057175 | 6/2005 |
| WO | WO 2005/078424 | 8/2005 |
| WO | WO 2006/050405 | 5/2006 |
| WO | WO 2006/105146 | 10/2006 |
| WO | WO 2006/118713 | 11/2006 |
| WO | WO 2006/131288 | 12/2006 |
| WO | WO 2007/002579 | 1/2007 |
| WO | WO 2007/065285 | 6/2007 |
| WO | WO 2007/114943 | 10/2007 |
| WO | WO 2007/127606 | 11/2007 |
| WO | WO 2007/143225 | 12/2007 |
| WO | WO 2008/076868 | 6/2008 |

OTHER PUBLICATIONS

Moussy, Francis (Nov. 2002) Implantable Glucose Sensor: Progress and Problems, Sensors, 1:270-273.

Samuels, M.P. 2004. The effects of flight and altitude. Arch Dis Child. 89: 448-455.

Thijssen et al. 1984. A Kalman Filter for Calibration, Evaluation of Unknown Samples and Quality Control in Drifting Systems, Part 1. Theory and Simulations, Anal Chim Acta 156: 87-101.

Thijssen et al. 1985. A Kalman Filter for Calibration, Evaluation of Unknown Samples and Quality Control in Drifting Systems, Part 3. Variance Reduction, Anal Chim Acta. 173: 265-272.

Thijssen et al. 1985. A Kalman Filter for Calibration, Evaluation of Unknown Samples and Quality Control in Drifting Systems, Part 4. Flow Injection Analysis, Anal Chim Acta. 174: 27-40.

Thijssen, P.C. 1984. A Kalman Filder for Calibration, Evaluation of Unknown Samples and Quality Control in Drifting Systems, Part 2. Optimal Designs, Anal Chim Acta. 162: 253-262.

Ward et al. 2004. A wire-based dual-analyte sensor for Glucose and Lactate: In Vitro and In Vivo Evaluation, Diab Tech Therapeut. 6(3): 389-401.

Electronic File History of U.S. Appl. No. 10/648,849, filed Aug. 22, 2003 containing Office Action(s) dated Dec. 18, 2008, Jun. 23, 2009, Apr. 1, 2010, Feb. 3, 2011, Apr. 27, 2011 and Jun. 24, 2011 and Applicant Response(s) filed Oct. 12, 2007, Jan. 14, 2009, Mar. 17, 2009, Oct. 23, 2009, Jul. 1, 2010, Jul. 29, 2010, and Feb. 8, 2010 as of Aug. 8, 2011.

Electronic File History of U.S. Appl. No. 12/579,339, filed Oct. 14, 2009 containing Office Action(s) dated Oct. 29, 2010 and Apr. 18, 2011 and Applicant(s) Response(s) filed Jan. 31, 2011.

Electronic File History of U.S. Appl. No. 12/353,787, filed Jan. 14, 2009 containing Office Action(s) dated Aug. 6, 2010, Jan. 25, 2011 and Apr. 6, 2011 and Applicant(s) Response(s) filed Nov. 8, 2010, Mar. 24, 2011 and Apr. 8, 2011 as of Apr. 13, 2011.

Electronic File History of U.S. Appl. No. 12/789,153, filed May 27, 2010 containing Office Action(s) dated Mar. 29, 2011, May 25, 2011 and Aug. 2, 2011 and Applicant(s) Response(s) filed Apr. 26, 2011 as of Aug. 2, 2011.

Electronic File History of U.S. Appl. No. 12/791,686, filed Jun. 1, 2010 containing Office Action(s) dated Apr. 22, 2011 and Jun. 7, 2011 and Applicant(s) Response(s) filed May 23, 2011 as of Aug. 2, 2011.

Electronic File History of U.S. Appl. No. 12/791,791, filed Jun. 1, 2010 containing Office Action(s) dated May 24, 2011 and Jul. 21, 2011 and Applicant(s) Response(s) filed Jun. 24, 2011 as of Aug. 2, 2011.

Electronic File History of U.S. Appl. No. 12/579,363, filed Oct. 14, 2009 containing Office Action(s) dated Oct. 29, 2010, Apr. 12, 2011 and Jul. 5, 2011 and Applicant(s) Response(s) filed Jan. 31, 2011 and Jun. 10, 2011 as of Jun. 10, 2011.

Electronic File History of U.S. Appl. No. 12/579,357, filed Oct. 14, 2009 containing Office Action(s) dated Oct. 1, 2010 and Feb. 17, 2011 and Applicant(s) Response(s) filed Nov. 15, 2010, Mar. 25, 2011 and Apr. 8, 2011 as of Apr. 12, 2011.

Electronic File History of U.S. Appl. No. 12/579,385, filed Oct. 14, 2009 containing Office Action(s) dated Aug. 23, 2010, Feb. 17, 2011 and Jul. 14, 2011 and Applicant(s) Response(s) filed Nov. 16, 2010, Apr. 18, 2011 and Jul. 25, 2011 as of Jul. 25, 2011.

Electronic File History of U.S. Appl. No. 12/579,388, filed Oct. 14, 2009 containing Office Action(s) dated Nov. 26, 2010, May 12, 2011 and May 24, 2011 and Applicant(s) Responses filed Feb. 25, 2011, Feb. 28, 2011 and Jul. 12, 2011 as of Jul. 12, 2011.

Electronic File History of U.S. Appl. No. 12/579,392, filed Oct. 14, 2009 containing Office Action(s) dated Dec. 28, 2010 and Jul. 26, 2011 and Applicant(s) Responses filed Apr. 25, 2011 as of Jul. 26, 2011.

Electronic File History of U.S. Appl. No. 12/579,374, filed Oct. 14, 2009 containing Office Action(s) dated Nov. 16, 2010, May 9, 2011 and Jul. 13, 2011 and Applicant(s) Response(s) filed Feb. 16, 2011 and Jun. 13, 2011 as of Jul. 13, 2011.
Electronic File History of U.S. Appl. No. 12/731,980, filed Mar. 25, 2010 containing Office Action(s) dated Feb. 4, 2011, May 9, 2011 and Aug. 2, 2011 and Applicant(s) Response(s) filed Feb. 28, 2011 as of Aug. 2, 2011.
Electronic File History of U.S. Appl. No. 12/787,217, filed May 25, 2010 containing Office Action(s) dated Mar. 11, 2011 and May 23, 2011 and Applicant(s) Response(s) filed Jun. 13, 2011 as of Aug. 8, 2011.
Electronic File History of U.S. Appl. No. 11/498,410, filed Aug. 2, 2006 containing Office Action(s) dated Nov. 12, 2010 and Feb. 17, 2011 and Applicant(s) Response(s) filed Oct. 12, 2007 and Dec. 1, 2010 as of Apr. 13, 2011.
Electronic File History of U.S. Appl. No. 12/353,799, filed Jan. 14, 2009 containing Office Action(s) dated Aug. 6, 2010, Jan. 25, 2011 and Feb. 8, 2011 and Applicant(s) Response(s) filed Nov. 8, 2010, Jan. 26, 2011 and Feb. 28, 2011 as of Apr. 13, 2011.
Electronic File History of U.S. Appl. No. 11/515,443, filed Sep. 1, 2006 containing Office Action(s) dated Mar. 10, 2011, Jun. 23, 2011 and Aug. 1, 2011 and Applicant(s) Response(s) filed Oct. 12, 2007 and Apr. 5, 2011 as of Aug. 1, 2011.
Aalders et al. 1991. Development of a wearable glucose sensor; studies in healthy volunteers and in diabetic patients. The International Journal of Artificial Organs 14(2):102-108.
Abe et al. 1992. Characterization of glucose microsensors for intracellular measurements. Anal. Chem. 64(18):2160-2163.
Abel et al. 1984. Experience with an implantable glucose sensor as a prerequisite of an artificial beta cell, Biomed. Biochim. Acta 43(5):577-584.
Abel et al. 2002. Biosensors for in vivo glucose measurement: can we cross the experimental stage. Biosens Bioelectron 17:1059-1070.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Mifflin Company, 2002. Answers. com Nov. 7, 2006 http://www. Answers.com/topic/xenogenic.
Armour et al. Dec. 1990. Application of Chronic Intravascular Blood Glucose Sensor in Dogs. Diabetes 39:1519-1526.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Aussedat et al. 1997. A user-friendly method for calibrating a subcutaneous glucose sensor-based hypoglycaemic alarm. Biosensors & Bioelectronics 12(11):1061-1071.
Bailey et al. 2007. Reduction in hemoglobin A1c with real-time continuous glucose monitoring: results from a 12-week observational study. Diabetes Technology & Therapeutics 9(3):203-210.
Baker et al. 1993. Dynamic concentration challenges for biosensor characterization. Biosensors & Bioelectronics 8:433-441.
Baker et al. 1996. Dynamic delay and maximal dynamic error in continuous biosensors. Anal Chem 68(8):1292-1297.
Bani Amer, M. M. 2002. An accurate amperometric glucose sensor based glucometer with eliminated cross-sensitivity. J Med Eng Technol 26(5):208-213.
Bard et al. 1980. Electrochemical Methods. John Wiley & Sons, pp. 173-175.
Beach et al. 1999. Subminiature implantable potentiostat and modified commercial telemetry device for remote glucose monitoring. IEEE Transactions on Instrumentation and Measurement 48(6):1239-1245.
Bellucci et al. Jan. 1986. Electrochemical behaviour of graphite-epoxy composite materials (GECM) in aqueous salt solutions, Journal of Applied Electrochemistry, 16(1):15-22.
Bessman et al., Progress toward a glucose sensor for the artificial pancreas, Proceedings of a Workshop on Ion-Selective Microelectrodes, Jun. 4-5, 1973, Boston, MA, 189-197.

Biermann et al. 2008. How would patients behave if they were continually informed of their blood glucose levels? A simulation study using a "virtual" patient. Diab. Thechnol. & Therapeut., 10:178-187.
Bindra et al. 1989. Pulsed amperometric detection of glucose in biological fluids at a surface-modified gold electrode. Anal Chem 61:2566-2570.
Bindra et al. 1991. Design and in Vitro Studies of a Needle-Type Glucose Senso for Subcutaneous Monitoring. Anal. Chem 63:1692-96.
Bisenberger et al. 1995. A triple-step potential waveform at enzyme multisensors with thick-film gold electrodes for detection of glucose and sucrose. Sensors and Actuators, B 28:181-189.
Bland et al. 1986. Statistical methods for assessing agreement between two methods of clinical measurement. Lancet 1:307-310.
Bland et al. 1990. A note on the use of the intraclass correlation coefficient in the evaluation of agreement between two methods of measurement. Comput. Biol. Med. 20(5):337-340.
Bobbioni-Harsch et al. 1993. Lifespan of subcutaneous glucose sensors and their performances during dynamic glycaemia changes in rats, J. Biomed. Eng. 15:457-463.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics, 2(Suppl 1):543-48.
Bode, B. W. 2000. Clinical utility of the continuous glucose monitoring system. Diabetes Technol Ther, 2(Suppl 1):S35-41.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bolinder et al. 1992. Microdialysis measurement of the absolute glucose concentration in subcutaneous adipose tissue allowing glucose monitoring in diabetic patients. Diabetologia 35:1177-1180.
Bolinder et al. 1997. Self-monitoring of blood glucose in type 1 diabetic patients: Comparison with continuous microdialysis measurements of glucose in subcutaneous adipose tissue during ordinary life conditions. Diabetes Care 20(1):64-70.
Bott, A. W. 1997. A Comparison of Cyclic Voltammetry and Cyclic Staircase Voltammetry Current Separations 16:1, 23-26.
Bott, A. 1998. Electrochemical methods for the determination of glucose. Current Separations 17(1):25-31.
Bowman, L.; Meindl, J. D. 1986. The packaging of implantable integrated sensors. IEEE Trans Biomed Eng BME33(2):248-255.
Brauker et al. Jun. 27, 1996. Local Inflammatory Response Around Diffusion Chambers Containing Xenografts Transplantation 61(12):1671-1677.
Braunwald, 2008. Biomarkers in heart failure. *N. Engl. J. Med.*, 358: 2148-2159.
Bremer et al. 1999. Is blood glucose predictable from previous values? A solicitation for data. Diabetes 48:445-451.
Bremer et al. 2001. Benchmark data from the literature for evaluation of new glucose sensing technologies. Diabetes Technology & Therapeutics 3(3):409-418.
Brooks et al. "Development of an on-line glucose sensor for fermentation monitoring," Biosensors, 3:45-56 (1987/88).
Bruckel et al. 1989. In vivo measurement of subcutaneous glucose concentrations with an enzymatic glucose sensor and a wick method. Klin Wochenschr 67:491-495.
Brunstein et al. 1989. Preparation and validation of implantable electrodes for the measurement of oxygen and glucose. Biomed Biochim. Acta 48(11/12):911-917.
Cai et al. 2004. A wireless, remote query glucose biosensor based on a pH-sensitive polymer. Anal Chem 76(4):4038-4043.
Cameron et al. 1997. Micromodular Implants to provide electrical stimulation of paralyzed muscles and limbs. IEEE Transactions on Biomedical Engineering 44(9):781-790.
Campanella et al. 1993. Biosensor for direct determination of glucose and lactate in undiluted biological fluids. Biosensors & Bioelectronics 8:307-314.

Candas et al (1994). "An adaptive plasma glucose controller based on a nonlinear insulin/glucose model." *IEEE Transactions on Biomedical Engineering*, 41(2): 116-124.

Cass et al. "Ferrocene-mediated enzyme electrodes for amperometric determination of glucose," Anal. Chem., 36:667-71 (1984).

Cassidy et al., Apr. 1993. Novel electrochemical device for the detection of cholesterol or glucose, Analyst, 118:415-418.

Chase et al. 2001. Continuous subcutaneous glucose monitoring in children with type 1 diabetes. Pediatrics 107:222-226.

Chen et al. 2002. Defining the period of recovery of the glucose concentration after its local perturbation by the implantation of a miniature sensor. Clin. Chem. Lab. Med. 40:786-789.

Chia et al. 2004. Glucose sensors: toward closed loop insulin delivery. Endocrinol Metab Clin North Am 33:175-95.

Choleau et al. 2002. Calibration of a subcutaneous amperometric glucose sensor implanted for 7 days in diabetic patients. Part 1. Effect of measurement uncertainties on the determination of sensor sensitivity and background current. Biosensors and Bioelectronics 17:641-646.

Choleau et al. 2002. Calibration of a subcutaneous amperometric glucose sensor implanted for 7 days in diabetic patients. Part 2. Superiority of the one-point calibration method. Biosensors and Bioelectronics 17:647-654.

Ciba® Irgacure® 2959 Photoinitiator, Product Description, Ciba Specialty Chemicals Inc., Basel, Switzerland, Apr. 2, 1998.

Claremont et al. 1986. Subcutaneous implantation of a ferrocene-mediated glucose sensor in pigs. Diabetologia 29:817-821.

Claremont et al. Jul. 1986. Potentially-impintable, ferrocene-mediated glucose sensor. J. Biomed. Eng. 8:272-274.

Clark et al., 1981. One-minute electrochemical enzymic assay for cholesterol in biological materials, Clin. Chem. 27(12):1978-1982.

Clark et al. 1987. Configurational cyclic voltammetry: increasing the specificity and reliablity of implanted electrodes, IEEE/Ninth Annual Conference of the Engineering in Medicine and Biology Society, pp. 0782-0783.

Clark et al. 1988. Long-term stability of electroenzymatic glucose sensors implanted in mice. Trans Am Soc Artif Intern Organs 34:259-265.

Clarke et al. Sep.-Oct. 1987. Evaluating Clinical Accuracy of Systems for Self-Monitoring of Blood Glucose. Diabetes Care 10(5):622-628.

CLSI. Performance metrics for continuous interstitial glucose monitoring; approved guideline, CLSI document POCT05-A. Wayne, PA: Clinical and Laboratory Standards Institute: 2008 28(33), 72 pp.

Colangelo et al. 1967. Corrosion rate measurements in vivo, Journal of Biomedical Materials Research, 1:405-414.

Colowick et al. 1976. Methods in Enzymlology, vol. XLIV, Immobilized Enzymes. New York: Academic Press.

Cox et al. 1985. Accuracy of perceiving blood glucose in IDDM. Diabetes Care 8(6):529-536.

Csöregi et al. 1994. Amperometric microbiosensors for detection of hydrogen peroxide and glucose based on peroxidase-modified carbon fibers. Electroanalysis 6:925-933.

Csoregi et al., 1994. Design, characterization, and one-point in vivo calibration of a subcutaneously implanted glucose electrode. Anal Chem. 66(19):3131-3138.

Currie et al., Novel non-intrusive trans-dermal remote wireless micro-fluidic monitoring systme applied to continuous glucose and lactate assays for casualty care and combat readiness assessment, RTO HFM Symposium, St. Pete Beach, RTO-MP-HFM-109, Aug. 16-18, 2004, 18 pp.

Danielsson et al. 1988. Enzyme thermistors, Methods in Enzymology, 137:181-197.

Dassau et al., In silico evaluation platform for artifical pancreatic β-cell development—a dynamic simulator for closed loop control with hardware-in-the-loop, Diabetes Technology & Therapeutics, 11(3):1-8, 2009.

Davies, et al. 1992. Polymer membranes in clinical sensor applications. I. An overview of membrane function, Biomaterials, 13(14):971-978.

Davis et al. 1983. Bioelectrochemical fuel cell and sensor based on a quinoprotein, alcohol dehydrogenase. *Enzyme Microb. Technol.*, vol. 5, Sep., 383-388.

Deutsch et al., "Time series analysis and control of blood glucose levels in diabetic patients". Computer Methods and Programs in Biomedicine 41 (1994) 167-182.

Diabetes Educational Video Game Recognized by Software Publishers Association, Press Release, Novo Nordisk, Mar. 14, 1994.

Direct 30/30® Blood Glucose Sensor, (Markwell Medical) Catalog, ©1990, ELCO Diagnostics Company. 1 page.

Dixon et al. 2002. Characterization in vitro and in vivo of the oxygen dependence of an enzyme/polymer biosensor for monitoring brain glucose. Journal of Neuroscience Methods 119:135-142.

DuPont[1] Dimension AR® (Catalog), 1998.

Durliat et al. 1976. Spectrophotometric and electrochemical determinations of L(+)-lactate in blood by use of lactate dehydrogenase from yeast, Clin. Chem. 22(11):1802-1805.

Edwards Lifesciences. Accuracy for your and your patients. Marketing materials, 4 pp. 2002.

El Degheidy et al. 1986. Optimization of an implantable coated wire glucose sensor. J. Biomed Eng. 8: 121-129.

El-Khatib et al. 2007. Adaptive closed-loop control provides blood-glucose regulation using dual subcutaneous insulin and glucagon infusion in diabetic swine, Journal of Diabetes Science and Technology, 1(2):181-192.

El-Sa'ad et al. 1990. Moisture Absorption by Epoxy Resins: the Reverse Thermal Effect. Journal of Materials Science 25:3577-3582.

Ernst et al. 2002. Reliable glucose monitoring through the use of microsystem technology. Anal. Bioanal. Chem. 373:758-761.

Fabietti et al. 2007. Clinical validation of a new control-oriented model of insulin and glucose dynamcs in subjects with type 1 diabetes, Diabetes Technology & Therapeutics, 9(4):327-338.

Fahy et al., An analysis: hyperglycemic intensive care patients need continuous glocuse monitoring—easier said than done, Journal of Diabetese Science and Technology, 2(2):201-204, Mar. 2008.

Fare et al. 1998. Functional characterization of a conducting polymer-based immunoassay system. Biosensors & Bioelectronics 13(3-4):459-470.

Feldman et al. 2003. A continuous glucose sensor based on wired enzyme technology—results from a 3-day trial in patients with type 1 diabetes. Diabetes Technol Ther 5(5):769-779.

Fischer et al. 1987. Assessment of subcutaneous glucose concentration: validation of the wick technique as a reference for implanted electrochemical sensors in normal and diabetic dogs, Diabetologia 30:940-945.

Fischer et al. 1989. Oxygen Tension at the Subcutaneous Implantation Site of Glucose Sensors. Biomed. Biochem 11/12:965-972.

Fischer et al. 1995. Hypoglycaemia-warning by means of subcutaneous electrochemical glucose sensors: an animal study, Horm. Metab. Rese. 27:53.

Freedman et al. 1991. Statistics, Second Edition, W.W. Norton & Company, p. 74.

Freiberger, Paul, Video Game Takes on Diabetes Superhero 'Captain Novolin' Offers Treatment Tips, San Francisco Examiner, Jun. 26, 1992, Fourth Edition, Business Sec. B1.

Frohnauer et al. 2001. Graphical human insulin time-activity profiles using standardized definitions. Diabetes Technology & Therapeutics 3(3):419-429.

Frost et al. 2002. Implantable chemical sensors for real-time clinical monitoring: Progress and challenges. Current Opinion in Chemical Biology 6:633-641.

Gabbay et al. 2008. Optical coherence tomography-based continuous noninvasive glucose monitoring in patients with diabetes. Diab. Thechnol. & Therapeut., 10:188-193.

Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA® blood chemistry monitor for glucose in healthy and diabetic volunteers, Journal of Diabetese Science and Technology, 2(2):182-193, Mar. 2008.

Garg et al. 1999. Correlation of fingerstick blood glucose measurements with GlucoWatch biographer glucose results in young subjects with type 1 diabetes. Diabetes Care 22(10):1708-1714.

Garg et al. 2004. Improved Glucose Excursions Using an Implantable Real-Time continuous Glucose Sensor in Adults with Type I Diabetes. Diabetes Care 27:734-738.

Gerritsen et al. 1999. Performance of subcutaneously implanted glucose sensors for continuous monitoring. The Netherlands Journal of Medicine 54:167-179.

Gerritsen, M. 2000. Problems associated with subcutaneously implanted glucose sensors. Diabetes Care 23(2):143-145.

Gilligan et al. 1994. Evaluation of a subcutaneous glucose sensor out to 3 months in a dog model. Diabetes Care 17(8):882-887.

Gilligan et al. 2004, Feasibility of continuous long-term glucose monitoring from a subcutaneous glucose sensor in humans. Diabetes Technol Ther 6:378-386.

Godsland et al. 2001. Maximizing the Success Rate of Minimal Model Insulin Sensitivity Measurement in Humans: The Importance of Basal Glucose Levels. The Biochemical Society and the Medical Research Society, 1-9.

Gouda et al., Jul. 4, 2003. Thermal inactiviation of glucose oxidase, The Journal of Biological Chemistry, 278(27):24324-24333.

Gough et al. 2000. Immobilized glucose oxidase in implantable glucose sensor technology. Diabetes Technology & Therapeutics 2(3):377-380.

Gough et al. 2003. Frequency characterization of blood glucose dynamics. Annals of Biomedical Engineering 31:91-97.

Gross et al. 2000. Efficacy and reliability of the continuous glucose monitoring system. Diabetes Technology & Therapeutics, 2(Suppl 1):519-26.

Gross et al. 2000. Performance evaluation of the MiniMed® continuous glucose monitoring system during patient home use. Diabetes Technology & Therapeutics 2(1):49-56.

Guerci et al., Clinical performance of CGMS in type 1 diabetic patents treated by continuous subcutaneous insulin infusion using insulin analogs, Diabetes Care, 26:582-589, 2003.

Hall et al. 1998. Electrochemical oxidation of hydrogen peroxide at platinum electrodes. Part I: An adsorption-controlled mechanism. Electrochimica Acta, 43(5-6):579-588.

Hall et al. 1998. Electrochemical oxidation of hydrogen peroxide at platinum electrodes. Part II: Effect of potential. Electrochimica Acta 43(14-15):2015-2024.

Hall et al. 1999. Electrochemical oxidation of hydrogen peroxide at platinum electrodes. Part III: Effect of temperature. Electrochimica Acta, 44:2455-2462.

Hall et al. 1999. Electrochemical oxidation of hydrogen peroxide at platinum electrodes. Part IV: Phosphate buffer dependence. Electrochimica Acta, 44:4573-4582.

Hall et al. 2000. Electrochemical oxidation of hydrogen peroxide at platinum electrodes. Part V: Inhibition by chloride. Electrochimica Acta, 45:3573-3579.

Hamilton Syringe Selection Guide. 2006. Syringe Selection. www.hamiltoncompany.com.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes Care*, 17(5): 387-396.

Heise et al. 2003. Hypoglycemia warning signal and glucose sensors: Requirements and concepts. Diabetes Technology & Therapeutics 5:563-571.

Heller, "Electrical wiring of redox enzymes," *Acc. Chem. Res.*, 23:128-134 (1990).

Heller, A. 1992. Electrical Connection of Enzyme Redox Centers to Electrodes. J. Phys. Chem. 96:3579-3587.

Heller, A. 1999. Implanted electrochemical glucose sensors for the management of diabetes. Annu Rev Biomed Eng 1:153-175.

Heller, A. 2003. Plugging metal connectors into enzymes. Nat Biotechnol 21:631-2.

Hicks, 1985. In Situ Monitoring, Clinical Chemistry, 31(12):1931-1935.

Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.

Hoel, Paul G. 1976. Elementary Statistics, Fourth Edition. John Wiley & Sons, Inc.. pp. 113-114.

Hrapovic et al. 2003. Picoamperometric detection of glucose at ultrasmall platinum-based biosensors: preparation and characterization. Anal Chem 75:3308-3315.

http://www.merriam-webster.com/dictionary, definition for "aberrant," Aug. 19, 2008, p. 1.

Hu, et al. 1993. A needle-type enzyme-based lactate sensor for in vivo monitoring, Analytica Chimica Acta, 281:503-511.

Huang et al., "A 0.5mW Passive Telemetry IC for Biomedical Applications," Proceedings of the 23rd European Solid-State Circuits Conference (ESSCIRC '97), pp. 172-175, Sep. 1997, Southampton, UK.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode. U.S. Department of Commerce/NTIS, pp. 1-116.

Hunter et al. Mar. 31, 2000. Minimally Invasive Glucose Sensor and Insulin Delivery System. MIT Home Automation and Healthcare Consortium. Progress Report No. 2-5. 17 pages.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301.

Jablecki et al. 2000. Simulations of the frequency response of implantable glucose sensors. Analytical Chemistry 72:1853-1859.

Jaffari et al., Recent advances in amperometric glucose biosensors for in vivo monitoring, Physiol. Meas. 16 (1995) 1-15.

Jaremko et al. 1998. Advances toward the implantable artificial pancreas for treatment of diabetes. Diabetes Care 21(3):444-450.

Jensen et al. 1997. Fast wave forms for pulsed electrochemical detection of glucose by incorporation of reductive desorption of oxidation products. Analytical Chemistry 69(9):1776-1781.

Jeong et al. 2003. In vivo calibration of the subcutaneous amperometric glucose sensors using a non-enzyme electrode. Biosensors and Bioelectronics 19:313-319.

Jeutter, D. C. 1982. A transcutaneous implanted battery-recharging and biotelemeter power switching system. IEEE Trans Biomed Eng 29:314-321.

Jeutter et al. 1993. Design of a radio-linked implantable cochlear prosthesis using surface acoustic wave devices. IEEE Transactions on ultrasonics, ferroelectrics and frequency control 40(5):469-477.

Jobst et al., Thin-Film Microbiosensors for Glucose-Lactate Monitoring, Anal Chem. (1996) 68(18): 3173-3179.

Johnson (1991). "Reproducible electrodeposition of biomolecules for the fabrication of miniature electroenzymatic biosensors," *Sensors and Actuators B*, 5:85-89.

Johnson et al. 1992. In vivo evaluation of an electroenzymatic glucose sensor implanted in subcutaneous tissue. Biosensors & Bioelectronics, 7:709-714.

Joung et al. 1998. An energy transmission system for an artificial heart using leakage inductance compensation of transcutaneous transformer. IEEE Transactions on Power Electronics 13(6):1013-1022.

Jovanovic, L. 2000. The role of continuous glucose monitoring in gestational diabetes mellitus. Diabetes Technology & Therapeutics, 2 Suppl 1, S67-71.

Kacaniklic May-Jun. 1994. Electroanalysis, 6(5-6):381-390.

Kamath et al. Calibration of a continuous glucose monitor: effect of glucose rate of change, Eighth Annual Diabetes Technology Meeting, Nov. 13-15, 2008, p. A88.

Kang et al. 2003. In vitro and short-term in vivo characteristics of a Kel-F thin film modified glucose sensor. Anal Sci 19:1481-1486.

Kaufman. 2000. Role of the continuous glucose monitoring system in pediatric patients. Diabetes Technology & Therapeutics 2(1):S-49-S-52.

Kaufman et al. 2001. A pilot study of the continuous glucose monitoring system. Diabetes Care 24(12):2030-2034.

Kawagoe et al. 1991. Enzyme-modified organic conducting salt microelectrode, Anal. Chem. 63:2961-2965.

Keedy et al. 1991. Determination of urate in undiluted whole blood by enzyme electrode. *Biosensors & Bioelectronics*, 6: 491-499.

Kerner et al. 1988. A potentially implantable enzyme electrode for amperometric measurement of glucose, Horm Metab Res Suppl. 20:8-13.

Kerner et al. "The function of a hydrogen peroxide-detecting electroenzymatic glucose electrode is markedly impaired in human sub-cutaneous tissue and plasma," Biosensors & Bioelectronics, 8:473-482 (1993).

Kerner, W. 2001. Implantable glucose sensors: Present status and future developments. Exp. Clin. Endocrinol. Diabetes 109(Suppl 2):S341-346.

Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.

Ko, Wen H. 1985. Implantable Sensors for Closed-Loop Prosthetic Systems, Futura Pub. Co., Inc., Mt. Kisco, NY, Chapter 15:197-210.

Kondo et al. 1982. A miniature glucose sensor, implantable in the blood stream. Diabetes Care. 5(3):218-221.

Koschinsky et al. 1988. New approach to technical and clinical evaluation of devices for self-monitoring of blood glucose. Diabetes Care 11(8): 619-619.

Koschinsky et al. 2001. Sensors for glucose monitoring: Technical and clinical aspects. Diabetes Metab. Res. Rev. 17:113-123.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kovatchev et al. Aug. 2004. Evaluating the accuracy of continuous glucose-monitoring sensors: continuous glucose-error grid analysis illustrated by TheraSense Freestyle Navigator data. Diabetes Care 27(8):1922-1928.

Kraver et al. 2001. A mixed-signal sensor interface microinstrument. Sensors and Actuators A 91:266-277.

Krouwer, J. S. 2002. Setting performance goals and evaluating total analytical error for diagnostic assays. Clinical Chemistry 48(6):919-927.

Kruger et al. 2000. Psychological motivation and patient education: A role for continuous glucose monitoring. Diabetes Technology & Therapeutics, 2(Suppl 1):S93-97.

Kulys et al., 1994. Carbon-paste biosensors array for long-term glucose measurement, Biosensors& Beioelectronics, 9:491-500.

Kunjan et al., Automated blood sampling and glocuse sensing in critical care settings, Journal of Diabetes Science and Technology 2(3):194-200, Mar. 2008.

Kurnik et al. 1999. Application of the mixtures of experts' algorithm for signal processing in a noninvasive glucose monitoring system. Sensors and Actuators B, 60:19-26.

Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310.

LaCourse et al. 1993. Optimization of waveforms for pulsed amperometric detection of carbohydrates based on pulsed voltammetry. Analytical Chemistry 65:50-52.

Ladd et al., Structure Determination by X-ray Crystallography, 3rd ed. Plenum, 1996, Ch. 1, pp. xxi-xxiv and 1-58.

Lehmann et al. May 1994. Retrospective valication of a physiological model of glucose-iunsulin interaaction in tyhpe 1 diabetes mellitus, Med. Eng. Phys. 16:193-202.

Lerner et al. 1984. An implantable electrochemical glucose sensor. Ann. N. Y. Acad. Sci. 428:263-278.

Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.

Linke et al. 1994. Amperometric biosensor for in vivo glucose sensing based on glucose oxidase immobilized in a redox hydrogel. Biosensors & Bioelectronics 9:151-158.

Lohn et al., A knowledge-based system for real-time validation of calibrations and measurements, Chemometrics and Intelligent Laboratory Systems, 1999 46, 57-66.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lyandres et al. (2008). Progress toward an in vivo surface-enhanced raman spectroscopy glucose sensor. *Diabetes Technology & Therapeutics*, 10(4): 257-265.

Lynch et al. 2001. Estimation-based model predictive control of blood glucose in type I diabetics: A simulation study. Proceedings of the IEEE 27th Annual Northeast Bioengineering Conference, pp. 79-80.

Lynn, P. A. 1971. Recursive digital filters for biological signals. Med. & Biol. Engng. 9:37-43.

Maidan et al. 1992. Elimination of Electrooxidizable Interferent-Produced Currents in Amperometric Biosensors, Analytical Chemistry, 64:2889-2896.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

Mancy et al. 1962. A galvanic cell oxygen analyzer. Journal of Electroanalytical Chemistry 4:65-92.

Maran et al. 2002. Continuous subcutaneous glucose monitoring in diabetic patients: A multicenter analysis. Diabetes Care 25(2):347-352.

March, W. F. 2002. Dealing with the delay. Diabetes Technol Ther 4(1):49-50.

Marena et al. 1993. The artifical endocrine pancreas in clinical practice and research. Panminerva Medica 35(2):67-74.

Martin, R. F. 2000. General Deming regression for estimating systematic bias and its confidence interval in method-comparison studies. *Clinical Chemistry*, 46(1):100-104.

Mascini et al. 1989. Glucose electrochemical probe with extended linearity for whole blood. *J Pharm Biomed Anal* 7(12): 1507-1512.

Mastrototaro et al. "An electroenzymatic glucose sensor fabricated on a flexible substrate," Sensors and Actuators B, 5:139-44 (1991).

Mastrototaro, J. J. 2000. The MiniMed continuous glucose monitoring system. Diabetes Technol Ther 2(Suppl 1):S13-8.

Mastrototaro et al. 2003. Reproducibility of the continuous glucose monitoring system matches previous reports and the intended use of the product. Diabetes Care 26:256; author reply p. 257.

Matsuki. 1994. Energy transfer system utilizing amorphous wires for implantable medical devices. IEEE Transactions on Magnetics 31(2):1276-1282.

Matsumoto et al. 1998. A micro-planar amperometeric glucose sensor unsusceptible to interference species. Sensors and Actuators B 49:68-72.

Matthews et al. 1988. An amperometric needle-type glucose sensor testing in rats and man. Diabetic Medicine 5:248-252.

Mazze et al. 2008. Characterizing glucose exposure for individuals with normal glucose tolerance using continuous glucose monitoring and ambulatory glucose profile analysis. Diab. Thechnol. & Therapeut., 10:149-159.

Mazzola et al., Video Diabetes: A Teaching Tool for Children with Insulin-Dependent Diabetes, Proceedings—7th Annual Symposium on Computer Applications in Medical Care; Washington, D.C.; Dialog:, (Oct. 1983), File 8, Acc# 01624462.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

McKean et al. Jul. 7, 1988. A Telemetry Instrumentation System for Chronically Implanted Glucose and Oxygen Sensors. Transactions on Biomedical Engineering 35:526-532.

Memoli et al. 2002. A comparison between different immobilised glucoseoxidase-based electrodes. J Pharm Biomed Anal 29:1045-1052.

Merriam-Webster Online Dictionary. Definition of "acceleration". http://www.merriam-webster.com/dictionary/Acceleration Jan. 11, 2010.

Merriam-Webster Online Dictionary. Definition of "system". http://www.merriam-webster.com/dictionary/System Jan. 11, 2010.

Merriam-Webster Online Dictionary. The term "nominal." http://www.m-w.com/dictionary/nominal.

Metzger et al. Jul. 2002. Reproducibility of glucose measurements using the glucose sensor. Diabetes Care 25(6):1185-1191.

Meyerhoff et al. 1992. On line continuous monitoring of subcutaneous tissue glucose in men by combining portable glucosensor with microdialysis. Diabetologia 35:1087-1092.

Miller et al. 1993. Development of an autotuned transcutaneous energy transfer system ASAIO Journal 39:M706-M710.

Moatti-Sirat et al. 1992. Evaluating in vitro and in vivo the interference of ascorbate and acetaminophen on glucose detection by a needle-type glucose sensor, Biosensors & Bioelectronics 7:345-352.

Moatti-Sirat et al. 1992. Towards continuous glucose monitoring: in vivo evaluation of a miniaturized glucose sensor implanted for several days in rat subcutaneous tissue. Diabetologia 35:224-230.

Moatti-Sirat et al., Reduction of acetaminophen interference in glucose sensors by a composite Nafion membrane: demonstration in rats and man, Diabetologia 37(6):610-616, Jun. 1994.

Monsod et al. 2002. Do sensor glucose levels accurately predict plasma glucose concentrations during hypoglycemia and hyperinsulinemia? Diabetes Care 25(5):889-893.

Morff et al. 1990. Microfabrication of reproducible, economical, electroenzymatic glucose sensors, Annual International Conference of the IEEE Engineering in Medicine and Biology Society, 12(2):0483-0484.

Mosbach et al. 1975. Determination of heat changes in the proximity of immobilized enzymes with an enzyme termistor and its use for the assay of metabolites, Biochim. Biophys. Acta. (Enzymology), 403:256-265.

Motonaka et al. 1993. Determination of cholesteral and cholesteral ester with novel enzyme microsensors, Anal. Chem. 65:3258-3261.

Moussy et al. 1994. A miniaturized Nafion-based glucose sensor: In vitro and in vivo evaluation in dogs. Int. J. Artif. Organs 17(2):88-94.

Murphy, et al. 1992. Polymer membranes in clinical sensor applications. II. The design and fabrication of permselective hydrogels for electrochemical devices, Biomaterials, 13(14):979-990.

Muslu. 1991. Trickling filter performance. Apllied Biochemistry and Biotechnology 37:211-224.

Nafion® 117 Solution Product Description, Product No. 70160, Sigma-Aldrich Corp., St. Louis, MO.

Neuburger et al. 1987. Pulsed amperometric detection of carbohydrates at gold electrodes with a two-step potential waveform. Anal. Chem. 59:150-154.

Nintendo Healthcare, Wired, Dec. 1993.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

Ohara et al. 1994. "Wired" enzyme electrodes for amperometric determination of glucose or lactate in the presence of interfering substances. Anal Chem 66:2451-2457.

Okuda et al. 1971. Mutarotase effect on micro determinations of D-glucose and its anomers with β-D-glucose oxidase. Anal Biochem 43:312-315.

Oxford English Dictionary Online. Definition of "impending". http://www.askoxford.com/results/?view=dev dict&field-12668446 Impending&branch= Jan. 11, 2010.

Palmisano et al. 2000. Simultaneous monitoring of glucose and lactate by an interference and cross-talk free dual electrode amperometric biosensor based on electropolymerized thin films. Biosensors & Bioelectronics 15:531-539.

Panteleon et al. 2003. The role of the independent variable to glucose sensor calibration. Diabetes Technology & Therapeutics 5(3):401-410.

Parker et al. 1999. A model-based algorithm for blood glucose control in type I diabetic patients. IEEE Trans. Biomed. Eng. 46(2):148-157.

Patel et al. 2003. Amperometric glucose sensors based on ferrocene containing polymeric electron transfer systems-a preliminary report. Biosens Bioelectron 18:1073-6.

Peacock et al. 2008. Cardiac troponin and outcome in acute heart failure. N. Engl. J. Med., 358: 2117-2126.

Pfeiffer, E.F. 1990. The glucose sensor: the missing link in diabetes therapy, Horm Metab Res Suppl. 24:154-164.

Pfeiffer et al. 1992. On line continuous monitoring of subcutaneous tissue glucose is feasible by combining portable glucosensor with microdialysis. Horm. Metab. Res. 25:121-124.

Philips. 1995. A high capacity transcutaneous energy transmission system. ASAIO Journal 41:M259-M262.

Pichert et al. 2000. Issues for the coming age of continuous glucose monitoring Diabetes Educ 26(6):969-980.

Pickup et al. "Implantable glucose sensors: choosing the appropriate sensing strategy," Biosensors, 3:335-346 (1987/88).

Pickup et al. "In vivo molecular sensing in diabetes mellitus: an implantable glucose sensor with direct electron transfer," Diabetologia, 32:213-217 (1989).

Pickup et al. 1989. Potentially-implantable, amperometric glucose sensors with mediated electron transfer: improving the operating stability. Biosensors 4:109-119.

Pickup et al. 1993. Responses and Calibration of Amperometric Glucose Sensors Implanted in the Subcutaneous Tissue of Man. ACTA Diabetol, pp. 143-148.

Pickup et al. 1993. Developing glucose sensors for in vivo use. Elsevier Science Publishers Ltd (UK), TIBTECH vol. 11: 285-291.

Pinner et al., Cross-linking of cellulose acetate by ionizing radiation, Nature, vol. 184, 1303-1304, Oct. 24, 1959.

Pishko et al. "Amperometric glucose microelectrodes prepared through immobilization of glucose oxidase in redox hydrogels," Anal. Chem., 63:2268-72 (1991).

Pitzer et al. 2001. Detection of hypoglycemia with the GlucoWatch biographer. Diabetes Care 24(5):881-885.

Poirier et al. 1998. Clinical and statistical evaluation of self-monitoring blood glucose meters. Diabetes Care 21(11):1919-1924.

Poitout, et al. 1991. In Vitro and in Vivo Evaluation in Dogs of a Miniaturized Glucose Sensor, ASAIO Transactions, 37:M298-M300.

Poitout et al. 1993. A glucose monitoring system for on line estimation in man of blood glucose concentration using a miniaturized glucose sensor implanted in the subcutaneous tissue and a wearable control unit. Diabetologia 36:658-663.

Poitout et al. 1994. Development of a glucose sensor for glucose monitoring in man: the disposable implant concept. Clinical Materials 15:241-246.

Postlethwaite et al. 1996. Interdigitated array electrode as an alternative to the rotated ring-disk electrode for determination of the reaction products of dioxygen reduction. Analytical Chemistry 68:2951-2958.

Prabhu et al. 1981. Electrochemical studies of hydrogen peroxide at a platinum disc electrode, Electrochimica Acta 26(6):725-729.

Quinn et al. 1995. Kinetics of glucose delivery to subcutaneous tissue in rats measured with 0.3-mm amperometric microsensors. The American Physiological Society E155-E161.

Quinn et al. 1997. Biocompatible, glucose-permeable hydrogel for in situ coating of implantable biosensors. Biomaterials 18:1665-1670.

Rabah et al., 1991. Electrochemical wear of graphite anodes during electrolysis of brine, Carbon, 29(2):165-171.

Raya Systems Pioneers Healthy Video Games, PlayRight, Nov. 1993 (pp. 14-15).

Reach et al. 1986. A Method for Evaluating in vivo the Functional Characteristics of Glucose Sensors. Biosensors 2:211-220.

Reach et al. 1992. Can continuous glucose monitoring be used for the treatment of diabetes? Analytical Chemistry 64(5):381-386.

Reach, G. 2001. Which threshold to detect hypoglycemia? Value of receiver-operator curve analysis to find a compromise between sensitivity and specificity. Diabetes Care 24(5):803-804.

Reach, Gerard. 2001. Letters to the Editor Re: Diabetes Technology & Therapeutics, 2000;2:49-56. Diabetes Technology & Therapeutics 3(1):129-130.

Rebrin et al. "Automated feedback control of subcutaneous glucose concentration in diabetic dogs," Diabetologia, 32:573-76 (1989).

Rebrin et al. 1992. Subcutaneous glucose monitoring by means of electrochemical sensors: fiction or reality? J. Biomed. Eng. 14:33-40.

Rebrin et al. 1999. Subcutaneous glucose predicts plasma glucose independent of insulin: Implications for continuous monitoring. Am. J. Physiol. 277:E561-71.

Reusch. 2004. Chemical Reactivity. Organometallic Compounds. Virtual Textbook of Organic Chem. pp. 1-16, http://www.cem.msu.edu/~reusch/VirtualText/orgmetal.htm.

Rhodes et al. 1994. Prediction of pocket-portable and implantable glucose enzyme electrode performance from combined species permeability and digital simulation analysis. Analytical Chemistry 66(9):1520-1529.

Rigla et al. 2008. Real-time continuous glucose monitoring together with telemedical assitance improves glycemic control and glucose stability in pump-treated patients. Diab. Thechnol. & Therapeut., 10:194-199.

Rinken et al. 1998. Calibration of glucose biosensors by using pre-steady state kinetic data. Biosensors & Bioelectronics, 13:801-807.

Rivers et al., Central venous oxygen saturation monitoring in the critically ill patient, Current Opinion in Critical Care, 7:204-211, 2001.

Sakakida et al. 1992. Development of Ferrocene-Mediated Needle-Type Glucose Sensor as a Measure of True Subcutaneous Tissue Glucose Concentrations. Artif. Organs Today 2(2):145-158.

Sakakida et al. 1993. Ferrocene-Mediated Needle Type Glucose Sensor Covered with Newly Designed Biocompatible Membran, Sensors and Actuators B 13-14:319-322.

Salardi et al. 2002. The glucose area under the profiles obtained with continuous glucose monitoring system relationships with HbA1c in pediatric type 1 diabetic patients. Diabetes Care 25(10):1840-1844.

San Diego Plastics, Inc. 2009. Polyethylene Data Sheet, http://www.sdplastics.com/polyeth.html.

Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.

Sansen et al. 1990. A smart sensor for the voltammetric measurement of oxygen or glucose concentrations. Sensors and Actuators B 1:298-302.

Schmidt et al. 1992. Calibration of a wearable glucose sensor. The International Journal of Artificial Organs 15(1):55-61.

Schmidt et al. 1993. Glucose concentration in subcutaneous extracellular space. Diabetes Care 16(5):695-700.

Schmidtke et al. 1998. Accuracy of the one-point in vivo calibration of "wired" glucose oxidase electrodes implanted in jugular veins of rats in periods of rapid rise and decline of the glucose concentration. Anal Chem 70:2149-2155.

Schmidtke et al., Measurement and modeling of the transient difference between blood and subcutaneous glucose concentrations in the rat after injection of insulin. *Proc Natl Aced Sci U S A* 1998, 95, 294-299.

Schoemaker et al. 2003. The SCGM1 system: Subcutaneous continuous glucose monitoring based on microdialysis technique. Diabetes Technology & Therapeutics 5(4):599-608.

Schoonen et al. 1990 Development of a potentially wearable glucose sensor for patients with diabetes mellitus: design and in-vitro evaluation. Biosensors & Bioelectronics 5:37-46.

Service et al. 1970. Mean amplitude of glycemic excursions, a measure of diabetic instability. Diabetes, 19: 644-655.

Service et al. 1987. Measurements of glucose control. Diabetes Care, 10: 225-237.

Service, R. F. 2002. Can sensors make a home in the body? Science 297:962-3.

Sharkawy et al. 1996. Engineering the tissue which encapsulates subcutaneous implants. I. Diffusion properties, J Biomed Mater Res, 37:401-412.

Shaw et al. "In vitro testing of a simply constructed, highly stable glucose sensor suitable for implantation in diabetic patients," Biosensors & Bioelectronics, 6:401-406 (1991).

Shichiri et al. 1982. Wearable artificial endocrine pancrease with needle-type glucose sensor. Lancet 2:1129-1131.

Shichiri et al. 1983. Glycaemic Control in Pancreatectomized Dogs with a Wearable Artificial Endocrine Pancreas. Diabetologia 24:179-184.

Shichiri et al. 1985. Needle-type Glucose Sensor for Wearable Artificial Endocrine Pancreas in Implantable Sensors 197-210.

Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.

Shichiri et al. 1989. Membrane Design for Extending the Long-Life of an Implantable Glucose Sensor. Diab. Nutr. Metab. 2:309-313.

Shults et al. 1994. A telemetry-instrumentation system for monitoring multiple subcutaneously implanted glucose sensors. IEEE Transactions on Biomedical Engineering 41(10):937-942.

Skyler, J. S. 2000. The economic burden of diabetes and the benefits of improved glycemic control: The potential role of a continuous glucose monitoring system. Diabetes Technology & Therapeutics 2 Suppl 1:S7-12.

Slater-Maclean et al. 2008. Accuracy of glycemic measurements in the critically ill. Diab. Thechnol. & Therapeut., 10:169-177.

Smith et al. 1998. An externally powered, multichannel, implantable stimulator-telemeter for control of paralyzed muscle. IEEE Transactions on Biomedical Engineering 45(4):463-475.

Sokol et al. 1980, Immobilized-enzyme rate-determination method for glucose analysis, Clin. Chem. 26(1):89-92.

Sokolov et al. 1995. Metrological opportunities of the dynamic mode of operating an enzyme amperometric biosensor. Med. Eng. Phys. 17(6):471-476.

Sparacino et al., 2008. Continuous glucose monitoring time series and hypo/hyperglycemia prevention: requirements, methods, open problems, Current Diabetes Reviews, 4:181-192.

Sproule et al. 2002. Fuzzy pharmacology: Theory and applications. Trends in Pharmacological Sciences, 23(9):412-417.

Sriyudthsak et al. 1996. Enzyme-epoxy membrane based glucose analyzing system and medical applications. Biosens Bioelectron 11:735-742.

Steil et al. 2003. Determination of plasma glucose during rapid glucose excursions with a subcutaneous glucose sensor. Diabetes Technology & Therapeutics 5(1):27-31.

Stern et al., 1957. Electrochemical polarization: 1. A theoretical analysis of the shape of polarization curves, Journal of the Electrochemical Society, 104(1):56-63.

Sternberg et al. 1988. Study and Development of Multilayer Needle-type Enzyme-based Glucose Microsensors. Biosensors 4:27-40.

Sternberg et al. 1996. Does fall in tissue glucose precede fall in blood glucose? Diabetologia 39:609-612.

Street et al. 1988. A note on computing robust regression estimates via iteratively reweighted least squares. The American Statistician 42(2):152-154.

Sumino T. et al. 1998. Preliminary study of continuous glucose monitoring with a microdialysis technique. Proceedings of the IEEE, 20(4):1775-1778.

Takegami et al. 1992. Pervaporation of ethanol water mixtures using novel hydrophobic membranes containing polydimethylsiloxane, Journal of Membrane Science, 75(93-105).

Tamura, T. et al. 2000. Preliminary study of continuous glucose monitoring with a microdialysis technique and a null method—a numerical analysis. Frontiers Med. Biol. Engng. 10(2):147-156.

Tanenberg et al. 2000. Continuous glucose monitoring system: A new approach to the diagnosis of diabetic gastroparesis. Diabetes Technology & Therapeutics, 2 Suppl 1:S73-80.

Tatsuma et al. 1991. Oxidase/peroxidase bilayer-modified electrodes as sensors for lactate, pyruvate, cholesteral and uric acid, Analytica Chimica Acta, 242:85-89.

Thome et al. 1995. -Abstract—Can the decrease in subcutaneous glucose concentration precede the decrease in blood glucose level? Proposition for a push-pull kinetics hypothesis, Horm. Metab. Res. 27:53.

Thomé-Duret et al. 1996. Modification of the sensitivity of glucose sensor implanted into subcutaneous tissue. Diabetes Metabolism, 22:174-178.

Thome-Duret et al. 1996. Use of a subcutaneous glucose sensor to detect decreases in glucose concentration prior to observation in blood, Anal. Chem. 68:3822-3826.

Thomé-Duret et al. 1998. Continuous glucose monitoring in the free-moving rat. Metabolism, 47:799-803.

Thompson et al., In Vivo Probes: Problems and Perspectives, Department of Chemistry, University of Toronto, Canada, pp. 255-261, 1986.

Tierney et al. 2000. Effect of acetaminophen on the accuracy of glucose measurements obtained with the GlucoWatch biographer. Diabetes Technol Ther 2:199-207.

Tierney et al. 2000. The GlucoWatch® biographer: A frequent, automatic and noninvasive glucose monitor. Ann. Med. 32:632-641.

Tilbury et al. 2000. Receiver operating characteristic analysis for intelligent medical systems—A new approach for finding confidence intervals. IEEE Transactions on Biomedical Engineering 47(7):952-963.

Torjman et al., Glucose monitoring in acute care: technologies on the horizon, Journal of Deabetes Science and Technology, 2(2):178-181, Mar. 2008.

Trajanoski et al. 1998. Neural predictive controller for insulin delivery using the subcutaneous route. IEEE Transactions on Biomedical Engineering 45(9):1122-1134.

Trecroci, D. 2002. A Glimpse into the Future—Continuous Monitoring of Glucose with a Microfiber. Diabetes Interview 42-43.

Tse and Gough. 1987. Time-Dependent Inactivation of Immobilized Glucose Oxidase and Catalase. Biotechnol. Bioeng. 29:705-713.

Turner and Pickup, "Diabetes mellitus: biosensors for research and management," *Biosensors*, 1:85-115 (1985).

Turner et al. 1984. Carbon Monoxide: Acceptor Oxidoreductase from *Pseudomonas Thermocarboxydovorans* Strain C2 and its use in a Carbon Monoxide Sensor. Analytica Chimica Acta, 163: 161-174.

Unger et al. 2004. Glucose control in the hospitalized patient. Emerg Med 36(9):12-18.

Updike et al. 1967. The enzyme electrode. Nature, 214:986-988.

Updike et al. 1979. Continuous glucose monitor based on an immobilized enzyme electrode detector. J Lab Clin Med, 93(4):518-527.

Updike et al. 1982. Implanting the glucose enzyme electrode: Problems, progress, and alternative solutions. Diabetes Care, 5(3):207-212.

Updike et al. 1988. Laboratory Evaluation of New Reusable Blood Glucose Sensor. Diabetes Care, 11:801-807.

Updike et al. 1994. Enzymatic glucose sensor: Improved long-term performance in vitro and in vivo. ASAIO Journal, 40(2):157-163.

Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons.

Updike et al. 2000. A subcutaneous glucose sensor with improved longevity, dynamic range, and stability of calibration. Diabetes Care 23(2):208-214.

Utah Medical Products Inc., Blood Pressure Tranducers product specifications. 6 pp. 2003-2006, 2003.

Vadgama, P. Nov. 1981. Enzyme electrodes as practical biosensors. Journal of Medical Engineering & Technology 5(6):293-298.

Vadgama. 1988. Diffusion limited enzyme electrodes. NATO ASI Series: Series C, Math and Phys. Sci. 226:359-377.

Valdes et al. 2000. In vitro and in vivo degradation of glucose oxidase enzyme used for an implantable glucose biosensor. Diabetes Technol. Ther. 2:367-376.

Van den Berghe 2004. Tight blood glucose control with insulin in "real-life" intensive care. Mayo Clin Proc 79(8):977-978.

Velho et al. 1989. In vitro and in vivo stability of electrode potentials in needle-type glucose sensors. Influence of needle material. Diabetes 38:164-171.

Velho et al. 1989. Strategies for calibrating a subcutaneous glucose sensor. Biomed Biochim Acta 48(11/12):957-964.

von Woedtke et al. 1989. In situ calibration of implanted electrochemical glucose sensors. Biomed Biochim Acta 48(11/12):943-952.

Wagner et al. 1998. Continuous amperometric monitoring of glucose in a brittle diabetic chimpanzee with a miniature subcutaneous electrode. Proc. Natl. Acad. Sci. A, 95:6379-6382.

Wang et al. 1994. Highly Selective Membrane-Free, Mediator-Free Glucose Biosensor. Anal. Chem. 66:3600-3603.

Wang et al. 1997. Improved ruggedness for membrane-based amperometric sensors using a pulsed amperometric method. Anal Chem 69:4482-4489.

Ward et al. 1999. Assessment of chronically implanted subcutaneous glucose sensors in dogs: The effect of surrounding fluid masses. ASAIO Journal, 45:555-561.

Ward et al. 2000. Understanding Spontaneous Output Fluctuations of an Amperometric Glucose Sensor: Effect of Inhalation Anesthesia and use of a Nonenzyme Containing Electrode. ASAIO Journal 540-546.

Ward et al. 2000. Rise in background current over time in a subcutaneous glucose sensor in the rabbit: Relevance to calibration and accuracy. Biosensors & Bioelectronics, 15:53-61.

Ward et al. 2002. A new amperometric glucose microsensor: in vitro and short-term in vivo evaluation. Biosensors & Bioelectronics, 17:181-189.

Wientjes, K. J. C. 2000. Development of a glucose sensor for diabetic patients (Ph.D. Thesis).

Wikipedia 2006. "Intravenous therapy," http://en.wikipedia.org/wiki/Intravenous_therapy, Aug. 15, 2006, 6 pp.

Wiley Electrical and Electronics Engineering Dictionary. 2004. John Wiley & Sons, Inc. pp. 141, 142, 548, 549.

Wilkins et al. 1988. The coated wire electrode glucose sensor, Horm Metab Res Suppl., 20:50-55.

Wilkins et al. 1995. Glucose monitoring: state of the art and future possibilities. Med Eng Phys 18:273-288.

Wilkins et al. 1995. Integrated implantable device for long-term glucose monitoring. Biosens. Bioelectron 10:485-494.

Wilson et al. 1992. Progress toward the development of an implantable sensor for glucose. Clin. Chem. 38(9):1613-1617.

Wilson et al. 2000. Enzyme-based biosensors for in vivo measurements. Chem. Rev., 100:2693-2704.

Wood, W. et al. Mar. 1990. Hermetic Sealing with Epoxy. Mechanical Engineering 1-3.

Woodward. 1982. How Fibroblasts and Giant Cells Encapsulate Implants: Considerations in Design of Glucose Sensor. Diabetes Care 5:278-281.

Worsley et al., Measurement of glucose in blood with a phenylboronic acid optical sensor, Journal of Diabetes Science and Technology, 2(2):213-220, Mar. 2008.

Wright et al., Bioelectrochemical dehalogenations via direct electrochemistry of poly(ethylene oxide)-modified myoglobin, Electrochemistry Communications 1 (1999) 603-611.

Wu et al. 1999. In situ electrochemical oxygen generation with an immunoisolation device. Annals New York Academy of Sciences, pp. 105-125.

Yamasaki, Yoshimitsu. Sep. 1984. The development of a needle-type glucose sensor for wearable artificial endocrine pancreas. Medical Journal of Osaka University 35(1-2):25-34.

Yamasaki et al. 1989. Direct measurement of whole blood glucose by a needle-type sensor. Clinica Chimica Acta. 93:93-98.

Yang et al (1996). "A glucose biosensor based on an oxygen electrode: In-vitro performances in a model buffer solution and in blood plasma," Biomedical Instrumentation & Technology, 30:55-61.

Yang et al. 1998. Development of needle-type glucose sensor with high selectivity. Science and Actuators B 46:249-256.

Yang, et al. 2004. A Comparison of Physical Properties and Fuel Cell Performance of Nafion and Zirconium Phosphate/Nafion Composite Membranes. Journal of Membrane Science 237:145-161.

Ye et al. 1993. High Current Density 'Wired' Quinoprotein Glucose Dehydrogenase Electrode. Anal. Chem. 65:238-241.

Zamzow et al. 1990. Development and evaluation of a wearable blood glucose monitor, ASAIO Transactions; 36(3): pp. M588-M591.

Zavalkoff et al. 2002. Evaluation of conventional blood glucose monitoring as an indicator of integrated glucose values using a continuous subcutaneous sensor. Diabetes Care 25(9):1603-1606.

Zethelius et al. 2008. Use of multiple biomarkers to improve the prediction of death from cardiovascular causes. N. Engl. J. Med., 358: 2107-2116.

Zhang et al (1993). Electrochemical oxidation of $H_2O_2$ on Pt and Pt + Ir electrodes in physiological buffer and its applicability to $H_2O_2$-based biosensors. *J. Electroanal. Chem.*, 345:253-271.

Zhang et al. 1993. In vitro and in vivo evaluation of oxygen effects on a glucose oxidase based implantable glucose sensor. Analytica Chimica Acta, 281:513-520.

Zhang et al. 1994. Elimination of the acetaminophen interference in an implantable glucose sensor. Analytical Chemistry 66(7):1183-1188.

Zhu et al. (1994). "Fabrication and characterization of glucose sensors based on a microarray $H_2O_2$ electrode." *Biosensors & Bioelectronics*, 9: 295-300.

Zhu et al. 2002 Planar amperometric glucose sensor based on glucose oxidase immobilized by chitosan film on prussian blue layer. Sensors, 2:127-136.

Ziaie et al. 1997. A single-channel implantable microstimulator for functional neuromuscular stimulation. IEEE Transactions on Biomedical Engineering 44(10):909-920.

EPO Search Report dated Apr. 7, 2011 for Application No. 08770744.4, filed Jun. 11, 2008.

ISR and WO for PCT/US06/34284, filed Sep. 1, 2006.

IPRP for PCT/US06/34284, filed Sep. 1, 2006.

ISR and WO dated Oct. 7, 2008 for PCT/US08/66600, filed Jun. 11, 2008.

IPRP dated Dec. 17, 2009 for PCT/US08/66600, filed Jun. 11, 2008.

Office Action dated Sep. 30, 2002 in U.S. Appl. No. 09/636,369.
Office Action dated Jul. 15, 2008 in U.S. Appl. No. 10/633,367.
Office Action dated Jun. 11, 2009 in U.S. Appl. No. 10/633,367.
Office Action dated Jul. 30, 2009 in U.S. Appl. No. 12/102,654.
Office Action dated Mar. 10, 2010 in U.S. Appl. No. 12/102,654.
Office Action dated Dec. 23, 2008 in U.S. Appl. No. 12/102,745.
Office Action dated Oct. 20, 2004 in U.S. Appl. No. 10/632,537.
Office Action dated Dec. 21, 2004 in U.S. Appl. No. 10/632,537.
Office Action dated May 29, 2008 in U.S. Reexam No. 95/001,039.
Office Action dated May 19, 2009 in U.S. Appl. No. 11/038,340.
Office Action dated Nov. 9, 2009 in U.S. Appl. No. 11/038,340.
Office Action dated Jun. 17, 2008 in U.S. Appl. No. 11/038,340.
Office Action dated Jan. 5, 2009 in U.S. Appl. No. 11/038,340.
Office Action dated Feb. 12, 2007 in U.S. Appl. No. 10/633,404.
Office Action dated Jun. 17, 2008 in U.S. Reexam No. 95/001,038.
Office Action dated Dec. 18, 2008 in U.S. Appl. No. 10/633,329.
Office Action dated Apr. 27, 2010 in U.S. Appl. No. 10/633,329.
Office Action dated Jun. 23, 2009 in U.S. Appl. No. 10/648,849.
Office Action dated Jun. 24, 2008 n. U.S. Appl. No. 11/007,920.
Office Action dated Nov. 28, 2007 in U.S. Appl. No. 10/991,966.
Office Action dated Jul. 22, 2008 in U.S. Appl. No. 10/991,966.
Office Action dated Nov. 27, 2006 in U.S. Appl. No. 10/789,359.
Office Action dated Mar. 20, 2008 in U.S. Appl. No. 10/789,359.
Office Action dated Oct. 3, 2008 in U.S. Appl. No. 10/789,359.
Office Action mailed Jun. 5, 2008 in U.S. Appl. No. 10/838,909.
Office Action mailed Mar. 16, 2009 in U.S. Appl. No. 10/838,909.
Office Action dated Mar. 31, 2008 in U.S. Appl. No. 11/077,759.
Office Action dated Jul. 10, 2008 in U.S. Appl. No. 11/077,759.
Office Action dated May 26, 2009 in U.S. Appl. No. 11/077,759.
Office Action dated Jul. 21, 2009 in U.S. Appl. 11/077,739.
Office Action dated Dec. 29, 2009 in U.S. Appl. 11/077,739.
Office Action dated Mar. 1, 2010 in U.S. Appl. 11/077,739.
Office Action dated Jun. 1, 2007 in U.S. Appl. No. 11/077,740.
Office Action dated Nov. 1, 2007 in U.S. Appl. No. 11/077,740.
Office Action dated Feb. 7, 2008 in U.S. Appl. No. 11/077,740.
Office Action dated Jul. 25, 2008 in U.S. Appl. No. 11/077,740.
Office Action dated Apr. 28, 2009 in U.S. Appl. No. 11/077,740.
Office Action dated Dec. 31, 2007 in U.S. Appl. No. 11/077,765.
Office Action dated May 16, 2008 in U.S. Appl. No. 11/077,765.
Office Action dated Sep. 19, 2008 in U.S. Appl. No. 11/077,765.
Office Action dated Jan. 23, 2009 in U.S. Appl. No. 11/077,765.
Office Action dated Feb. 3, 2010 in U.S. Appl. No. 11/077,765.
Office Action dated Jun. 26, 2008 in U.S. Appl. No. 11/157,365.
Office Action dated Jan. 7, 2009 in U.S. Appl. No. 11/157,365.
Office Action dated Jul. 21, 2009 in U.S. Appl. No. 11/157,365.
Office Action dated Jan. 21, 2010 in U.S. Appl. No. 11/157,365.
Office Action dated Oct. 4, 2006 in U.S. Appl. No. 11/334,876.
Office Action dated Sep. 25, 2007 in U.S. Appl. No. 11/334,876.
Office Action dated May 2, 2008 in U.S. Appl. No. 11/334,876.
Office Action dated Aug. 26, 2008 in U.S. Appl. No. 11/334,876.
Office Action dated Aug. 25, 2009 in U.S. Appl. No. 11/334,876.
Office Action dated Jun. 30, 2008 in U.S. Appl. No. 11/360,252.
Office Action dated Jan. 29, 2009, in U.S. Appl. No. 11/360,252.
Office Action dated Jul. 23, 2009, in U.S. Appl. No. 11/360,252.
Office Action dated Aug. 11, 2008 in U.S. Appl. No. 11/360,819.
Office Action dated Dec. 26, 2008 in U.S. Appl. No. 11/360,819.
Office Action dated Oct. 29, 2009 in U.S. Appl. No. 11/360,819.
Office Action dated Apr. 7, 2010 in U.S. Appl. No. 11/360,819.

Merriam-Webster Online Dictionary. Apr. 23, 2007. Definition of "nominal". http://www.merriam-webstercom/dictionary/nominal [corrected cite].

Nafion® 117 Solution Product Description, Product No. 70160, Sigma-Aldrich Corp., St. Louis, MO. Downloaded from https://www.signaaldrich.com/cgi-bin/hsrun/Suite7/Suite/HAHTpage/Suite.HsExternalProd... on Apr. 7, 2005. [corrected cite].

US 7,530,950, 05/2009, Brister et al. (withdrawn)

* cited by examiner

SYSTEMS AND METHODS FOR REPLACING SIGNAL ARTIFACTS IN A GLUCOSE SENSOR DATA STREAM

CROSS-REFERENCE TO RELATED APPLICATIONS

This application is a divisional of U.S. application Ser. No. 12/353,799 filed Jan. 14, 2009, which is a divisional of U.S. application Ser. No. 10/648,849 filed Aug. 22, 2003, the specifications of which are incorporated by reference herein in their entirety, and are hereby made a part of this specification.

FIELD OF THE INVENTION

The present invention relates generally to systems and methods for processing data received from a glucose sensor. Particularly, the present invention relates to systems and methods for detecting and replacing transient non-glucose related signal artifacts, including detecting, estimating, predicting and otherwise minimizing the effects of signal artifacts in a glucose sensor data stream.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) is induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are so far spread apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if their blood glucose value is going up (higher) or down (lower) based on conventional methods.

Consequently, a variety of transdermal and implantable electrochemical sensors are being developed for continuous detecting and/or quantifying blood glucose values. Many implantable glucose sensors suffer from complications within the body and provide only short-term and less-than-accurate sensing of blood glucose. Similarly, transdermal sensors have run into problems in accurately sensing and reporting back glucose values continuously over extended periods of time. Some efforts have been made to obtain blood glucose data from implantable devices and retrospectively determine blood glucose trends for analysis, however these efforts do not aid the diabetic in determining real-time blood glucose information. Some efforts have also been made to obtain blood glucose data from transdermal devices for prospective data analysis, however similar problems have occurred.

Data streams from glucose sensors are known to have some amount of noise, caused by unwanted electronic and/or diffusion-related system noise that degrades the quality of the data stream. Some attempts have been made in conventional glucose sensors to smooth the raw output data stream representative of the concentration of blood glucose in the sample, for example by smoothing or filtering of Gaussian, white, random, and/or other relatively low amplitude noise in order to improve the signal to noise ratio, and thus data output.

SUMMARY OF THE INVENTION

Systems and methods are provided that accurately detect and replace signal noise that is caused by substantially non-glucose reaction rate-limiting phenomena, such as ischemia, pH changes, temperature changes, pressure, and stress, for example, which are referred to herein as signal artifacts. Detecting and replacing signal artifacts in a raw glucose data can provide accurate estimated glucose measurements to a diabetic patient so that they can proactively care for their condition to safely avoid hyperglycemic and hypoglycemic conditions.

In a first embodiment a method is provided for analyzing data from a glucose sensor, including: monitoring a data stream from the sensor; detecting transient non-glucose related signal artifacts in the data stream that have a higher amplitude than a system noise; and replacing at least some of the signal artifacts using estimated glucose signal values.

In an aspect of the first embodiment, the data signal obtaining step includes receiving data from one of non-invasive, minimally invasive, and invasive glucose sensor.

In an aspect of the first embodiment, the data signal obtaining step includes receiving data from one of an enzymatic, chemical, physical, electrochemical, spectrophotometric, polarimetric, calorimetric, iontophoretic, and radiometric glucose sensor.

In an aspect of the first embodiment, the data signal obtaining step includes receiving data from a wholly implantable glucose sensor.

In an aspect of the first embodiment, the signal artifacts detection step includes testing for ischemia within or proximal to the glucose sensor.

In an aspect of the first embodiment, the ischemia testing step includes obtaining oxygen concentration using an oxygen sensor proximal to or within the glucose sensor.

In an aspect of the first embodiment, the ischemia testing step includes comparing a measurement from an oxygen sensor proximal to or within the glucose sensor with a measurement from an oxygen sensor distal from the glucose sensor.

In an aspect of the first embodiment, the glucose sensor includes an electrochemical cell including a working electrode and a reference electrode, and wherein the ischemia-testing step includes pulsed amperometric detection.

In an aspect of the first embodiment, the glucose sensor includes an electrochemical cell including working, counter and reference electrodes, and wherein the ischemia-testing step includes monitoring the counter electrode.

In an aspect of the first embodiment, the glucose sensor includes an electrochemical cell including working, counter and reference electrodes, and wherein the ischemia-testing step includes monitoring the reference electrode.

In an aspect of the first embodiment, the glucose sensor includes an electrochemical cell including an anode and a cathode, and wherein the ischemia-testing step includes monitoring the cathode.

In an aspect of the first embodiment, the signal artifacts detection step includes monitoring a level of pH proximal to the sensor.

In an aspect of the first embodiment, the signal artifacts detection step includes monitoring a temperature proximal to the sensor.

In an aspect of the first embodiment, the signal artifacts detection step includes comparing a level of pH proximal to and distal to the sensor.

In an aspect of the first embodiment, the signal artifacts detection step includes comparing a temperature proximal to and distal to the sensor.

In an aspect of the first embodiment, the signal artifacts detection step includes monitoring a pressure or stress within the glucose sensor.

In an aspect of the first embodiment, the signal artifacts detection step includes evaluating historical data for high amplitude noise above a predetermined threshold.

In an aspect of the first embodiment, the signal artifacts detection step includes a Cone of Possibility Detection Method.

In an aspect of the first embodiment, the signal artifacts detection step includes evaluating the data stream for a non-physiological rate-of-change.

In an aspect of the first embodiment, the signal artifacts detection step includes monitoring the frequency content of the signal.

In an aspect of the first embodiment, the frequency-content monitoring step includes performing an orthogonal basis function-based transform.

In an aspect of the first embodiment, the transform is a Fourier Transform or a wavelet transform.

In an aspect of the first embodiment, the artifacts replacement step includes performing linear or non-linear regression.

In an aspect of the first embodiment, the artifacts replacement step includes performing a trimmed mean.

In an aspect of the first embodiment, the artifacts replacement step includes filtering using a non-recursive filter.

In an aspect of the first embodiment, the non-recursive filtering step uses a finite impulse response filter.

In an aspect of the first embodiment, the artifacts replacement step includes filtering using a recursive filter.

In an aspect of the first embodiment, the recursive filtering step uses an infinite impulse response filter.

In an aspect of the first embodiment, the artifacts replacement step includes a performing a maximum average algorithm.

In an aspect of the first embodiment, the artifacts replacement step includes performing a Cone of Possibility Replacement Method.

In an aspect of the first embodiment, the method further includes estimating future glucose signal values based on historical glucose values.

In an aspect of the first embodiment, the glucose future estimation step includes algorithmically estimating the future signal value based using at least one of linear regression, non-linear regression, and an auto-regressive algorithm.

In an aspect of the first embodiment, the glucose future estimation step further includes measuring at least one of rate-of-change, acceleration, and physiologically feasibility of one or more signal values and subsequently selectively applying the algorithm conditional on a range of one of the measurements.

In an aspect of the first embodiment, the glucose sensor includes an electrochemical cell including working, counter, and reference electrodes, and wherein the artifacts replacement step includes normalizing the data signal based on baseline drift at the reference electrode.

In an aspect of the first embodiment, the signal artifacts replacement step is substantially continual.

In an aspect of the first embodiment, the signal artifacts replacement step is initiated in response to positive detection of signal artifacts.

In an aspect of the first embodiment, the signal artifacts replacement step is terminated in response to detection of negligible signal artifacts.

In an aspect of the first embodiment, the signal artifacts detection step includes evaluating the severity of the signal artifacts.

In an aspect of the first embodiment, the severity evaluation is based on an amplitude of the transient non-glucose related signal artifacts.

In an aspect of the first embodiment, the severity evaluation is based on a duration of the transient non-glucose related signal artifacts.

In an aspect of the first embodiment, the severity evaluation is based on a rate-of-change of the transient non-glucose related signal artifacts.

In an aspect of the first embodiment, the severity evaluation is based on a frequency content of the transient non-glucose related signal artifacts.

In an aspect of the first embodiment, the artifacts replacement step includes selectively applying one of a plurality of signal estimation algorithm factors in response to the severity of the signal artifacts.

In an aspect of the first embodiment, the plurality of signal estimation algorithm factors includes a single algorithm with a plurality of parameters that are selectively applied to the algorithm.

In an aspect of the first embodiment, the plurality of signal estimation algorithm factors includes a plurality of distinct algorithms.

In an aspect of the first embodiment, the step of selectively applying one of a plurality of signal estimation algorithm factors includes selectively applying a predetermined algorithm that includes a set of parameters whose values depend on the severity of the signal artifacts.

In an aspect of the first embodiment, the method further includes discarding at least some of the signal artifacts.

In an aspect of the first embodiment, the method further includes projecting glucose signal values for a time during which no data is available.

In a second embodiment, a method is provided for processing data signals obtained from a glucose sensor including: obtaining a data stream from a glucose sensor; detecting transient non-glucose related signal artifacts in the data stream that have a higher amplitude than a system noise; and selectively applying one of a plurality of signal estimation algorithm factors to replace non-glucose related signal artifacts.

In an aspect of the second embodiment, the data signal obtaining step includes receiving data from one of non-invasive, minimally invasive, and invasive glucose sensor.

In an aspect of the second embodiment, the data signal obtaining step includes receiving data from one of an enzymatic, chemical, physical, electrochemical, spectrophotometric, polarimetric, calorimetric, iontophoretic, and radiometric glucose sensor.

In an aspect of the second embodiment, the data signal obtaining step includes receiving data from a wholly implantable glucose sensor.

In an aspect of the second embodiment, the signal artifacts detection step includes testing for ischemia within or proximal to the glucose sensor.

In an aspect of the second embodiment, the ischemia testing step includes obtaining oxygen concentration using an oxygen sensor proximal to or within the glucose sensor.

In an aspect of the second embodiment, the ischemia testing step includes comparing a measurement from an oxygen sensor proximal to or within the glucose sensor with a measurement from an oxygen sensor distal from the glucose sensor.

In an aspect of the second embodiment, the glucose sensor includes an electrochemical cell including a working electrode and a reference electrode, and wherein the ischemia-testing step includes pulsed amperometric detection.

In an aspect of the second embodiment, the glucose sensor includes an electrochemical cell including working, counter and reference electrodes, and wherein the ischemia-testing step includes monitoring the counter electrode.

In an aspect of the second embodiment, the glucose sensor includes an electrochemical cell including working, counter and reference electrodes, and wherein the ischemia testing step includes monitoring the reference electrode.

In an aspect of the second embodiment, the glucose sensor includes an electrochemical cell including an anode and a cathode, and wherein the ischemia-testing step includes monitoring the cathode.

In an aspect of the second embodiment, the signal artifacts detection step includes monitoring a level of pH proximal to the sensor.

In an aspect of the second embodiment, the signal artifacts detection step includes monitoring a temperature proximal to the sensor.

In an aspect of the second embodiment, the signal artifacts detection step includes comparing a level of pH proximal to and distal to the sensor.

In an aspect of the second embodiment, the signal artifacts detection step includes comparing a temperature proximal to and distal to the sensor.

In an aspect of the second embodiment, the signal artifacts detection step includes monitoring the pressure or stress within the glucose sensor.

In an aspect of the second embodiment, the signal artifacts detection step includes evaluating historical data for high amplitude noise above a predetermined threshold.

In an aspect of the second embodiment, the signal artifacts detection step includes a Cone of Possibility Detection Method.

In an aspect of the second embodiment, the signal artifacts detection step includes evaluating the signal for a non-physiological rate-of-change.

In an aspect of the second embodiment, the signal artifacts detection step includes monitoring the frequency content of the signal.

In an aspect of the second embodiment, the frequency-content monitoring step includes performing an orthogonal basis function-based transform.

In an aspect of the second embodiment, the transform is a Fourier Transform or a wavelet transform.

In an aspect of the second embodiment, the artifacts replacement step includes performing linear or non-linear regression.

In an aspect of the second embodiment, the artifacts replacement step includes performing a trimmed mean.

In an aspect of the second embodiment, the artifacts replacement step includes filtering using a non-recursive filter.

In an aspect of the second embodiment, the non-recursive filtering step uses a finite impulse response filter.

In an aspect of the second embodiment, the artifacts replacement step includes filtering using a recursive filter.

In an aspect of the second embodiment, the recursive filtering step uses an infinite impulse response filter.

In an aspect of the second embodiment, the artifacts replacement step includes a performing a maximum average algorithm.

In an aspect of the second embodiment, the artifacts replacement step includes performing a Cone of Possibility algorithm.

In an aspect of the second embodiment, the method further includes estimating future glucose signal values based on historical glucose values.

In an aspect of the second embodiment, the glucose future estimation step includes algorithmically estimating the future signal value based using at least one of linear regression, non-linear regression, and an auto-regressive algorithm.

In an aspect of the second embodiment, the glucose future estimation step further includes measuring at least one of rate-of-change, acceleration, and physiologically feasibility of one or more signal values and subsequently selectively applying the algorithm conditional on a range of one of the measurements.

In an aspect of the second embodiment, the glucose sensor includes an electrochemical cell including working, counter, and reference electrodes, and wherein the artifacts replacement step includes normalizing the data signal based on baseline drift at the reference electrode.

In an aspect of the second embodiment, the selective application step is substantially continual.

In an aspect of the second embodiment, the selective application step is initiated in response to positive detection of signal artifacts.

In an aspect of the second embodiment, the selective application step is terminated in response to detection of negligible signal artifacts.

In an aspect of the second embodiment, the signal artifacts detection step includes evaluating the severity of the signal artifacts.

In an aspect of the second embodiment, the severity evaluation is based on an amplitude of the transient non-glucose related signal artifacts.

In an aspect of the second embodiment, the severity evaluation is based on a duration of the transient non-glucose related signal artifacts.

In an aspect of the second embodiment, the severity evaluation is based on a rate-of-change of the transient non-glucose related signal artifacts.

In an aspect of the second embodiment, the severity evaluation is based on a frequency content of the transient non-glucose related signal artifacts.

In an aspect of the second embodiment, the selective application step applies the one of a plurality of signal estimation algorithm factors in response to the severity of the signal artifacts.

In an aspect of the second embodiment, the plurality of signal estimation algorithm factors includes a single algorithm with a plurality of parameters that are selectively applied to the algorithm.

In an aspect of the second embodiment, the plurality of signal estimation algorithm factors includes a plurality of distinct algorithms.

In an aspect of the second embodiment, the selective application step includes selectively applying a predetermined algorithm that includes a set of parameters whose values depend on the severity of the signal artifacts.

In an aspect of the second embodiment, the method further includes discarding at least some of the signal artifacts.

In an aspect of the second embodiment, the selective application step further includes projecting glucose signal values for a time during which no data is available.

In a third embodiment, a system is provided for processing data signals obtained from a glucose sensor, including: a signal processing module including programming to monitor a data stream from the sensor over a period of time; a detection module including programming to detect transient non-glucose related signal artifacts in the data stream that have a higher amplitude than a system noise; and a signal estimation module including programming to replace at least some of the signal artifacts with estimated glucose signal values.

In an aspect of the third embodiment, the signal processing module is adapted to receive data from one of non-invasive, minimally invasive, and invasive glucose sensor.

In an aspect of the third embodiment, the signal processing module is adapted to receive data from one of an enzymatic, chemical, physical, electrochemical, spectrophotometric, polarimetric, calorimetric, iontophoretic, and radiometric glucose sensor.

In an aspect of the third embodiment, the signal processing module is adapted to receive data from a wholly implantable glucose sensor.

In an aspect of the third embodiment, the detection module includes programming to for ischemia detection.

In an aspect of the third embodiment, the detection module includes programming to detect ischemia from a first oxygen sensor located proximal to or within the glucose sensor.

In an aspect of the third embodiment, the detection module further includes programming to compare a measurement from a first oxygen sensor located proximal to or within the glucose sensor with a measurement from a second oxygen sensor located distal to the glucose sensor for ischemia detection.

In an aspect of the third embodiment, the detection module further includes programming to detect ischemia using pulsed amperometric detection of an electrochemical cell including a working electrode and a reference electrode.

In an aspect of the third embodiment, the detection module further includes programming to detect ischemia by monitoring a counter electrode of an electrochemical cell that includes working, counter and reference electrodes.

In an aspect of the third embodiment, the detection module further includes programming to detect ischemia by monitoring a reference electrode of an electrochemical cell that includes working, counter and reference electrodes.

In an aspect of the third embodiment, the detection module further includes programming to detect ischemia by monitoring a cathode of an electrochemical cell.

In an aspect of the third embodiment, the detection module monitors a level of pH proximal to the glucose sensor.

In an aspect of the third embodiment, the detection module monitors a temperature proximal to the glucose sensor.

In an aspect of the third embodiment, the detection module compares a level of pH proximal to and distal to the sensor.

In an aspect of the third embodiment, the detection module compares a temperature proximal to and distal to the glucose sensor.

In an aspect of the third embodiment, the detection module monitors a pressure or stress within the glucose sensor.

In an aspect of the third embodiment, the detection module evaluates historical data for high amplitude noise above a predetermined threshold.

In an aspect of the third embodiment, the detection module includes programming to perform a Cone of Possibility to detect signal artifacts.

In an aspect of the third embodiment, the detection module evaluates the data stream for a non-physiological rate-of-change.

In an aspect of the third embodiment, the detection module monitors the frequency content of the signal.

In an aspect of the third embodiment, the detection module monitors the frequency content including performing an orthogonal basis function-based transform.

In an aspect of the third embodiment, the orthogonal basis function-based transform includes a Fourier Transform or a wavelet transform.

In an aspect of the third embodiment, the signal estimation module estimates glucose signal values using linear or non-linear regression.

In an aspect of the third embodiment, the signal estimation module estimates glucose signal values using a trimmed mean.

In an aspect of the third embodiment, the signal estimation module estimates glucose signal values using a non-recursive filter.

In an aspect of the third embodiment, the non-recursive filter is a finite impulse response filter.

In an aspect of the third embodiment, the signal estimation module estimates glucose signal values using a recursive filter.

In an aspect of the third embodiment, the recursive filter is an infinite impulse response filter.

In an aspect of the third embodiment, the signal estimation module estimates glucose signal values using a maximum average algorithm.

In an aspect of the third embodiment, the signal estimation module estimates glucose signal values using a Cone of Possibility Replacement Method.

In an aspect of the third embodiment, the signal estimation module further includes programming to estimate future glucose signal values based on historical glucose values.

In an aspect of the third embodiment, the future glucose signal value programming includes algorithmically estimating the future signal value based using at least one of linear regression, non-linear regression, and an auto-regressive algorithm.

In an aspect of the third embodiment, the signal estimation module further includes programming to measure at least one of rate-of-change, acceleration, and physiologically feasibility of one or more signal values, and wherein the signal estimation module further includes programming to selectively apply an algorithm responsive to value of one of the measurements from the detection module.

In an aspect of the third embodiment, signal estimation module includes programming to normalize the data stream based on baseline drift at a reference electrode of a glucose sensor that includes an electrochemical cell including working, counter, and reference electrodes.

In an aspect of the third embodiment, the signal estimation module continually replaces the data stream with estimated signal values.

In an aspect of the third embodiment, the signal estimation module initiates signal replacement of the data stream in response to positive detection of signal artifacts.

In an aspect of the third embodiment, the signal estimation module terminates signal replacement in response to detection of negligible signal artifacts.

In an aspect of the third embodiment, the detection module evaluates the severity of the signal artifacts.

In an aspect of the third embodiment, the detection module evaluates the severity of the signal artifacts based on an amplitude of the transient non-glucose related signal artifacts.

In an aspect of the third embodiment, the detection module evaluates the severity of the signal artifacts based on a duration of the transient non-glucose related signal artifacts.

In an aspect of the third embodiment, the detection module evaluates the severity of the signal artifacts based on a rate-of-change of the transient non-glucose related signal artifacts.

In an aspect of the third embodiment, the detection module evaluates the severity of the signal artifacts based on a frequency content of the transient non-glucose related signal artifacts.

In an aspect of the third embodiment, the signal estimation module includes programming to selectively apply one of a plurality of signal estimation algorithm factors in response to the severity of the signal artifacts.

In an aspect of the third embodiment, the plurality of signal estimation algorithm factors includes a single algorithm with a plurality of parameters that are selectively applied to the algorithm.

In an aspect of the third embodiment, the plurality of signal estimation algorithm factors includes a plurality of distinct algorithms.

In an aspect of the third embodiment, the signal estimation module selectively applies a set of parameters whose values depend on the severity of the signal artifacts to one of a predetermined algorithm.

In an aspect of the third embodiment, the detection module includes programming to discard at least some of the signal artifacts.

In an aspect of the third embodiment, the signal estimation module includes programming to project glucose signal values for a time during which no data is available.

In a fourth embodiment, a system is provided for processing data signals obtained from a glucose sensor, the system including: a signal processing module including programming to monitor a data stream from the sensor over a period of time; a detection module including programming to detect transient non-glucose related signal artifacts in the wherein the plurality of signal estimation algorithm factors include a plurality of distinct algorithms data streams that have a higher amplitude than a system noise; and a signal estimation module including programming to selectively apply one of a plurality of signal estimation algorithm factors to replace non-glucose related signal artifacts.

In an aspect of the fourth embodiment, the signal processing module is adapted to receive data from one of non-invasive, minimally invasive, and invasive glucose sensor.

In an aspect of the fourth embodiment, the signal processing module is adapted to receive data from one of an enzymatic, chemical, physical, electrochemical, spectrophotometric, polarimetric, calorimetric, iontophoretic, and radiometric glucose sensor.

In an aspect of the fourth embodiment, the signal processing module is adapted to receive data from a wholly implantable glucose sensor.

In an aspect of the fourth embodiment, the detection module includes programming to detect ischemia within or proximal to the glucose sensor.

In an aspect of the fourth embodiment, the detection module includes programming to obtain oxygen concentration using an oxygen sensor proximal to or within the glucose sensor.

In an aspect of the fourth embodiment, the detection module includes programming to compare a measurement from an oxygen sensor proximal to or within the glucose sensor with a measurement from an oxygen sensor distal from the glucose sensor.

In an aspect of the fourth embodiment, the detection module includes programming to detect ischemia using pulsed amperometric detection of an electrochemical cell that includes a working electrode and a reference electrode.

In an aspect of the fourth embodiment, the detection module includes programming to monitor a counter electrode of a glucose sensor that includes an electrochemical cell including working, counter and reference electrodes.

In an aspect of the fourth embodiment, the detection module includes programming to monitor a reference electrode of a glucose sensor that includes an electrochemical cell including working, counter and reference electrodes.

In an aspect of the fourth embodiment, the detection module includes programming to monitor a cathode of a glucose sensor that includes an electrochemical cell including an anode and a cathode.

In an aspect of the fourth embodiment, the detection module includes programming to monitor a level of pH proximal to the glucose sensor.

In an aspect of the fourth embodiment, the detection module includes programming to monitor a temperature proximal to the glucose sensor.

In an aspect of the fourth embodiment, the detection module includes programming to compare a level of pH proximal to and distal to the glucose sensor.

In an aspect of the fourth embodiment, the detection module includes programming to compare a temperature proximal to and distal to the sensor.

In an aspect of the fourth embodiment, the detection module includes programming to monitor a pressure or stress within the glucose sensor.

In an aspect of the fourth embodiment, the detection module includes programming to evaluate historical data for high amplitude noise above a predetermined threshold.

In an aspect of the fourth embodiment, the detection module includes programming to perform Cone of Possibility Detection.

In an aspect of the fourth embodiment, the detection module includes programming to evaluate the signal for a non-physiological rate-of-change.

In an aspect of the fourth embodiment, the detection module includes programming to monitor the frequency content of the signal.

In an aspect of the fourth embodiment, the detection module performs an orthogonal basis function-based transform to monitor frequency content.

In an aspect of the fourth embodiment, the transform is a Fourier Transform or a wavelet transform.

In an aspect of the fourth embodiment, the signal estimation module estimates glucose signal values using linear or non-linear regression.

In an aspect of the fourth embodiment, the signal estimation module estimates glucose signal values using a trimmed mean.

In an aspect of the fourth embodiment, the signal estimation module estimates glucose signal values using a non-recursive filter.

In an aspect of the fourth embodiment, the non-recursive filter is a finite impulse response filter.

In an aspect of the fourth embodiment, the signal estimation module estimates glucose signal values using a recursive filter.

In an aspect of the fourth embodiment, the recursive filter is an infinite impulse response filter.

In an aspect of the fourth embodiment, the signal estimation module estimates glucose signal values using a maximum average algorithm.

In an aspect of the fourth embodiment, the signal estimation module estimates glucose signal values using Cone of Possibility Replacement Method algorithm.

In an aspect of the fourth embodiment, the signal estimation module further includes programming to estimate future glucose signal values based on historical glucose values.

In an aspect of the fourth embodiment, future glucose signal value programming includes algorithmically estimating the future signal value based using at least one of linear regression, non-linear regression, and an auto-regressive algorithm.

In an aspect of the fourth embodiment, the signal estimation module further includes programming to measure at least one of rate-of-change, acceleration, and physiologically feasibility of one or more signal values, and wherein the signal estimation module further includes programming to selectively apply an algorithm responsive to value of one of the measurements from the detection module.

In an aspect of the fourth embodiment, the signal estimation module includes programming to normalize the data stream based on baseline drift at a reference electrode of a glucose sensor that includes an electrochemical cell including working, counter, and reference electrodes.

In an aspect of the fourth embodiment, the signal estimation module continually replaces the data stream with estimated signal values.

In an aspect of the fourth embodiment, the signal estimation module initiates signal replacement of the data stream in response to positive detection of signal artifacts.

In an aspect of the fourth embodiment, the signal estimation module terminates signal replacement in response to detection of negligible signal artifacts.

In an aspect of the fourth embodiment, the detection module evaluates the severity of the signal artifacts.

In an aspect of the fourth embodiment, the detection module evaluates the severity of the signal artifacts based on an amplitude of the transient non-glucose related signal artifacts.

In an aspect of the fourth embodiment, the detection module evaluates the severity of the signal artifacts based on a duration of the transient non-glucose related signal artifacts.

In an aspect of the fourth embodiment, the detection module evaluates the severity of the signal artifacts based on a rate-of-change of the transient non-glucose related signal artifacts.

In an aspect of the fourth embodiment, the detection module evaluates the severity of the signal artifacts based on a frequency content of the transient non-glucose related signal artifacts.

In an aspect of the fourth embodiment, the signal estimation module includes programming to selectively apply one of a plurality of signal estimation algorithm factors in response to the severity of the signal artifacts.

In an aspect of the fourth embodiment, the plurality of signal estimation algorithm factors includes a single algorithm with a plurality of parameters that are selectively applied to the algorithm.

In an aspect of the fourth embodiment, the plurality of signal estimation algorithm factors includes a plurality of distinct algorithms.

In an aspect of the fourth embodiment, the signal estimation module selectively applies a set of parameters whose values depend on the severity of the signal artifacts to one of a predetermined algorithm.

In an aspect of the fourth embodiment, the detection module includes programming to discard at least some of the signal artifacts.

In an aspect of the fourth embodiment, the signal estimation module includes programming to project glucose signal values for a time during which no data is available.

In a fifth embodiment, an implantable glucose monitoring device is provided including: a glucose sensor; and a processor operatively linked to the sensor designed to receive a data stream from the sensor; wherein the processor is programmed to analyze the data stream and to detect transient non-glucose related signal artifacts in the data stream that have a higher amplitude than system noise, and to replace at least some of the signal artifacts with estimated values.

DETAILED DESCRIPTION OF THE PREFERRED EMBODIMENTS

Figure 1:
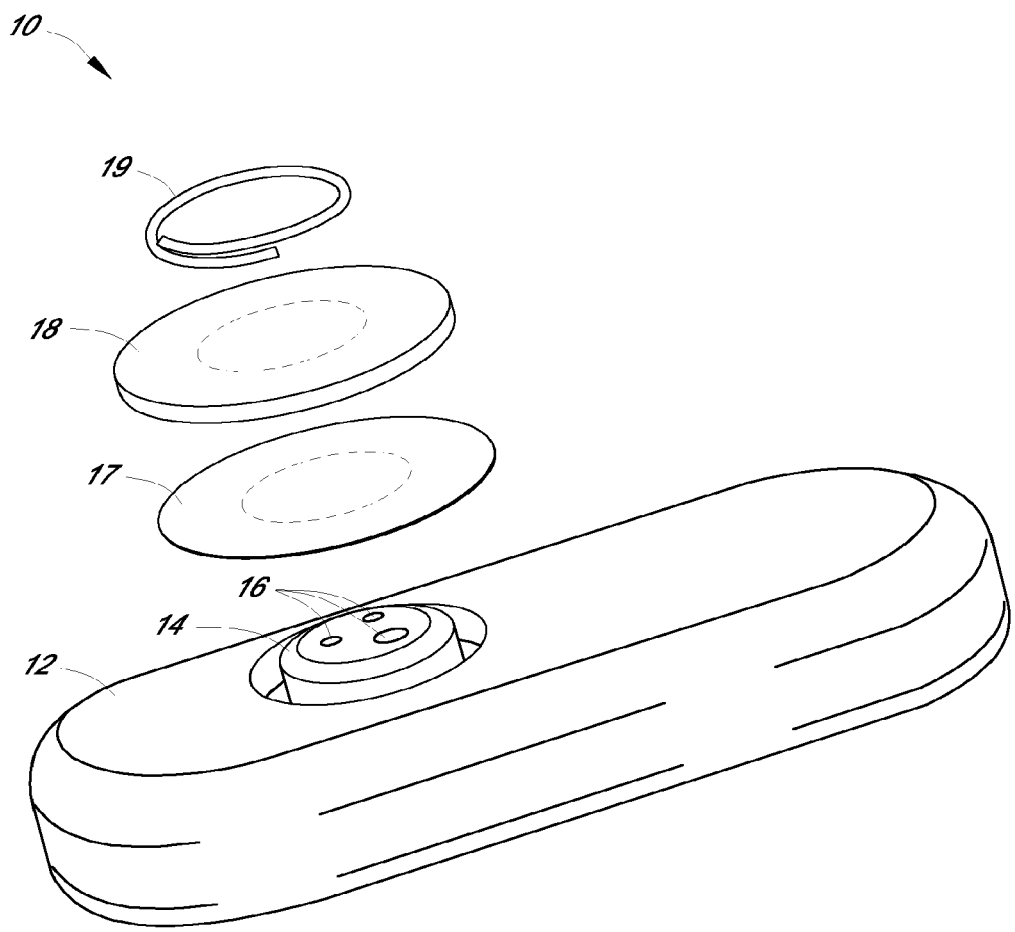
FIG. 1 is an exploded perspective view of a glucose sensor in one embodiment.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "EEPROM," as used herein, is a broad term and is used in its ordinary sense, including, without limitation, electrically erasable programmable read-only memory, which is user-modifiable read-only memory (ROM) that can be erased and reprogrammed (e.g., written to) repeatedly through the application of higher than normal electrical voltage.

The term "SRAM," as used herein, is a broad term and is used in its ordinary sense, including, without limitation, static random access memory (RAM) that retains data bits in its memory as long as power is being supplied.

The term "A/D Converter," as used herein, is a broad term and is used in its ordinary sense, including, without limitation, hardware and/or software that converts analog electrical signals into corresponding digital signals.

The term "microprocessor," as used herein, is a broad term and is used in its ordinary sense, including, without limitation a computer system or processor designed to perform arithmetic and logic operations using logic circuitry that responds to and processes the basic instructions that drive a computer.

The term "RF transceiver," as used herein, is a broad term and is used in its ordinary sense, including, without limitation, a radio frequency transmitter and/or receiver for transmitting and/or receiving signals.

The term "jitter," as used herein, is a broad term and is used in its ordinary sense, including, without limitation, noise above and below the mean caused by ubiquitous noise caused by a circuit and/or environmental effects; jitter can be seen in amplitude, phase timing, or the width of the signal pulse.

The terms "raw data stream" and "data stream," as used herein, are broad terms and are used in their ordinary sense, including, without limitation, an analog or digital signal directly related to the measured glucose from the glucose sensor. In one example, the raw data stream is digital data in "counts" converted by an A/D converter from an analog signal (e.g., voltage or amps) representative of a glucose concentration. The terms broadly encompass a plurality of time spaced data points from a substantially continuous glucose sensor, which comprises individual measurements taken at time intervals ranging from fractions of a second up to, e.g., 1, 2, or 5 minutes or longer.

The term "counts," as used herein, is a broad term and is used in its ordinary sense, including, without limitation, a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The terms "glucose sensor" and "member for determining the amount of glucose in a biological sample," as used herein, are broad terms and are used in an ordinary sense, including, without limitation, any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant O2 and the product H2O2, one can use an electrode to monitor the current change in either the co-reactant or the product to determine glucose concentration.

The terms "operably connected" and "operably linked," as used herein, are broad terms and are used in their ordinary sense, including, without limitation, one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "electronic circuitry," as used herein, is a broad term and is used in its ordinary sense, including, without limitation, the components of a device configured to process biological information obtained from a host. In the case of a glucose-measuring device, the biological information is obtained by a sensor regarding a particular glucose in a biological fluid, thereby providing data regarding the amount of that glucose in the fluid. U.S. Pat. Nos. 4,757,022, 5,497,772 and 4,787,398, which are hereby incorporated by reference, describe suitable electronic circuits that can be utilized with devices including the biointerface membrane of a preferred embodiment.

The term "substantially" as used herein, is a broad term and is used in its ordinary sense, including, without limitation, being largely but not necessarily wholly that which is specified.

The term "proximal" as used herein, is a broad term and is used in its ordinary sense, including, without limitation, near to a point of reference such as an origin, a point of attachment, or the midline of the body. For example, in some embodiments of a glucose sensor, wherein the glucose sensor is the point of reference, an oxygen sensor located proximal to the glucose sensor will be in contact with or nearby the glucose sensor such that their respective local environments are shared (e.g., levels of glucose, oxygen, pH, temperature, etc. are similar).

The term "distal" as used herein, is a broad term and is used in its ordinary sense, including, without limitation, spaced relatively far from a point of reference, such as an origin or a point of attachment, or midline of the body. For example, in some embodiments of a glucose sensor, wherein the glucose sensor is the point of reference, an oxygen sensor located distal to the glucose sensor will be sufficiently far from the glucose sensor such their respective local environments are not shared (e.g., levels of glucose, oxygen, pH, temperature, etc. may not be similar).

The term "electrochemical cell," as used herein, is a broad term and is used in its ordinary sense, including, without limitation, a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "potentiostat," as used herein, is a broad term and is used in its ordinary sense, including, without limitation, an electrical system that controls the potential between the working and reference electrodes of a three-electrode cell at a preset value. It forces whatever current is necessary to flow between the working and counter electrodes to keep the desired potential, as long as the needed cell voltage and current do not exceed the compliance limits of the potentiostat.

The term "electrical potential," as used herein, is a broad term and is used in its ordinary sense, including, without limitation, the electrical potential difference between two points in a circuit which is the cause of the flow of a current.

The term "host," as used herein, is a broad term and is used in its ordinary sense, including, without limitation, mammals, particularly humans.

The phrase "continuous glucose sensing," as used herein, is a broad term and is used in its ordinary sense, including, without limitation, the period in which monitoring of plasma glucose concentration is continuously or continually performed, for example, at time intervals ranging from fractions of a second up to, e.g., 1, 2, or 5 minutes, or longer.

The term "sensor head," as used herein, is a broad term and is used in its ordinary sense, including, without limitation, the region of a monitoring device responsible for the detection of a particular glucose. The sensor head generally comprises a non-conductive body, a working electrode (anode), a reference electrode and a counter electrode (cathode) passing through and secured within the body forming an electrochemically reactive surface at one location on the body and an electronic connection at another location on the body, and a multi-region membrane affixed to the body and covering the electrochemically reactive surface. The counter electrode typically has a greater electrochemically reactive surface area than the working electrode. During general operation of the sensor a biological sample (e.g., blood or interstitial fluid) or a portion thereof contacts (directly or after passage through one or more membranes or domains) an enzyme (e.g., glucose oxidase); the reaction of the biological sample (or portion thereof) results in the formation of reaction products that allow a determination of the glucose level in the biological sample. In some embodiments, the multi-region membrane includes an enzyme domain (e.g., glucose oxidase), and an electrolyte phase (e.g., a free-flowing liquid phase comprising an electrolyte-containing fluid, as described further below).

The term "electrochemically reactive surface," as used herein, is a broad term and is used in its ordinary sense, including, without limitation, the surface of an electrode where an electrochemical reaction takes place. In the case of the working electrode, the hydrogen peroxide produced by the enzyme catalyzed reaction of the glucose being detected reacts creating a measurable electronic current (e.g., detection of glucose utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, e.g., $O_2$ is reduced at the electrode surface in order to balance the current being generated by the working electrode.

The term "electronic connection," as used herein, is a broad term and is used in its ordinary sense, including, without limitation, any electronic connection known to those in the art that can be utilized to interface the sensor head electrodes with the electronic circuitry of a device such as mechanical (e.g., pin and socket) or soldered.

The terms "operably connected" and "operably linked," as used herein, are broad terms and are used in their ordinary sense, including, without limitation, one or more components being linked to another component(s) in a manner that allows transmission of signals between the components, e.g., wired or wirelessly. For example, one or more electrodes can be used to detect the amount of analyte in a sample and convert that information into a signal; the signal can then be transmitted to an electronic circuit means. In this case, the electrode is "operably linked" to the electronic circuitry.

The term "sensing membrane," as used herein, is a broad term and is used in its ordinary sense, including, without limitation, a permeable or semi-permeable membrane that can be comprised of two or more domains and is typically constructed of materials of a few microns thickness or more, which are permeable to oxygen and may or may not be permeable to glucose. In one example, the sensing membrane comprises an immobilized glucose oxidase enzyme, which enables an electrochemical reaction to occur to measure a concentration of glucose.

The term "biointerface membrane," as used herein, is a broad term and is used in its ordinary sense, including, without limitation, a permeable membrane that can be comprised of two or more domains and is typically constructed of materials of a few microns thickness or more, which can be placed over the sensor body to keep host cells (e.g., macrophages) from gaining proximity to, and thereby damaging, the sensing membrane or forming a barrier cell layer and interfering with the transport of glucose across the tissue-device interface.

The term "Clarke Error Grid," as used herein, is a broad term and is used in its ordinary sense, including, without limitation, an error grid analysis, which evaluates the clinical significance of the difference between a reference glucose value and a sensor generated glucose value, taking into account 1) the value of the reference glucose measurement, 2) the value of the sensor glucose measurement, 3) the relative difference between the two values, and 4) the clinical significance of this difference. See Clarke et al., "Evaluating Clinical Accuracy of Systems for Self-Monitoring of Blood Glucose," Diabetes Care, Volume 10, Number 5, September-October 1987, which is incorporated by reference herein in its entirety.

The term "physiologically feasible," as used herein, is a broad term and is used in its ordinary sense, including, without limitation, the physiological parameters obtained from continuous studies of glucose data in humans and/or animals. For example, a maximal sustained rate of change of glucose in humans of about 4 to 5 mg/dL/min and a maximum acceleration of the rate of change of about 0.1 to 0.2 mg/dL/min/min are deemed physiologically feasible limits. Values outside of these limits would be considered non-physiological and likely a result of signal error, for example. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (e.g., about 20 to 30 minutes) is a straight line, which can be used to set physiological limits.

The term "ischemia," as used herein, is a broad term and is used in its ordinary sense, including, without limitation, local and temporary deficiency of blood supply due to obstruction of circulation to a part (e.g., sensor). Ischemia can be caused by mechanical obstruction (e.g., arterial narrowing or disruption) of the blood supply, for example.

The term "system noise," as used herein, is a broad term and is used in its ordinary sense, including, without limitation, unwanted electronic or diffusion-related noise which can include Gaussian, motion-related, flicker, kinetic, or other white noise, for example.

The terms "signal artifacts" and "transient non-glucose related signal artifacts that have a higher amplitude than system noise," as used herein, are broad terms and are used in their ordinary sense, including, without limitation, signal noise that is caused by substantially non-glucose reaction rate-limiting phenomena, such as ischemia, pH changes, temperature changes, pressure, and stress, for example. Signal artifacts, as described herein, are typically transient and characterized by a higher amplitude than system noise.

The terms "low noise," as used herein, is a broad term and is used in its ordinary sense, including, without limitation, noise that substantially decreases signal amplitude.

The terms "high noise" and "high spikes," as used herein, are broad terms and are used in their ordinary sense, including, without limitation, noise that substantially increases signal amplitude.

The term "frequency content," as used herein, is a broad term and is used in its ordinary sense, including, without limitation, the spectral density, including the frequencies contained within a signal and their power.

The term "spectral density," as used herein, is a broad term and is used in its ordinary sense, including, without limitation, power spectral density of a given bandwidth of electromagnetic radiation is the total power in this bandwidth divided by the specified bandwidth. Spectral density is usually expressed in Watts per Hertz (W/Hz).

The term "orthogonal transform," as used herein, is a broad term and is used in its ordinary sense, including, without limitation, a general integral transform that is defined by $g(\alpha)=\int_a^b f(t)K(\alpha,t)dt$, where $K(\alpha,t)$ represents a set of orthogonal basis functions.

The term "Fourier Transform," as used herein, is a broad term and is used in its ordinary sense, including, without limitation, a technique for expressing a waveform as a weighted sum of sines and cosines.

The term "Discrete Fourier Transform," as used herein, is a broad term and is used in its ordinary sense, without limitation, a specialized Fourier transform where the variables are discrete.

The term "wavelet transform," as used herein, is a broad term and is used in its ordinary sense, including, without limitation, a transform which converts a signal into a series of wavelets, which in theory allows signals processed by the wavelet transform to be stored more efficiently than ones processed by Fourier transform. Wavelets can also be constructed with rough edges, to better approximate real-world signals.

The term "chronoamperometry," as used herein, is a broad term and is used in its ordinary sense, including, without limitation, an electrochemical measuring technique used for electrochemical analysis or for the determination of the kinetics and mechanism of electrode reactions. A fast-rising potential pulse is enforced on the working (or reference) electrode of an electrochemical cell and the current flowing through this electrode is measured as a function of time.

The term "pulsed amperometric detection," as used herein, is a broad term and is used in its ordinary sense, including, without limitation, an electrochemical flow cell and a controller, which applies the potentials and monitors current generated by the electrochemical reactions. The cell can include one or multiple working electrodes at different applied potentials. Multiple electrodes can be arranged so that they face the chromatographic flow independently (parallel configuration), or sequentially (series configuration).

The term "linear regression," as used herein, is a broad term and is used in its ordinary sense, including, without limitation, finding a line in which a set of data has a minimal measurement from that line. Byproducts of this algorithm include a slope, a y-intercept, and an R-Squared value that determine how well the measurement data fits the line.

The term "non-linear regression," as used herein, is a broad term and is used in its ordinary sense, including, without limitation, fitting a set of data to describe the relationship between a response variable and one or more explanatory variables in a non-linear fashion.

The term "mean," as used herein, is a broad term and is used in its ordinary sense, including, without limitation, the sum of the observations divided by the number of observations.

The term "trimmed mean," as used herein, is a broad term and is used in its ordinary sense, including, without limitation, a mean taken after extreme values in the tails of a variable (e.g., highs and lows) are eliminated or reduced (e.g., "trimmed"). The trimmed mean compensates for sensitivities to extreme values by dropping a certain percentage of values on the tails. For example, the 50% trimmed mean is the mean of the values between the upper and lower quartiles. The 90% trimmed mean is the mean of the values after truncating the lowest and highest 5% of the values. In one example, two highest and two lowest measurements are removed from a data set and then the remaining measurements are averaged.

The term "non-recursive filter," as used herein, is a broad term and is used in its ordinary sense, including, without limitation, an equation that uses moving averages as inputs and outputs.

The terms "recursive filter" and "auto-regressive algorithm," as used herein, are broad terms and are used in their ordinary sense, including, without limitation, an equation in which includes previous averages are part of the next filtered output. More particularly, the generation of a series of observations whereby the value of each observation is partly dependent on the values of those that have immediately preceded it. One example is a regression structure in which lagged response values assume the role of the independent variables.

The term "signal estimation algorithm factors," as used herein, is a broad term and is used in its ordinary sense, including, without limitation, one or more algorithms that use historical and/or present signal data stream values to estimate unknown signal data stream values. For example, signal estimation algorithm factors can include one or more algorithms, such as linear or non-linear regression. As another example, signal estimation algorithm factors can include one or more sets of coefficients that can be applied to one algorithm.

As employed herein, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade).

Overview

The preferred embodiments relate to the use of a glucose sensor that measures a concentration of glucose or a substance indicative of the concentration or presence of the glucose. In some embodiments, the glucose sensor is a continuous device, for example a subcutaneous, transdermal, or intravascular device. In some embodiments, the device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, or the like.

The glucose sensor can use any known method, including invasive, minimally invasive, and non-invasive sensing techniques, to provide a data stream indicative of the concentration of glucose in a host. The data stream is typically a raw data signal that is used to provide a useful value of glucose to a user, such as a patient or doctor, who may be using the sensor. It is well known that raw data streams typically include system noise such as defined herein; however the preferred embodiments address the detection and replacement of "signal artifacts" as defined herein. Accordingly, appropriate signal estimation (e.g., filtering, data smoothing, augmenting, projecting, and/or other methods) replace such erroneous signals (e.g., signal artifacts) in the raw data stream.

Glucose Sensor

The glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

FIG. 1 is an exploded perspective view of one exemplary embodiment comprising an implantable glucose sensor 10 that utilizes amperometric electrochemical sensor technology to measure glucose concentration. In this exemplary embodiment, a body 12 and head 14 house the electrodes 16 and sensor electronics, which are described in more detail below with reference to FIG. 2. Three electrodes 16 are operably connected to the sensor electronics (FIG. 1) and are covered by a sensing membrane 17 and a biointerface membrane 18, which are attached by a clip 19.

In one embodiment, the three electrodes 16, which protrude through the head 14, include a platinum working electrode, a platinum counter electrode, and a silver/silver chloride reference electrode. The top ends of the electrodes are in contact with an electrolyte phase (not shown), which is a free-flowing fluid phase disposed between the sensing membrane 17 and the electrodes 16. The sensing membrane 17 includes an enzyme, e.g., glucose oxidase, which covers the electrolyte phase. The biointerface membrane 18 covers the sensing membrane 17 and serves, at least in part, to protect the sensor 10 from external forces that can result in environmental stress cracking of the sensing membrane 17.

In the illustrated embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

In one embodiment, a potentiostat is employed to monitor the electrochemical reaction at the electrochemical cell. The potentiostat applies a constant potential to the working and reference electrodes to determine a current value. The current that is produced at the working electrode (and flows through the circuitry to the counter electrode) is proportional to the amount of $H_2O_2$ that diffuses to the working electrode. Accordingly, a raw signal can be produced that is representative of the concentration of glucose in the user's body, and therefore can be utilized to estimate a meaningful glucose value, such as described herein.

One problem with raw data stream output of enzymatic glucose sensors such as described above is caused by transient non-glucose reaction rate-limiting phenomenon. For example, if oxygen is deficient, relative to the amount of glucose, then the enzymatic reaction will be limited by oxygen rather than glucose. Consequently, the output signal will be indicative of the oxygen concentration rather than the glucose concentration, producing erroneous signals. Other non-glucose reaction rate-limiting phenomenon could include temperature and/or pH changes, for example. Accordingly, reduction of signal noise, and particularly replacement of transient non-glucose related signal artifacts in the data stream that have a higher amplitude than system noise, can be performed in the sensor and/or in the receiver, such as described in more detail below in the sections entitled "Signal Artifacts Detection" and "Signal Artifacts Replacement."

Figure 2:
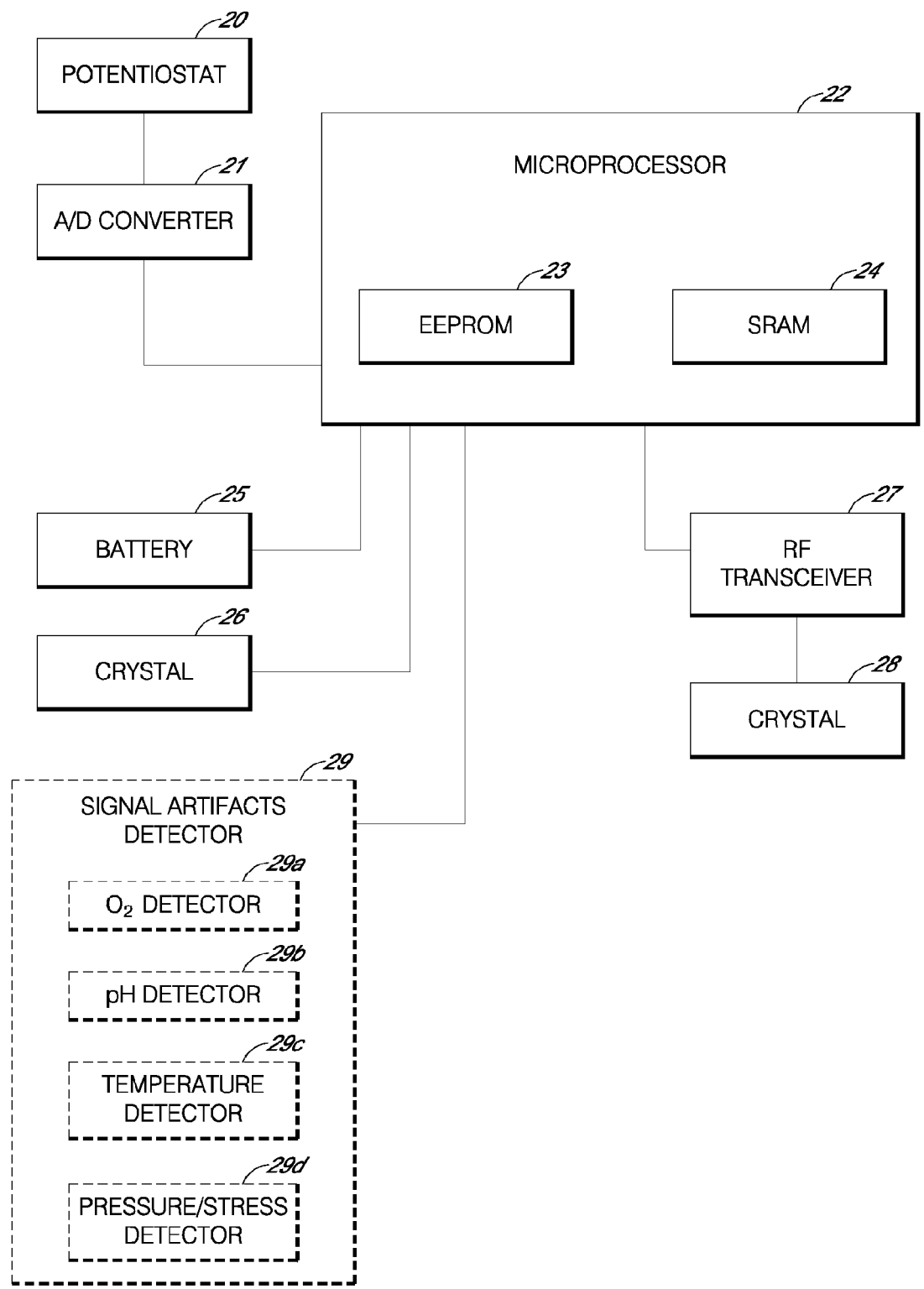
FIG. 2 is a block diagram that illustrates sensor electronics in one embodiment.

FIG. 2 is a block diagram that illustrates one possible configuration of the sensor electronics in one embodiment. In this embodiment, a potentiostat 20 is shown, which is operatively connected to electrodes 16 (FIG. 1) to obtain a current value, and includes a resistor (not shown) that translates the current into voltage. An A/D converter 21 digitizes the analog signal into "counts" for processing. Accordingly, the resulting raw data stream in counts is directly related to the current measured by the potentiostat 20.

A microprocessor 22 is the central control unit that houses EEPROM 23 and SRAM 24, and controls the processing of the sensor electronics. It is noted that certain alternative embodiments can utilize a computer system other than a microprocessor to process data as described herein. In other alternative embodiments, an application-specific integrated circuit (ASIC) can be used for some or all the sensor's central processing. The EEPROM 23 provides semi-permanent storage of data, for example, storing data such as sensor identifier (ID) and programming to process data streams (e.g., programming for signal artifacts detection and/or replacement such as described elsewhere herein). The SRAM 24 can be used for the system's cache memory, for example for temporarily storing recent sensor data.

A battery 25 is operatively connected to the microprocessor 22 and provides the necessary power for the sensor 10. In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries can be used to power the system. A Quartz Crystal 26 is operatively connected to the microprocessor 22 and maintains system time for the computer system as a whole.

Figure 3A:
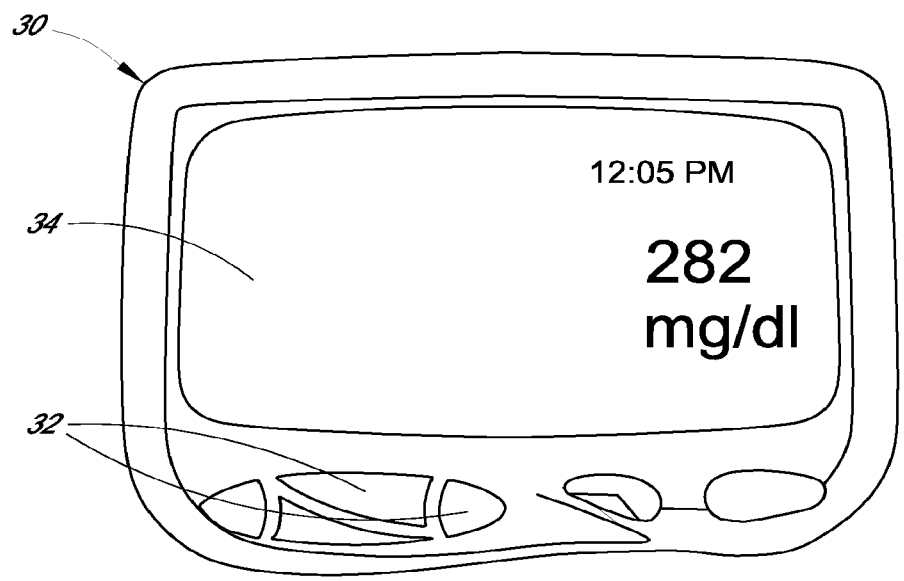
FIGS. 3A to 3D are schematic views of a receiver in first, second, third, and fourth embodiments, respectively.
Figure 3B:
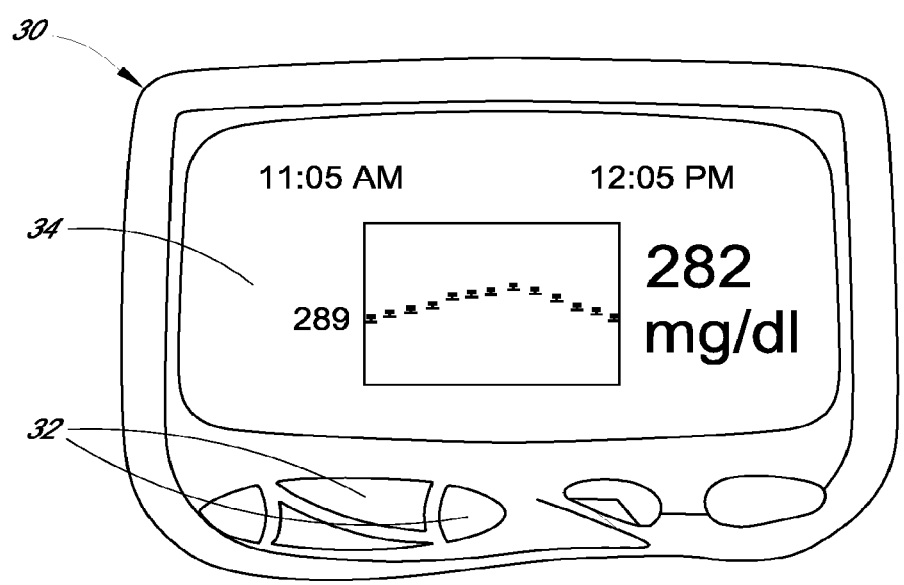
Figure 3C:
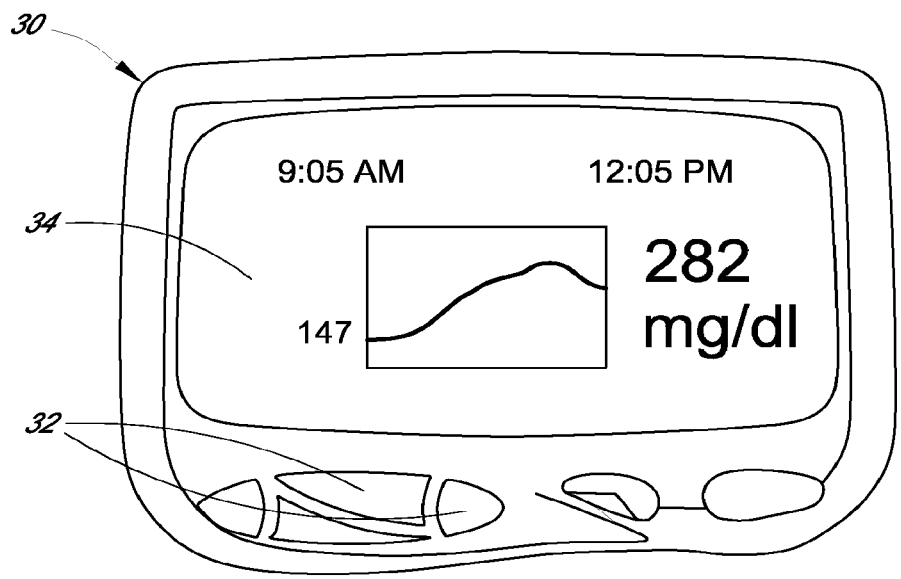
Figure 3D:
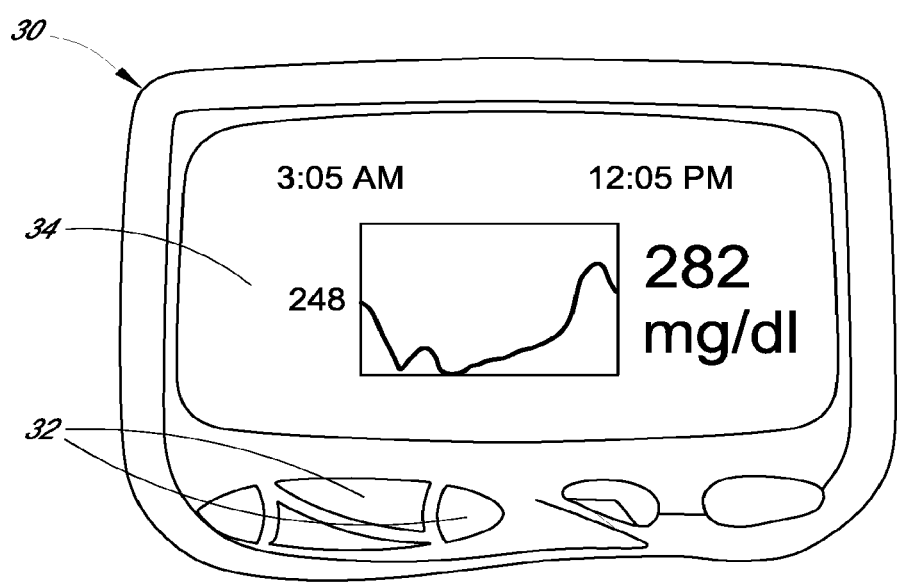
Figure 4:
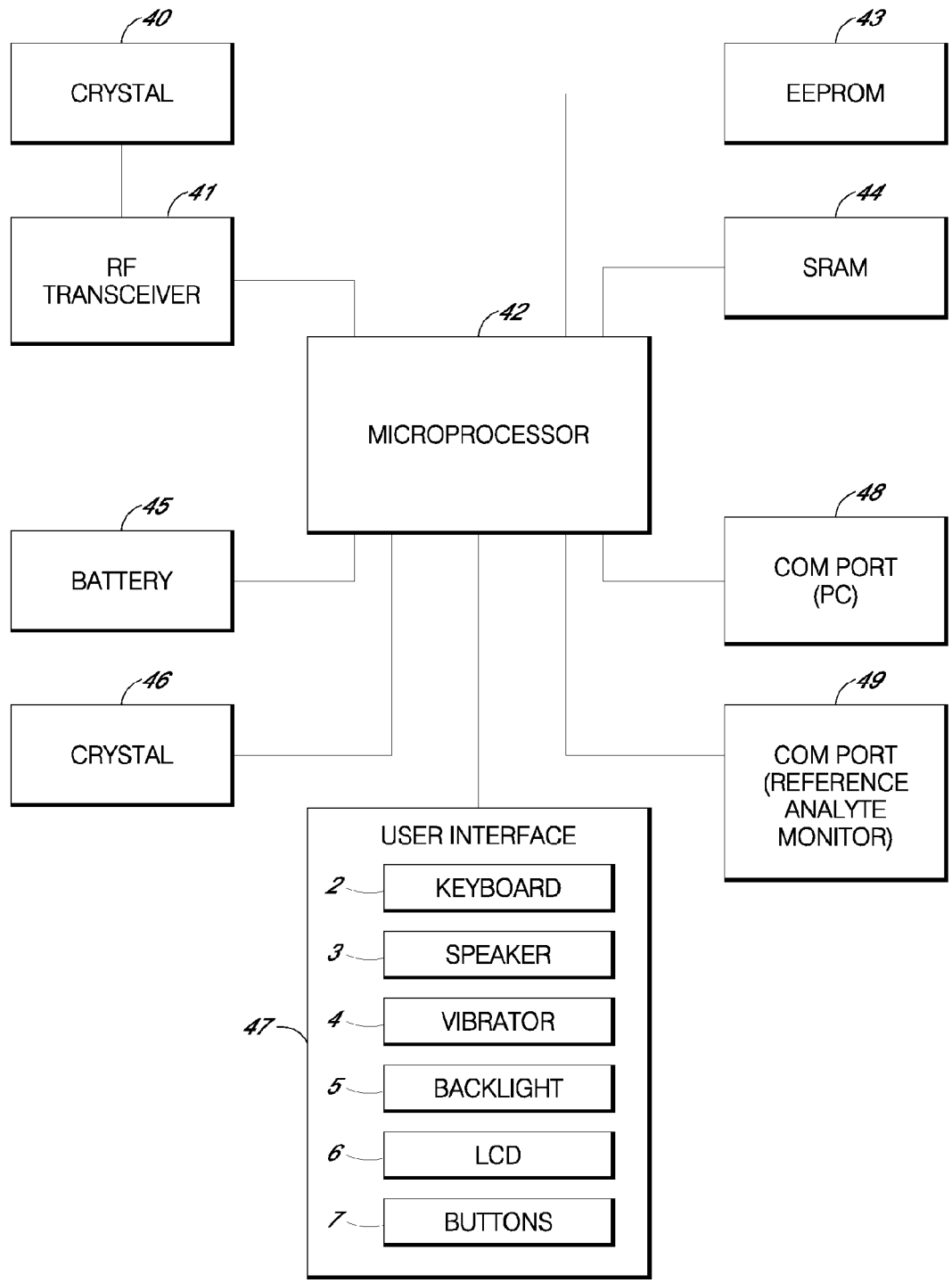
FIG. 4 is a block diagram of receiver electronics in one embodiment.

An RF Transceiver 27 is operably connected to the microprocessor 22 and transmits the sensor data from the sensor 10 to a receiver (see FIGS. 3 and 4). Although an RF transceiver is shown here, some other embodiments can include a wired rather than wireless connection to the receiver. In yet other embodiments, the receiver can be transcutaneously powered via an inductive coupling, for example. A second quartz crystal 28 provides the system time for synchronizing the data transmissions from the RF transceiver. It is noted that the transceiver 27 can be substituted with a transmitter in other embodiments.

In some embodiments, a Signal Artifacts Detector 29 includes one or more of the following: an oxygen detector 29a, a pH detector 29b, a temperature detector 29c, and a pressure/stress detector 29d, which is described in more detail with reference to signal artifacts detection. It is noted that in some embodiments the signal artifacts detector 29 is a separate entity (e.g., temperature detector) operatively connected to the microprocessor, while in other embodiments, the signal artifacts detector is a part of the microprocessor and utilizes readings from the electrodes, for example, to detect ischemia and other signal artifacts.

Receiver

FIGS. 3A to 3D are schematic views of a receiver 30 including representations of estimated glucose values on its user interface in first, second, third, and fourth embodiments, respectively. The receiver 30 comprises systems to receive, process, and display sensor data from the glucose sensor 10, such as described herein. Particularly, the receiver 30 can be a pager-sized device, for example, and comprise a user interface that has a plurality of buttons 32 and a liquid crystal display (LCD) screen 34, and which can optionally include a backlight. In some embodiments, the user interface can also include a keyboard, a speaker, and a vibrator, as described below with reference to FIG. 4.

FIG. 3A illustrates a first embodiment wherein the receiver 30 shows a numeric representation of the estimated glucose value on its user interface, which is described in more detail elsewhere herein.

FIG. 3B illustrates a second embodiment wherein the receiver 30 shows an estimated glucose value and approximately one hour of historical trend data on its user interface, which is described in more detail elsewhere herein.

FIG. 3C illustrates a third embodiment wherein the receiver 30 shows an estimated glucose value and approximately three hours of historical trend data on its user interface, which is described in more detail elsewhere herein.

FIG. 3D illustrates a fourth embodiment wherein the receiver 30 shows an estimated glucose value and approximately nine hours of historical trend data on its user interface, which is described in more detail elsewhere herein.

In some embodiments, a user can toggle through some or all of the screens shown in FIGS. 3A to 3D using a toggle button on the receiver. In some embodiments, the user will be able to interactively select the type of output displayed on their user interface. In other embodiments, the sensor output can have alternative configurations.

FIG. 4 is a block diagram that illustrates one possible configuration of the receiver's 30 electronics. It is noted that the receiver 30 can comprise a configuration such as described with reference to FIGS. 3A to 3D, above. Alternatively, the receiver 30 can comprise other configurations, including a desktop computer, laptop computer, a personal digital assistant (PDA), a server (local or remote to the receiver), or the like. In some embodiments, the receiver 30 can be adapted to connect (via wired or wireless connection) to a desktop computer, laptop computer, PDA, server (local or remote to the receiver), or the like, in order to download data from the receiver 30. In some alternative embodiments, the receiver 30 can be housed within or directly connected to the sensor 10 in a manner that allows sensor and receiver electronics to work directly together and/or share data processing resources. Accordingly, the receiver's electronics can be generally referred to as a "computer system."

A quartz crystal 40 is operatively connected to an RF transceiver 41 that together function to receive and synchronize data streams (e.g., raw data streams transmitted from the RF transceiver). Once received, a microprocessor 42 processes the signals, such as described below.

The microprocessor 42 is the central control unit that provides the processing, such as calibration algorithms stored within EEPROM 43. The EEPROM 43 is operatively connected to the microprocessor 42 and provides semi-permanent storage of data, storing data such as receiver ID and programming to process data streams (e.g., programming for performing calibration and other algorithms described elsewhere herein). SRAM 44 is used for the system's cache memory and is helpful in data processing.

A battery 45 is operatively connected to the microprocessor 42 and provides power for the receiver. In one embodiment, the battery is a standard AAA alkaline battery, however any appropriately sized and powered battery can be used. In some embodiments, a plurality of batteries can be used to power the system. A quartz crystal 46 is operatively connected to the microprocessor 42 and maintains system time for the computer system as a whole.

A user interface 47 comprises a keyboard 2, speaker 3, vibrator 4, backlight 5, liquid crystal display (LCD 6), and one or more buttons 7. The components that comprise the user interface 47 provide controls to interact with the user. The keyboard 2 can allow, for example, input of user information about himself/herself, such as mealtime, exercise, insulin administration, and reference glucose values. The speaker 3 can provide, for example, audible signals or alerts for conditions such as present and/or predicted hyper- and hypoglycemic conditions. The vibrator 4 can provide, for example, tactile signals or alerts for reasons such as described with reference to the speaker, above. The backlight 5 can be provided, for example, to aid the user in reading the LCD in low light conditions. The LCD 6 can be provided, for example, to provide the user with visual data output such as is illustrated in FIGS. 3A to 3D. The buttons 7 can provide for toggle, menu selection, option selection, mode selection, and reset, for example.

Communication ports, including a PC communication (com) port 48 and a reference glucose monitor com port 49 can be provided to enable communication with systems that are separate from, or integral with, the receiver 30. The PC com port 48, for example, a serial communications port, allows for communicating with another computer system (e.g., PC, PDA, server, or the like). In one exemplary embodiment, the receiver 30 is able to download historical data to a physician's PC for retrospective analysis by the physician. The reference glucose monitor com port 49 allows for communicating with a reference glucose monitor (not shown) so that reference glucose values can be downloaded into the receiver 30, for example, automatically. In one embodiment, the reference glucose monitor is integral with the receiver 30, and the reference glucose com port 49 allows internal communication between the two integral systems. In another embodiment, the reference glucose monitor com port 49 allows a wireless or wired connection to reference glucose monitor such as a self-monitoring blood glucose monitor (e.g., for measuring finger stick blood samples).

Calibration

Figure 5:
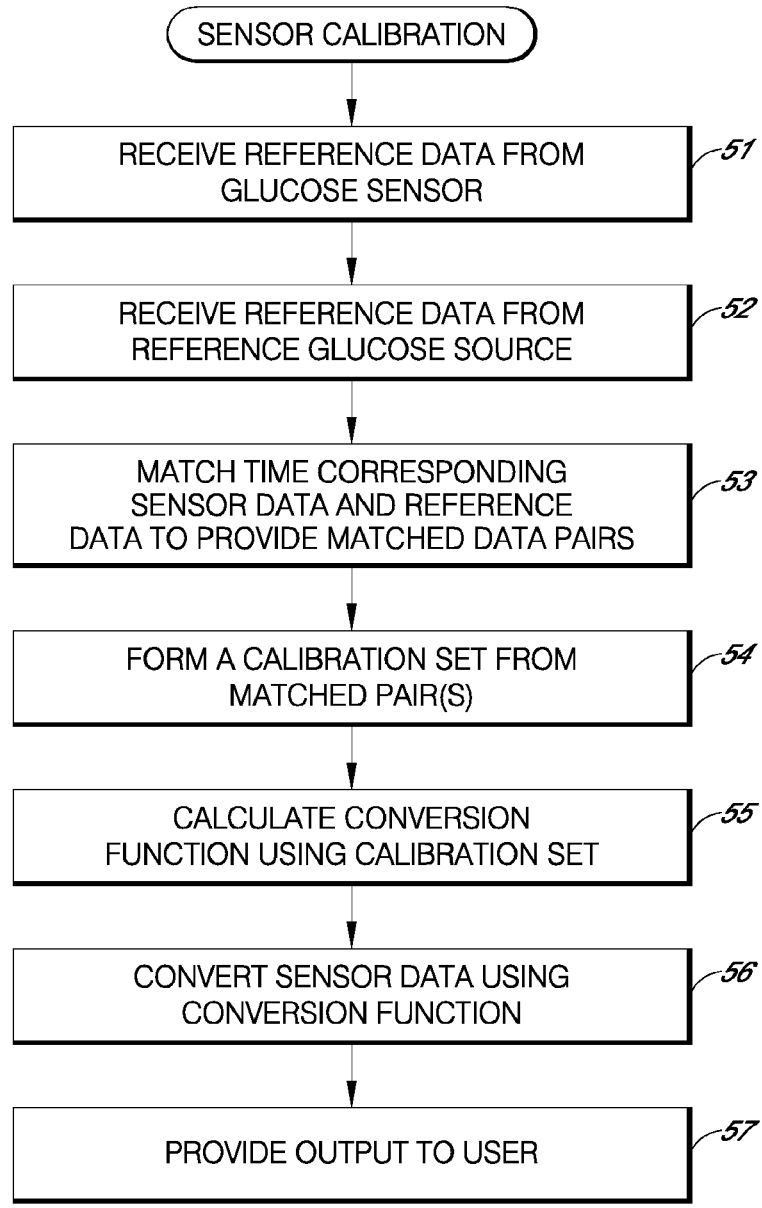
FIG. 5 is a flow chart that illustrates the process of calibrating the sensor data in one embodiment.

Reference is now made to FIG. 5, which is a flow chart that illustrates the process of initial calibration and data output of the glucose sensor 10 in one embodiment.

Calibration of the glucose sensor 10 comprises data processing that converts a sensor data stream into an estimated glucose measurement that is meaningful to a user. Accordingly, a reference glucose value can be used to calibrate the data stream from the glucose sensor 10.

At block 51, a sensor data receiving module, also referred to as the sensor data module, receives sensor data (e.g., a data stream), including one or more time-spaced sensor data points, from a sensor via the receiver, which can be in wired or wireless communication with the sensor. Some or all of the sensor data point(s) can be replaced by estimated signal values to address signal noise such as described in more detail elsewhere herein. It is noted that during the initialization of the sensor, prior to initial calibration, the receiver 30 (e.g., computer system) receives and stores the sensor data, however it may not display any data to the user until initial calibration and eventually stabilization of the sensor 10 has been determined.

At block 52, a reference data receiving module, also referred to as the reference input module, receives reference data from a reference glucose monitor, including one or more reference data points. In one embodiment, the reference glucose points can comprise results from a self-monitored blood glucose test (e.g., from a finger stick test). In one such embodiment, the user can administer a self-monitored blood glucose test to obtain glucose value (e.g., point) using any known glucose sensor, and enter the numeric glucose value into the computer system. In another such embodiment, a self-monitored blood glucose test comprises a wired or wireless connection to the receiver 30 (e.g. computer system) so that the user simply initiates a connection between the two devices, and the reference glucose data is passed or downloaded between the self-monitored blood glucose test and the receiver 30. In yet another such embodiment, the self-monitored glucose test is integral with the receiver 30 so that the user simply provides a blood sample to the receiver 30, and the receiver 30 runs the glucose test to determine a reference glucose value.

Certain acceptability parameters can be set for reference values received from the user. For example, in one embodiment, the receiver may only accept reference glucose values between about 40 and about 400 mg/dL.

At block 53, a data matching module, also referred to as the processor module, matches reference data (e.g., one or more reference glucose data points) with substantially time corresponding sensor data (e.g., one or more sensor data points) to provide one or more matched data pairs. In one embodiment, one reference data point is matched to one time corresponding sensor data point to form a matched data pair. In another embodiment, a plurality of reference data points are averaged (e.g., equally or non-equally weighted average, mean-value, median, or the like) and matched to one time corresponding sensor data point to form a matched data pair. In another embodiment, one reference data point is matched to a plurality of time corresponding sensor data points averaged to form a matched data pair. In yet another embodiment, a plurality of reference data points are averaged and matched to a plurality of time corresponding sensor data points averaged to form a matched data pair.

In one embodiment, a time corresponding sensor data comprises one or more sensor data points that occur, for example, 15±5 min after the reference glucose data timestamp (e.g., the time that the reference glucose data is obtained). In this embodiment, the 15 minute time delay has been chosen to account for an approximately 10 minute delay introduced by the filter used in data smoothing and an approximately 5 minute physiological time-lag (e.g., the time necessary for the glucose to diffusion through a membrane(s) of an glucose sensor). In alternative embodiments, the time corresponding sensor value can be more or less than in the above-described embodiment, for example ±60 minutes. Variability in time correspondence of sensor and reference data can be attributed to, for example, a longer or shorter time delay introduced during signal estimation, or if the configuration of the glucose sensor 10 incurs a greater or lesser physiological time lag.

In some practical implementations of the sensor 10, the reference glucose data can be obtained at a time that is different from the time that the data is input into the receiver 30. Accordingly, it should be noted that the "time stamp" of the reference glucose (e.g., the time at which the reference glucose value was obtained) may not be the same as the time at which the receiver 30 obtained the reference glucose data. Therefore, some embodiments include a time stamp requirement that ensures that the receiver 30 stores the accurate time stamp for each reference glucose value, that is, the time at which the reference value was actually obtained from the user.

In some embodiments, tests are used to evaluate the best-matched pair using a reference data point against individual sensor values over a predetermined time period (e.g., about 30 minutes). In one such embodiment, the reference data point is matched with sensor data points at 5-minute intervals and each matched pair is evaluated. The matched pair with the best correlation can be selected as the matched pair for data processing. In some alternative embodiments, matching a reference data point with an average of a plurality of sensor data points over a predetermined time period can be used to form a matched pair.

At block 54, a calibration set module, also referred to as the processor module, forms an initial calibration set from a set of one or more matched data pairs, which are used to determine the relationship between the reference glucose data and the sensor glucose data, such as described in more detail with reference to block 55, below.

The matched data pairs, which make up the initial calibration set, can be selected according to predetermined criteria. In some embodiments, the number (n) of data pair(s) selected for the initial calibration set is one. In other embodiments, n data pairs are selected for the initial calibration set wherein n is a function of the frequency of the received reference data points. In one exemplary embodiment, six data pairs make up the initial calibration set.

In some embodiments, the data pairs are selected only within a certain glucose value threshold, for example wherein the reference glucose value is between about 40 and about 400 mg/dL. In some embodiments, the data pairs that form the initial calibration set are selected according to their time stamp.

At block 55, the conversion function module uses the calibration set to create a conversion function. The conversion function substantially defines the relationship between the reference glucose data and the glucose sensor data. A variety of known methods can be used with the preferred embodiments to create the conversion function from the calibration set. In one embodiment, wherein a plurality of matched data points form the initial calibration set, a linear least squares regression is performed on the initial calibration set such as described in more detail with reference to FIG. 6.

At block 56, a sensor data transformation module uses the conversion function to transform sensor data into substantially real-time glucose value estimates, also referred to as calibrated data, as sensor data is continuously (or intermittently) received from the sensor. In other words, the offset value at any given point in time can be subtracted from the raw value (e.g., in counts) and divided by the slope to obtain the estimated glucose value:

$$mg/dL = \frac{(rawvalue / \text{offset})}{slope}$$

In some alternative embodiments, the sensor and/or reference glucose values are stored in a database for retrospective analysis.

At block 57, an output module provides output to the user via the user interface. The output is representative of the estimated glucose value, which is determined by converting the sensor data into a meaningful glucose value such as described in more detail with reference to block 56, above. User output can be in the form of a numeric estimated glucose value, an indication of directional trend of glucose concentration, and/or a graphical representation of the estimated glucose data over a period of time, for example. Other representations of the estimated glucose values are also possible, for example audio and tactile.

In one embodiment, such as shown in FIG. 3A, the estimated glucose value is represented by a numeric value. In other exemplary embodiments, such as shown in FIGS. 3B to 3D, the user interface graphically represents the estimated glucose data trend over predetermined a time period (e.g., one, three, and nine hours, respectively). In alternative embodiments, other time periods can be represented.

Accordingly, after initial calibration of the sensor, real-time continuous glucose information can be displayed on the user interface so that the user can regularly and proactively care for his/her diabetic condition within the bounds set by his/her physician.

In alternative embodiments, the conversion function is used to predict glucose values at future points in time. These predicted values can be used to alert the user of upcoming hypoglycemic or hyperglycemic events. Additionally, predicted values can be used to compensate for the time lag (e.g., 15 minute time lag such as described elsewhere herein), so that an estimated glucose value displayed to the user represents the instant time, rather than a time delayed estimated value.

In some embodiments, the substantially real-time estimated glucose value, a predicted future estimated glucose value, a rate of change, and/or a directional trend of the glucose concentration is used to control the administration of a constituent to the user, including an appropriate amount and time, in order to control an aspect of the user's biological system. One such example is a closed loop glucose sensor and insulin pump, wherein the glucose data (e.g., estimated glucose value, rate of change, and/or directional trend) from the glucose sensor is used to determine the amount of insulin, and time of administration, that can be given to a diabetic user to evade hyper- and hypoglycemic conditions.

Figure 6:
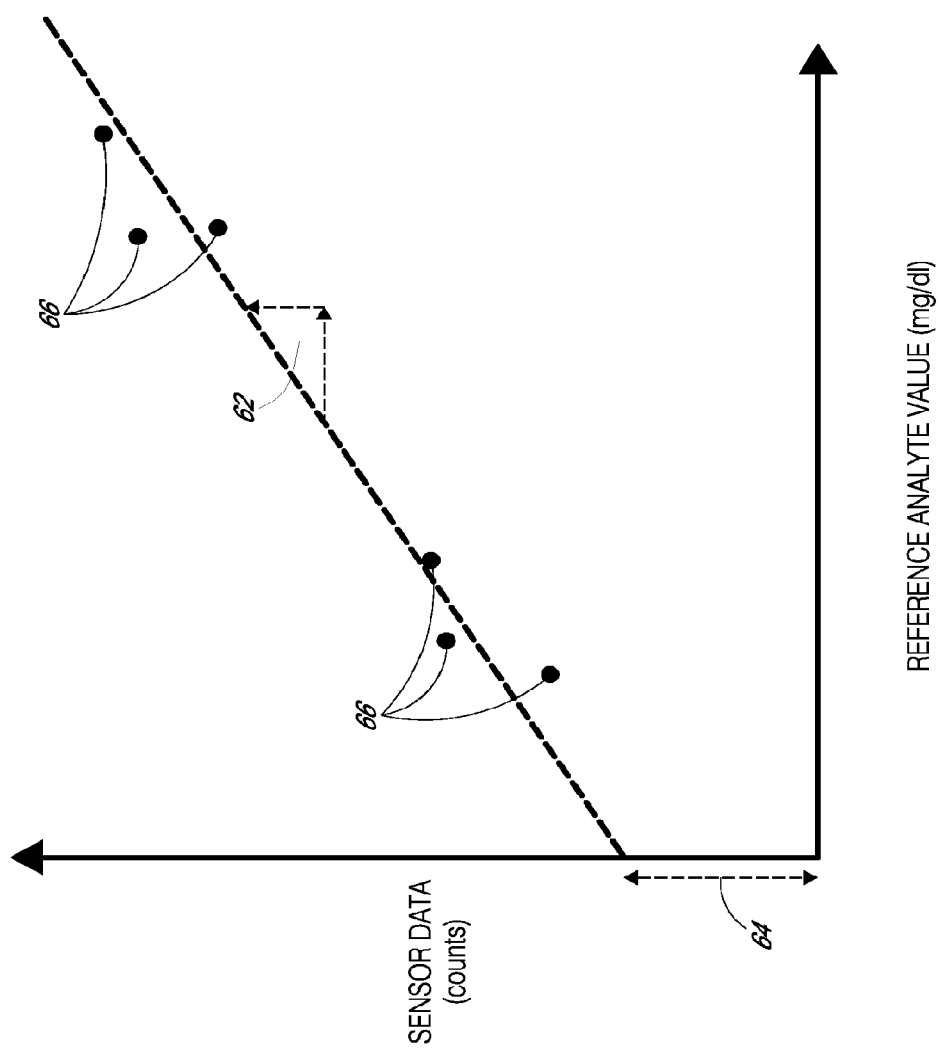
FIG. 6 is a graph that illustrates a linear regression used to calibrate the sensor data in one embodiment.

FIG. 6 is a graph that illustrates one embodiment of a regression performed on a calibration set to create a conversion function such as described with reference to FIG. 5, block 55, above. In this embodiment, a linear least squares regression is performed on the initial calibration set. The x-axis represents reference glucose data; the y-axis represents sensor data. The graph pictorially illustrates regression of matched pairs 66 in the calibration set. The regression calculates a slope 62 and an offset 64, for example, using the well-known slope-intercept equation (y=mx+b), which defines the conversion function.

In alternative embodiments, other algorithms could be used to determine the conversion function, for example forms of linear and non-linear regression, for example fuzzy logic, neural networks, piece-wise linear regression, polynomial fit, genetic algorithms, and other pattern recognition and signal estimation techniques.

In yet other alternative embodiments, the conversion function can comprise two or more different optimal conversions because an optimal conversion at any time is dependent on one or more parameters, such as time of day, calories consumed, exercise, or glucose concentration above or below a set threshold, for example. In one such exemplary embodiment, the conversion function is adapted for the estimated glucose concentration (e.g., high vs. low). For example in an implantable glucose sensor it has been observed that the cells surrounding the implant will consume at least a small amount of glucose as it diffuses toward the glucose sensor. Assuming the cells consume substantially the same amount of glucose whether the glucose concentration is low or high, this phenomenon will have a greater effect on the concentration of glucose during low blood sugar episodes than the effect on the concentration of glucose during relatively higher blood sugar episodes. Accordingly, the conversion function can be adapted to compensate for the sensitivity differences in blood sugar level. In one implementation, the conversion function comprises two different regression lines, wherein a first regression line is applied when the estimated blood glucose concentration is at or below a certain threshold (e.g., 150 mg/dL) and a second regression line is applied when the estimated blood glucose concentration is at or above a certain threshold (e.g., 150 mg/dL). In one alternative implementation, a predetermined pivot of the regression line that forms the conversion function can be applied when the estimated blood is above or below a set threshold (e.g., 150 mg/dL), wherein the pivot and threshold are determined from a retrospective analysis of the performance of a conversion function and its performance at a range of glucose concentrations. In another implementation, the regression line that forms the conversion function is pivoted about a point in order to comply with clinical acceptability standards (e.g., Clarke Error Grid, Consensus Grid, mean absolute relative difference, or other clinical cost function). Although only a few example implementations are described, other embodiments include numerous implementations wherein the conversion function is adaptively applied based on one or more parameters that can affect the sensitivity of the sensor data over time.

Additional methods for processing sensor glucose data are disclosed in copending U.S. patent application Ser. No.

10/633,367 filed Aug. 1, 2003 and entitled, "SYSTEM AND METHODS FOR PROCESSING ANALYTE SENSOR DATA," which is incorporated herein by reference in its entirety. In view of the above-described data processing, it should be obvious that improving the accuracy of the data stream will be advantageous for improving output of glucose sensor data. Accordingly, the following description is related to improving data output by decreasing signal artifacts on the raw data stream from the sensor. The data smoothing methods of preferred embodiments can be employed in conjunction with any sensor or monitor measuring levels of an analyte in vivo, wherein the level of the analyte fluctuates over time, including but not limited to such sensors as described in U.S. Pat. No. 6,001,067 to Shults et al.; U.S. Patent Application 2003/0023317 to Brauker et al.; U.S. Pat. No. 6,212,416 to Ward et al.; U.S. Pat. No. 6,119,028 to Schulman et al; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al; U.S. Pat. No. 6,514,718 to Heller et al; and U.S. Pat. No. 5,985,129 to Gough et al., each of which are incorporated in there entirety herein by reference.

Signal Artifacts

Typically, a glucose sensor produces a data stream that is indicative of the glucose concentration of a host, such as described in more detail above. However, it is well known that the above described glucose sensor is only one example of an abundance of glucose sensors that are able to provide raw data output indicative of the concentration of glucose. Thus, it should be understood that the systems and methods described herein, including signal artifacts detection, signal artifacts replacement, and other data processing, can be applied to a data stream obtained from any glucose sensor.

Raw data streams typically have some amount of "system noise," caused by unwanted electronic or diffusion-related noise that degrades the quality of the signal and thus the data. Accordingly, conventional glucose sensors are known to smooth raw data using methods that filter out this system noise, and the like, in order to improve the signal to noise ratio, and thus data output. One example of a conventional data-smoothing algorithm includes a finite impulse response filter (FIR), which is particularly suited for reducing high-frequency noise (see Steil et al. U.S. Pat. No. 6,558,351).

Figure 7A:
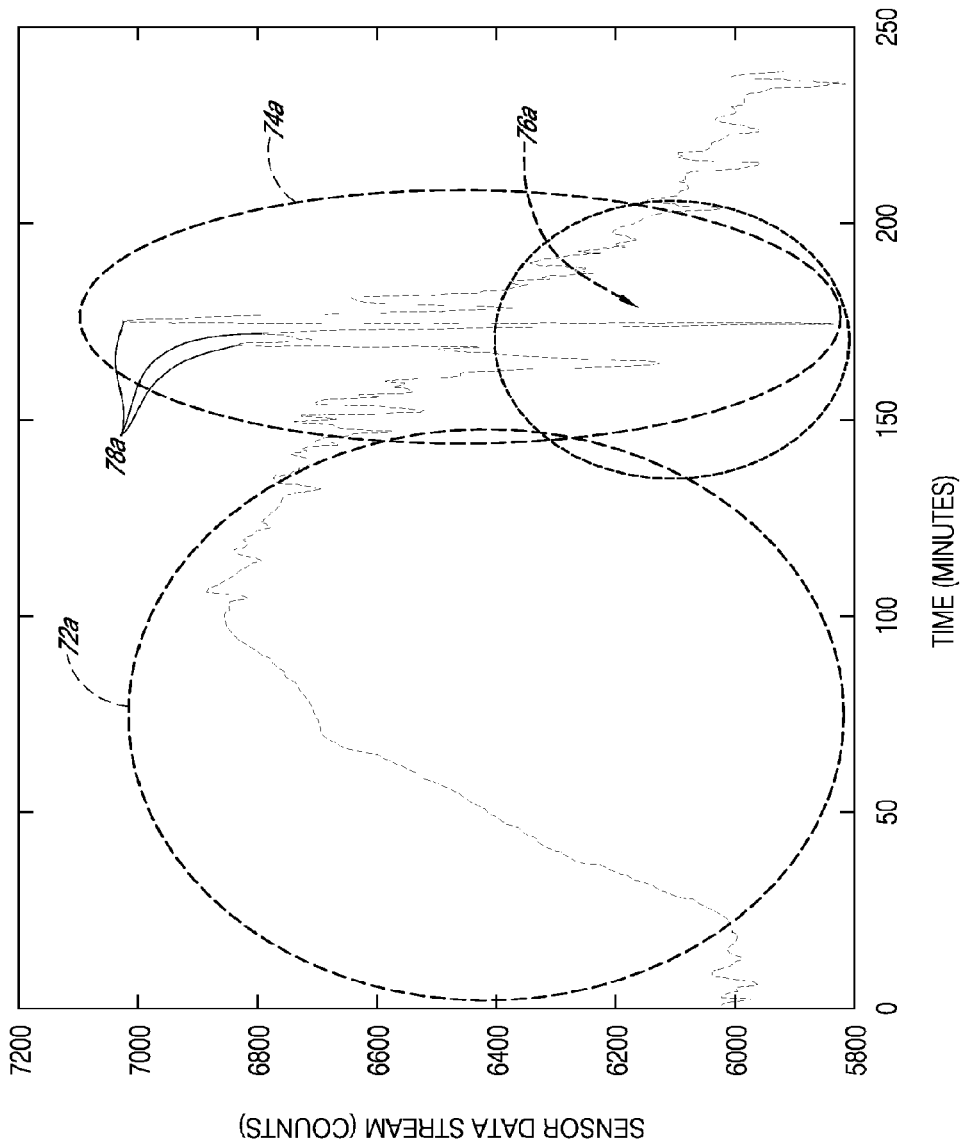
FIG. 7A is a graph that shows a raw data stream obtained from a glucose sensor over a 4 hour time span in one example.
Figure 7B:
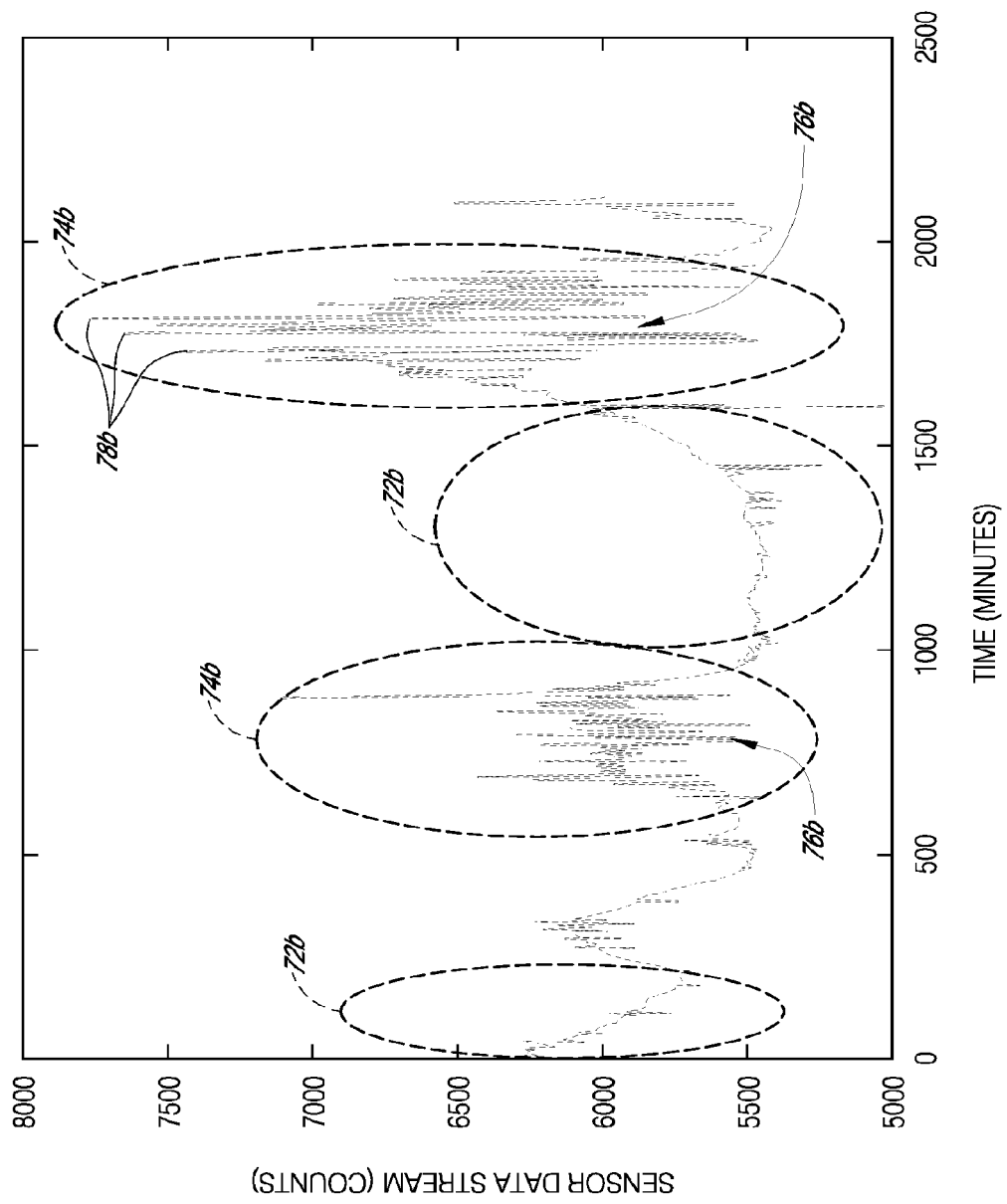
FIG. 7B is a graph that shows a raw data stream obtained from a glucose sensor over a 36 hour time span in another example.

FIGS. 7A and 7B are graphs of raw data streams from an implantable glucose sensor prior to data smoothing. FIG. 7A is a graph that shows a raw data stream obtained from a glucose sensor over an approximately 4 hour time span in one example. FIG. 7B is a graph that shows a raw data stream obtained from a glucose sensor over an approximately 36 hour time span in another example. The x-axis represents time in minutes. The y-axis represents sensor data in counts. In these examples, sensor output in counts is transmitted every 30-seconds.

The "system noise" such as shown in sections 72a, 72b of the data streams of FIGS. 7A and 7B, respectively, illustrate time periods during which system noise can be seen on the data stream. This system noise can be characterized as Gaussian, Brownian, and/or linear noise, and can be substantially normally distributed about the mean. The system noise is likely electronic and diffusion-related, or the like, and can be smoothed using techniques such as by using an FIR filter. The system noise such as shown in the data of sections 72a, 72b is a fairly accurate representation of glucose concentration and can be confidently used to report glucose concentration to the user when appropriately calibrated.

The "signal artifacts" such as shown in sections 74a, 74b of the data stream of FIGS. 7A and 7B, respectively, illustrate time periods during which "signal artifacts" can be seen, which are significantly different from the previously described system noise (sections 72a, 72b). This noise, such as shown in section 74a and 74b, is referred to herein as "signal artifacts" and more particularly described as "transient non-glucose dependent signal artifacts that have a higher amplitude than system noise." At times, signal artifacts comprise low noise, which generally refers to noise that substantially decreases signal amplitude 76a, 76b herein, which is best seen in the signal artifacts 74b of FIG. 7B. Occasional high spikes 78a, 78b, which generally correspond to noise that substantially increases signal amplitude, can also be seen in the signal artifacts, which generally occur after a period of low noise. These high spikes are generally observed after transient low noise and typically result after reaction rate-limiting phenomena occur. For example, in an embodiment where a glucose sensor requires an enzymatic reaction, local ischemia creates a reaction that is rate-limited by oxygen, which is responsible for low noise. In this situation, glucose would be expected to build up in the membrane because it would not be completely catabolized during the oxygen deficit. When oxygen is again in excess, there would also be excess glucose due to the transient oxygen deficit. The enzyme rate would speed up for a short period until the excess glucose is catabolized, resulting in high noise.

Analysis of signal artifacts such as shown sections 74a, 74b of FIGS. 7A and 7B, respectively, indicates that the observed low noise is caused by substantially non-glucose reaction dependent phenomena, such as ischemia that occurs within or around a glucose sensor in vivo, for example, which results in the reaction becoming oxygen dependent. As a first example, at high glucose levels, oxygen can become limiting to the enzymatic reaction, resulting in a non-glucose dependent downward trend in the data (best seen in FIG. 7B). As a second example, certain movements or postures taken by the patient can cause transient downward noise as blood is squeezed out of the capillaries resulting in local ischemia, and causing non-glucose dependent low noise. Because excess oxygen (relative to glucose) is necessary for proper sensor function, transient ischemia can result in a loss of signal gain in the sensor data. In this second example oxygen can also become transiently limited due to contracture of tissues around the sensor interface. This is similar to the blanching of skin that can be observed when one puts pressure on it. Under such pressure, transient ischemia can occur in both the epidermis and subcutaneous tissue. Transient ischemia is common and well tolerated by subcutaneous tissue.

In another example of non-glucose reaction rate-limiting phenomena, skin temperature can vary dramatically, which can result in thermally related erosion of the signal (e.g., temperature changes between 32 and 39 degrees Celsius have been measured in humans). In yet another embodiment, wherein the glucose sensor is placed intravenously, increased impedance can result from the sensor resting against wall of the blood vessel, for example, producing this non-glucose reaction rate-limiting noise due to oxygen deficiency.

Because signal artifacts are not mere system noise, but rather are caused by specific rate-limiting mechanisms, methods used for conventional random noise filtration produce data lower (or in some cases higher) than the actual blood glucose levels due to the expansive nature of these signal artifacts. To overcome this, the preferred embodiments provide systems and methods for replacing at least some of the signal artifacts by estimating glucose signal values.

Figure 8:
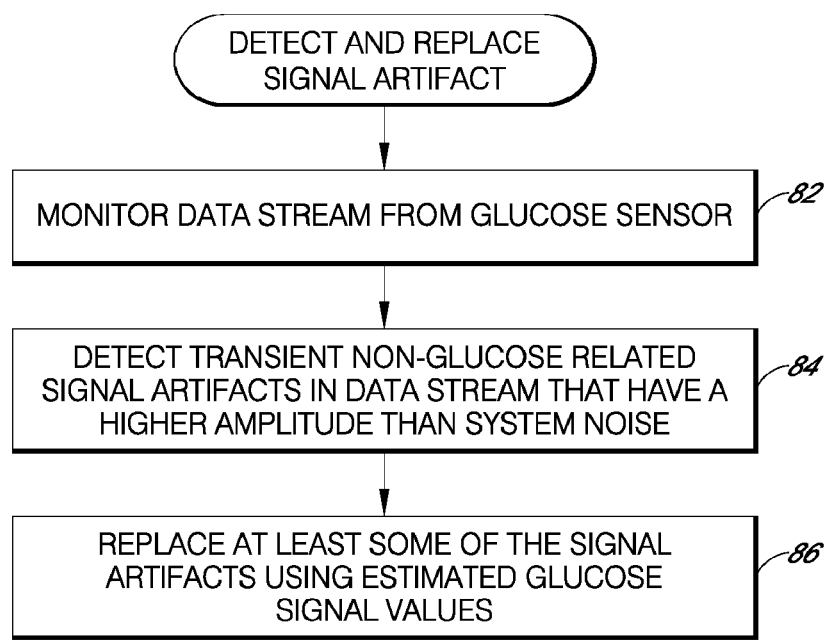
FIG. 8 is a flow chart that illustrates the process of detecting and replacing transient non-glucose related signal artifacts in a data stream in one embodiment.

FIG. 8 is a flow chart that illustrates the process of detecting and replacing signal artifacts in certain embodiments. It is noted that "signal artifacts" particularly refers to the transient non-glucose related artifacts that has a higher amplitude than that of system noise. Typically, signal artifacts are caused by non-glucose rate-limiting phenomenon such as described in more detail above.

At block 82, a sensor data receiving module, also referred to as the sensor data module 82, receives sensor data (e.g., a data stream), including one or more time-spaced sensor 10 data points. In some embodiments, the data stream is stored in the sensor for additional processing; in some alternative embodiments, the sensor 10 periodically transmits the data stream to the receiver 30, which can be in wired or wireless communication with the sensor.

At block 84, a signal artifacts detection module, also referred to as the signal artifacts detector 84, is programmed to detect transient non-glucose related signal artifacts in the data stream that have a higher amplitude than system noise, such as described in more detail with reference to FIGS. 7A and 7B, above. The signal artifacts detector can comprise an oxygen detector, a pH detector, a temperature detector, and/or a pressure/stress detector, for example, the signal artifacts detector 29 in FIG. 2. In some embodiments, the signal artifacts detector at block 84 is located within the microprocessor 22 in FIG. 2 and utilizes existing components of the glucose sensor 10 to detect signal artifacts, for example by pulsed amperometric detection, counter electrode monitoring, reference electrode monitoring, and frequency content monitoring, which are described elsewhere herein. In yet other embodiments, the data stream can be sent from the sensor to the receiver which comprises programming in the microprocessor 42 in FIG. 4 that performs algorithms to detect signal artifacts, for example such as described with reference to "Cone of Possibility Detection" method described in more detail below. Numerous embodiments for detecting signal artifacts are described in more detail in the section entitled, "Signal Artifacts Detection," all of which are encompassed by the signal artifacts detection at block 84.

At block 86, the signal artifacts replacement module, also referred to as the signal estimation module, replaces some or an entire data stream with estimated glucose signal values using signal estimation. Numerous embodiments for performing signal estimation are described in more detail in the section entitled "Signal Artifacts Replacement," all of which are encompassed by the signal artifacts replacement module, block 86. It is noted that in some embodiments, signal estimation/replacement is initiated in response to positive detection of signal artifacts on the data stream, and subsequently stopped in response to detection of negligible signal artifacts on the data stream. In some embodiments, the system waits a predetermined time period (e.g., between 30 seconds and 30 minutes) before switching the signal estimation on or off to ensure that a consistent detection has been ascertained. In some embodiments, however, signal estimation/replacement can continuously or continually run.

Some embodiments of signal estimation can additionally include discarding data that is considered sufficiently unreliable and/or erroneous such that the data should not be used in a signal estimation algorithm. In these embodiments, the system can be programmed to discard outlier data points, for example data points that are so extreme that they can skew the data even with the most comprehensive filtering or signal estimation, and optionally replace those points with a projected value based on historical data or present data (e.g., linear regression, recursive filtering, or the like). One example of discarding sensor data includes discarding sensor data that falls outside of a "Cone of Possibility" such as described in more detail elsewhere herein. Another example includes discarding sensor data when signal artifacts detection detects values outside of a predetermined threshold (e.g., oxygen concentration below a set threshold, temperature above a certain threshold, signal amplitude above a certain threshold, etc). Any of the signal estimation/replacement algorithms described herein can then be used to project data values for those data that were discarded.

Signal Artifacts Detection

Analysis of signals from glucose sensors indicates at least two types of noise, which are characterized herein as 1) system noise and 2) signal artifacts, such as described in more detail above. It is noted that system noise is easily smoothed using the algorithms provided herein; however, the systems and methods described herein particularly address signal artifacts, by replacing transient erroneous signal noise caused by rate-limiting phenomenon with estimated signal values.

In certain embodiments of signal artifacts detection, oxygen monitoring is used to detect whether transient non-glucose dependent signal artifacts due to ischemia. Low oxygen concentrations in or near the glucose sensor can account for a large part of the transient non-glucose related signal artifacts as defined herein on a glucose sensor signal, particularly in subcutaneously implantable glucose sensors. Accordingly, detecting oxygen concentration, and determining if ischemia exists can discover ischemia-related signal artifacts. A variety of methods can be used to test for oxygen. For example, an oxygen-sensing electrode, or other oxygen sensor can be employed. The measurement of oxygen concentration can be sent to a microprocessor, which determines if the oxygen concentration indicates ischemia.

In some embodiments of ischemia detection, an oxygen sensor is placed proximal to or within the glucose sensor. For example, the oxygen sensor can be located on or near the glucose sensor such that their respective local environments are shared and oxygen concentration measurement from the oxygen sensor represents an accurate measurement of the oxygen concentration on or within the glucose sensor. In some alternative embodiments of ischemia detection, an oxygen sensor is also placed distal to the glucose sensor. For example, the oxygen sensor can be located sufficiently far from the glucose sensor such that their respective local environments are not shared and oxygen measurements from the proximal and distal oxygen sensors can be compared to determine the relative difference between the respective local environments. By comparing oxygen concentration proximal and distal oxygen sensor, change in local (proximal) oxygen concentration can be determined from a reference (distal) oxygen concentration.

Oxygen sensors are useful for a variety of purposes. For example, U.S. Pat. No. 6,512,939 to Colvin et al., which is incorporated herein by reference, discloses an oxygen sensor that measures background oxygen levels. However, Colvin et al. rely on the oxygen sensor for the data stream of glucose measurements by subtraction of oxygen remaining after exhaustion of glucose by an enzymatic reaction from total unreacted oxygen concentration.

In another embodiment of ischemia detection, wherein the glucose sensor is an electrochemical sensor that includes a potentiostat, pulsed amperometric detection can be employed to determine an oxygen measurement. Pulsed amperometric detection includes switching, cycling, or pulsing the voltage of the working electrode (or reference electrode) in an electrochemical system, for example between a positive voltage (e.g., +0.6 for detecting glucose) and a negative voltage (e.g., -0.6 for detecting oxygen). U.S. Pat. No. 4,680,268 to Clark, Jr., which is incorporated by reference herein, describes pulsed amperometric detection. In contrast to using signal replacement, Clark, Jr. addresses oxygen deficiency by supplying additional oxygen to the enzymatic reaction.

In another embodiment of ischemia detection, wherein the glucose sensor is an electrochemical sensor and contains a potentiostat, oxygen deficiency can be seen at the counter electrode when insufficient oxygen is available for reduction, which thereby affects the counter electrode in that it is unable to balance the current coming from the working electrode. When insufficient oxygen is available for the counter electrode, the counter electrode can be driven in its electrochemical search for electrons all the way to its most negative value, which could be ground or 0.0V, which causes the reference to shift, reducing the bias voltage such as described in more detail below. In other words, a common result of ischemia will be seen as a drop off in sensor current as a function of glucose concentration (e.g., lower sensitivity). This happens because the working electrode no longer oxidizes all of the $H_2O_2$ arriving at its surface because of the reduced bias. In some extreme circumstances, an increase in glucose can produce no increase in current or even a decrease in current.

Figure 9:
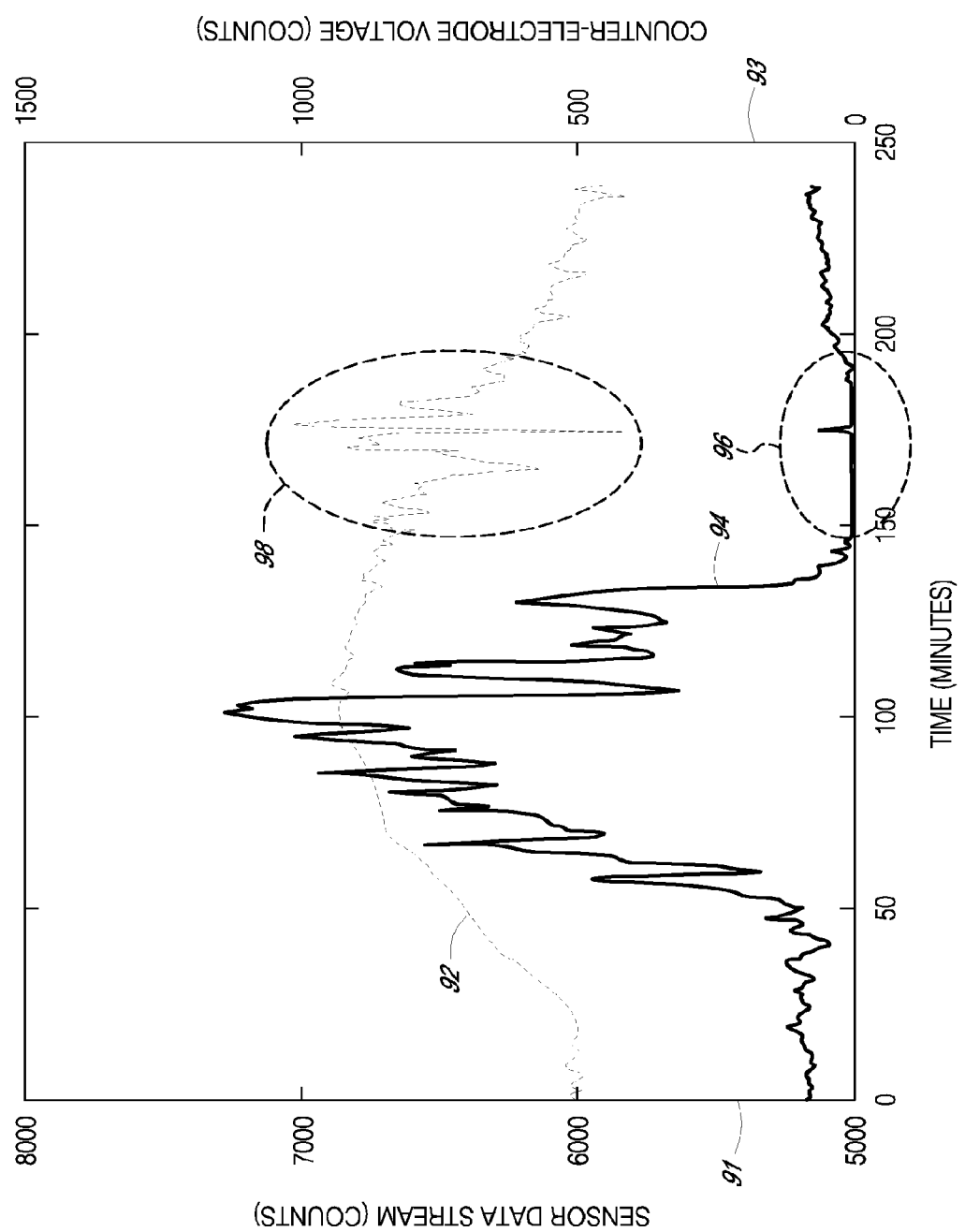
FIG. 9 is a graph that illustrates the correlation between the counter electrode voltage and signal artifacts in a data stream from a glucose sensor in one embodiment.

FIG. 9 is a graph that shows a comparison of sensor current and counter-electrode voltage in a host over time. The x-axis represents time in minutes. The first y-axis 91 represents sensor counts from the working electrode and thus plots a raw sensor data stream 92 for the glucose sensor over a period of time. The second y-axis 93 represents counter-electrode voltage 94 in counts. The graph illustrates the correlation between sensor data 92 and counter-electrode voltage 94; particularly, that erroneous counter electrode function 96 where the counter voltages drops approximately to zero substantially coincides with transient non-glucose related signal artifacts 98. In other words, when counter-electrode voltage is at or near zero, sensor data includes signal artifacts.

In another embodiment of ischemia detection, wherein the glucose sensor is an electrochemical sensor and contains a two- or three-cell electrochemical cell, signal artifacts are detected by monitoring the reference electrode. This "reference drift detection" embodiment takes advantage of the fact that the reference electrode will vary or drift in order to maintain a stable bias potential with the working electrode, such as described in more detail herein. This "drifting" generally indicates non-glucose reaction rate-limiting noise, for example due to ischemia. It is noted that the following example describes an embodiment wherein the sensor includes a working, reference, and counter electrodes, such as described in more detail elsewhere herein; however the principles of this embodiment are applicable to a two-cell (e.g., anode and cathode) electrochemical cell as is understood in the art.

Figure 10A:
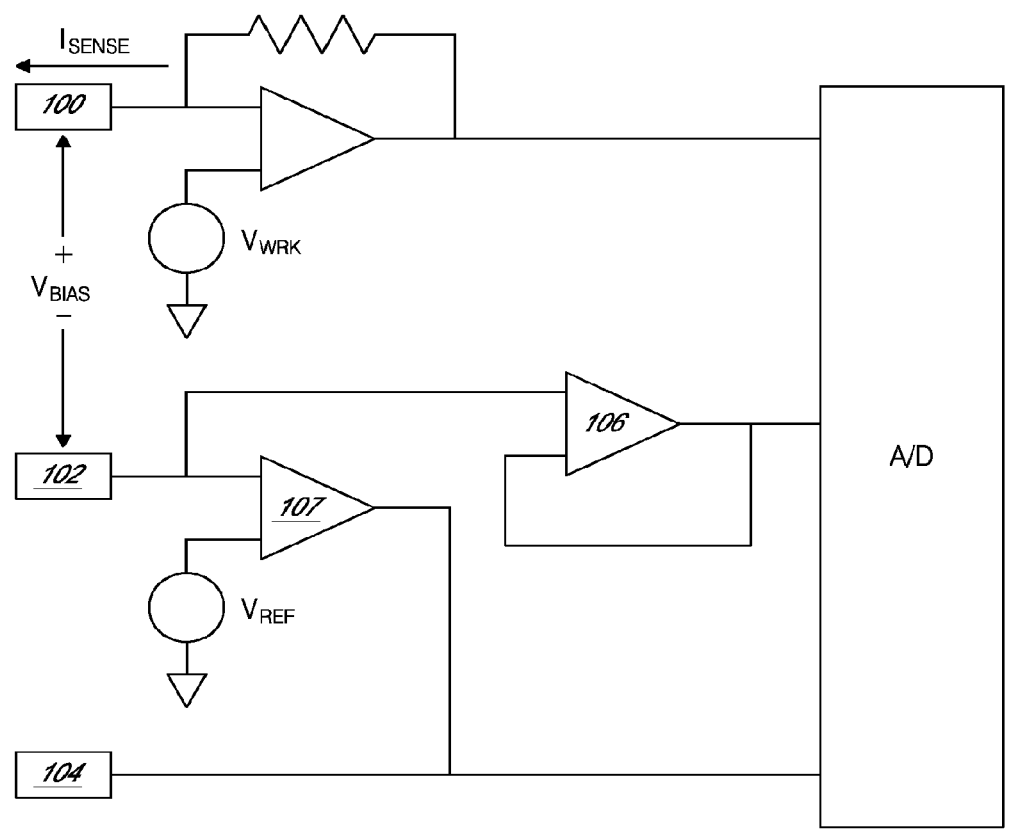
FIG. 10A is a circuit diagram of a potentiostat that controls a typical three-electrode system in one embodiment.

FIG. 10A is a circuit diagram of a potentiostat that controls a typical three-electrode system, which can be employed with a glucose sensor 10 such as described with reference to FIGS. 1 and 2. The potentiostat includes a working electrode 100, a reference electrode 102, and a counter electrode 104. The voltage applied to the working electrode is a constant value (e.g., +1.2V) and the voltage applied to the reference electrode is also set at a constant value (e.g., +0.6V) such that the potential ($V_{BIAS}$) applied between the working and reference electrodes is maintained at a constant value (e.g., +0.6V). The counter electrode is configured to have a constant current (equal to the current being measured by the working electrode), which is accomplished by varying the voltage at the counter electrode in order to balance the current going through the working electrode 100 such that current does not pass through the reference electrode 102. A negative feedback loop 107 is constructed from an operational amplifier (OP AMP), the reference electrode 102, the counter electrode 104, and a reference potential, to maintain the reference electrode at a constant voltage.

In practice, a glucose sensor of one embodiment comprises a membrane that contains glucose oxidase that catalyzes the conversion of oxygen and glucose to hydrogen peroxide and gluconate, such as described with reference to FIGS. 1 and 2. Therefore for each glucose molecule metabolized there is a change equivalent in molecular concentration in the co-reactant $O_2$ and the product $H_2O_2$. Consequently, one can use an electrode (e.g., working electrode 100) to monitor the concentration-induced current change in either the co-reactant or the product to determine glucose concentration.

One limitation of the electrochemistry is seen when insufficient negative voltage is available to the counter electrode 104 to balance the working electrode 100. This limitation can occur when insufficient oxygen is available to the counter electrode 104 for reduction, for example. When this limitation occurs, the counter electrode can no longer vary its voltage to maintain a balanced current with the working electrode and thus the negative feedback loop 107 used to maintain the reference electrode is compromised. Consequently, the reference electrode voltage will change or "drift," altering the applied bias potential (i.e., the potential applied between the working and reference electrodes), thereby decreasing the applied bias potential. When this change in applied bias potential occurs, the working electrode can produce erroneous glucose measurements due to either increased or decreased signal strength ($I_{SENSE}$).

Figure 10B:
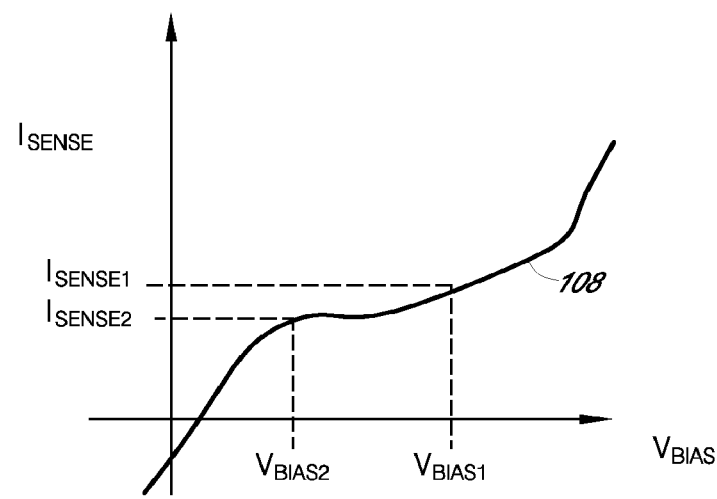
FIG. 10B is a diagram known as Cyclic-Voltammetry (CV) curve, which illustrates the relationship between applied potential ($V_{BIAS}$) and signal strength of the working electrode ($I_{SENSE}$) and can be used to detect signal artifacts.

FIG. 10B a diagram referred to as Cyclic-Voltammetry (CV) curve, wherein the x-axis represents the applied potential ($V_{BIAS}$) and the y-axis represents the signal strength of the working electrode ($I_{SENSE}$). A curve 108 illustrates an expected CV curve when the potentiostat is functioning normally. Typically, desired bias voltage can be set (e.g., $V_{BIAS1}$) and a resulting current will be sensed (e.g., $I_{SENSE1}$). As the voltage decreases (e.g., $V_{BIAS2}$) due to reference voltage drift, for example, a new resulting current is sensed (e.g., $I_{SENSE2}$). Therefore, the change in bias is an indicator of signal artifacts and can be used in signal estimation and to replace the erroneous resulting signals. In addition to ischemia, the local environment at the electrode surfaces can affect the CV curve, for example, changes in pH, temperature, and other local biochemical species can significantly alter the location of the CV curve.

Figure 10C:
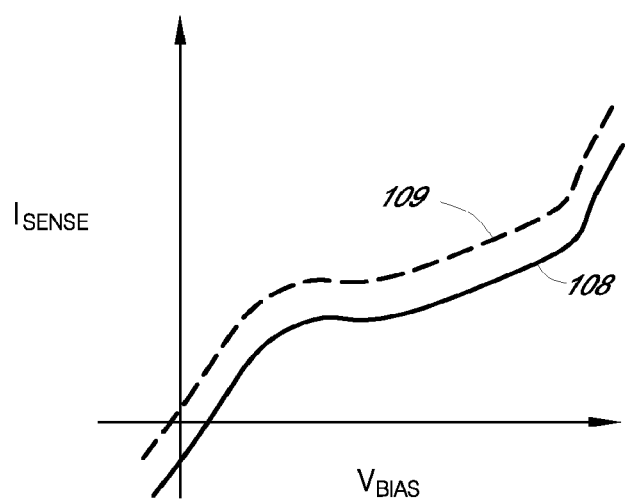
FIG. 10C is a diagram showing a CV curve that illustrates an alternative embodiment of signal artifacts detection, wherein pH and/or temperature can be monitoring using the CV curve.

FIG. 10C is a CV curve that illustrates an alternative embodiment of signal artifacts detection, wherein pH and/or temperature can be monitoring using the CV curve and diagnosed to detect transient non-glucose related signal artifacts. For example, signal artifacts can be attributed to thermal changes and/or pH changes in some embodiments because certain changes in pH and temperature affect data from a glucose sensor that relies on an enzymatic reaction to measure glucose. Signal artifacts caused by pH changes, temperature changes, changes in available electrode surface area, and other local biochemical species can be detected and signal estimation can be applied an/or optimized such as described in more detail elsewhere herein. In FIG. 10C, a first curve 108 illustrates an expected CV curve when the potentiostat is functioning normally. A second curve 109 illustrates a CV curve wherein the environment has changed as indicated by the upward shift of the CV curve.

In some embodiments, pH and/or temperature measurements are obtained proximal to the glucose sensor; in some embodiments, pH and/or temperature measurements are also obtained distal to the glucose sensor and the respective measurements compared, such as described in more detail above with reference to oxygen sensors.

In another implementation of signal artifacts detection, wherein temperature is detected, an electronic thermometer can be proximal to or within the glucose sensor, such that the temperature measurement is representative of the temperature of the glucose sensor's local environment. It is noted that accurate sensor function depends on diffusion of molecules from the blood to the interstitial fluid, and then through the membranes of the device to the enzyme membrane. Additionally, diffusion transport of hydrogen peroxide from the enzyme membrane to the electrode occurs. Therefore, temperatures can be a rate determining parameter of diffusion. As temperature decreases, diffusion transport decreases. Under certain human conditions, such as hypothermia or fever, the variations can be considerably greater. Additionally, under normal conditions, the temperature of subcutaneous tissue is known to vary considerably more than core tissues (e.g., core temperature). Temperature thresholds can be set to detect signal artifacts accordingly.

In another implementation, a pH detector is used to detect signal artifacts. In glucose sensors that rely on enzymatic reactions, a pH of the fluid to be sensed can be within the range of about 5.5 to 7.5. Outside of this range, effects may be seen in the enzymatic reaction and therefore data output of the glucose sensor. Accordingly, by detecting if the pH is outside of a predetermined range (e.g., 5.5 to 7.5), a pH detector may detect transient non-glucose related signal artifacts such as described herein. It is noted that the pH threshold can be set at ranges other than provided herein without departing from the preferred embodiments.

In an alternative embodiment of signal artifacts detection, pressure and/or stress can be monitored using known techniques for example by a strain gauge placed on the sensor that detects stress/strain on the circuit board, sensor housing, or other components. A variety of microelectromechanical systems (MEMS) can be utilized to measure pressure and/or stress within the sensor.

In another alternative embodiment of signal artifacts detection, the microprocessor in the sensor (or receiver) periodically evaluates the data stream for high amplitude noise, which is defined by noisy data wherein the amplitude of the noise is above a predetermined threshold. For example, in the graph of FIGS. 7A and 7B, the system noise sections such as 72a and 72b have a substantially low amplitude noise threshold; in contrast to system noise, signal artifacts sections such as 74a and 74b have signal artifacts (noise) with an amplitude that is much higher than that of system noise. Therefore, a threshold can be set at or above the amplitude of system noise, such that when noisy data is detected above that amplitude, it can be considered "signal artifacts" as defined herein.

In another alternative embodiment of signal artifacts detection, a method hereinafter referred to as the "Cone of Possibility Detection Method," utilizes physiological information along with glucose signal values in order define a "cone" of physiologically feasible glucose signal values within a human, such that signal artifacts are detected whenever the glucose signal falls outside of the cone of possibility. Particularly, physiological information depends upon the physiological parameters obtained from continuous studies in the literature as well as our own observations. A first physiological parameter uses a maximal sustained rate of change of glucose in humans (e.g., about 4 to 5 mg/dL/min) and a maximum acceleration of that rate of change (e.g., about 0.1 to 0.2 mg/dL/min$^2$). A second physiological parameter uses the knowledge that rate of change of glucose is lowest at the minima, which is the areas of greatest risk in patient treatment, and the maxima, which has the greatest long-term effect on secondary complications associated with diabetes. A third physiological parameter uses the fact that the best solution for the shape of the curve at any point along the curve over a certain time period (e.g., about 20-30 minutes) is a straight line. Additional physiological parameters can be incorporated and are within the scope of this embodiment.

In practice, the Cone of Possibility Detection Method combines any one or more of the above-described physiological parameters to form an algorithm that defines a cone of possible glucose levels for glucose data captured over a predetermined time period. In one exemplary implementation of the Cone of Possibility Detection Method, the system (microprocessor in the sensor or receiver) calculates a maximum physiological rate of change and determines if the data falls within these physiological limits; if not, signal artifacts are identified. It is noted that the maximum rate of change can be narrowed (e.g., decreased) in some instances. Therefore, additional physiological data could be used to modify the limits imposed upon the Cone of Possibilities Detection Method for sensor glucose values. For example, the maximum per minute rate change can be lower when the subject is sleeping or hasn't eaten in eight hours; on the other hand, the maximum per minute rate change can be higher when the subject is exercising or has consumed high levels of glucose, for example. In general, it has been observed that rates of change are slowest near the maxima and minima of the curve, and that rates of change are highest near the midpoint between the maxima and minima. It should further be noted that rate of change limits are derived from analysis of a range of data significantly higher unsustained rates of change can be observed.

In another alternative embodiment of signal artifacts detection, examination of the spectral content (e.g., frequency content) of the data stream can yield measures useful in detecting signal artifacts. For example, data that has high frequency, and in some cases can be characterized by a large negative slope, are indicative of signal artifacts and can cause sensor signal loss. Specific signal content can be monitored using an orthogonal transform, for example a Fourier transform, a Discrete Fourier Transform (DFT), or any other method known in the art.

Figure 11:
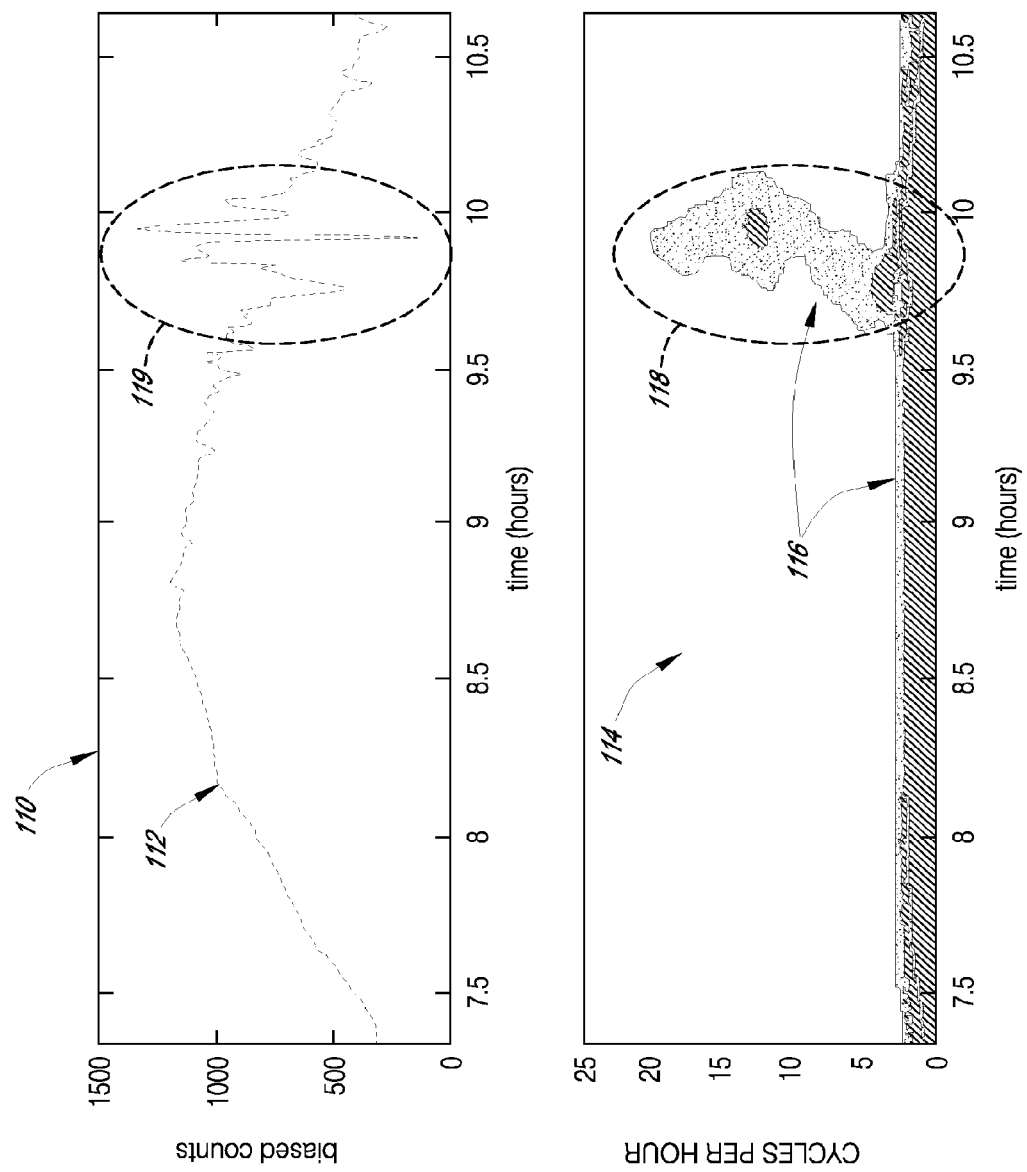
FIG. 11 is a graph and spectrogram that illustrate the correlation between high frequency and signal artifacts observed by monitoring the frequency content of a data stream in one embodiment.

FIG. 11 is a graph of 110 a raw data stream from a glucose sensor and a spectrogram 114 that shows the frequency content of the raw data stream in one embodiment. Particularly, the graph 110 illustrates the raw data stream 112 and includes an x-axis that represents time in hours and a y-axis that represents sensor data output in counts; the spectrogram 114 illustrates the frequency content 116 corresponding to the raw data stream 112 and includes an x-axis that represents time in hours corresponding to the x-axis of the graph 110 and a y-axis that represents frequency content in cycles per hour. The darkness of each point represents the amplitude of that frequency at that time. Darker points relate to higher amplitudes. Frequency content on the spectrogram 114 was obtained using a windowed Discrete Fourier transform.

The raw data stream in the graph 110 has been adjusted by a linear mapping similar to the calibration algorithm. In this example, the bias (or intercept) has been adjusted but not the proportion (or slope). The slope of the raw data stream would typically be determined by some calibration, but since the calibration has not occurred in this example, the gray levels in the spectrogram 114 indicate relative values. The lower values of the graph 110 are white. They are colored as white below a specific value, highlighting only the most intense areas of the graph.

By monitoring the frequency content 116, high frequency cycles 118 can be observed. The high frequency cycles 118 correspond to signal artifacts 119 such as described herein. Thus, signal artifacts can be detected on a data stream by monitoring frequency content and setting a threshold (e.g., 30 cycles per hour). The set threshold can vary depending on the signal source.

In another alternative embodiment of signal artifacts detection, examination of the signal information content can yield measures useful in detecting signal artifacts. Time series analysis can be used to measure entropy, approximate entropy, variance, and/or percent change of the information content over consecutive windows (e.g., 30 and 60 minute windows of data) of the raw data stream. In one exemplary embodiment, the variance of the raw data signal is measured over 15 minute and 45 minute windows, and signal artifacts are detected when the variance of the data within the 15-minute window exceeds the variance of the data within the 45-minute window.

One or a plurality of the above signal artifacts detection models can be used alone or in combination to detect signal artifacts such as described herein. Accordingly, the data stream associated with the signal artifacts can be discarded, replaced, or otherwise processed in order to reduce or eliminate these signal artifacts and thereby improve the value of the glucose measurements that can be provided to a user.

Signal Artifacts Replacement

Signal Artifacts Replacement, such as described above, can use systems and methods that reduce or replace these signal artifacts that can be characterized by transience, high frequency, high amplitude, and/or substantially non-linear noise. Accordingly, a variety of filters, algorithms, and other data processing are provided that address the detected signal artifacts by replacing the data stream, or portion of the data stream, with estimated glucose signal values. It is noted that "signal estimation" as used herein, is a broad term, which includes filtering, data smoothing, augmenting, projecting, and/or other algorithmic methods that estimate glucose signal values based on present and historical data.

It is noted that a glucose sensor can contain a microprocessor or the like that processes periodically received raw sensor data (e.g., every 30 seconds). Although a data point can be available constantly, for example by use of an electrical integration system in a chemo-electric sensor, relatively frequent (e.g., every 30 seconds), or less frequent data point (e.g., every 5 minutes), can be more than sufficient for patient use. It is noted that accordingly Nyquist Theory, a data point is required about every 10 minutes to accurately describe physiological change in glucose in humans. This represents the lowest useful frequency of sampling. However, it should be recognized that it is desirable to sample more frequently than the Nyquist minimum, to provide for sufficient data in the event that one or more data points are lost, for example. Additionally, more frequently sampled data (e.g., 30-second) can be used to smooth the less frequent data (e.g., 5-minute) that are transmitted. It is noted that in this example, during the course of a 5-minute period, 10 determinations are made at 30-second intervals.

In some embodiments of Signal Artifacts Replacement, signal estimation can be implemented in the sensor and transmitted to a receiver for additional processing. In some embodiments of Signal Artifacts Replacement, raw data can be sent from the sensor to a receiver for signal estimation and additional processing therein. In some embodiments of Signal Artifacts Replacement, signal estimation is performed initially in the sensor, with additional signal estimation in the receiver.

In some embodiments of Signal Artifacts Replacement, wherein the sensor is an implantable glucose sensor, signal estimation can be performed in the sensor to ensure a continuous stream of data. In alternative embodiments, data can be transmitted from the sensor to the receiver, and the estimation performed at the receiver; It is noted however that there can be a risk of transmit-loss in the radio transmission from the sensor to the receiver when the transmission is wireless. For example, in embodiments wherein a sensor is implemented in vivo, the raw sensor signal can be more consistent within the sensor (in vivo) than the raw signal transmitted to a source (e.g., receiver) outside the body (e.g., if a patient were to take the receiver off to shower, communication between the sensor and receiver can be lost and data smoothing in the receiver would halt accordingly). Consequently, It is noted that a multiple point data loss in the filter can take for example, about 25 to about 40 minutes for the data to recover to near where it would have been had there been no data loss.

In some embodiments of Signal Artifacts Replacement, signal estimation is initiated only after signal artifacts are positively detected, and stopped once signal artifacts are negligibly detected. In some alternative embodiments signal estimation is initiated after signal artifacts are positively detected and then stopped after a predetermined time period. In some alternative embodiments, signal estimation can be continuously or continually performed. In some alternative embodiments, one or more forms of signal estimation can be accomplished based on the severity of the signal artifacts, such as will be described with reference the section entitled, "Selective Application of Signal Artifacts Replacement."

In some embodiments of Signal Artifacts Replacement, the microprocessor performs a linear regression. In one such implementation, the microprocessor performs a linear regression analysis of the n (e.g., 10) most recent sampled sensor values to smooth out the noise. A linear regression averages over a number of points in the time course and thus reduces the influence of wide excursions of any point from the regression line. Linear regression defines a slope and intercept, which is used to generate a "Projected Glucose Value," which can be used to replace sensor data. This regression can be continually performed on the data stream or continually performed only during the transient signal artifacts. In some alternative embodiments, signal estimation can include non-linear regression.

In another embodiment of Signal Artifacts Replacement, the microprocessor performs a trimmed regression, which is a linear regression of a trimmed mean (e.g., after rejecting wide excursions of any point from the regression line). In this embodiment, after the sensor records glucose measurements at a predetermined sampling rate (e.g., every 30 seconds), the sensor calculates a trimmed mean (e.g., removes highest and lowest measurements from a data set and then regresses the remaining measurements to estimate the glucose value.

Figure 12:
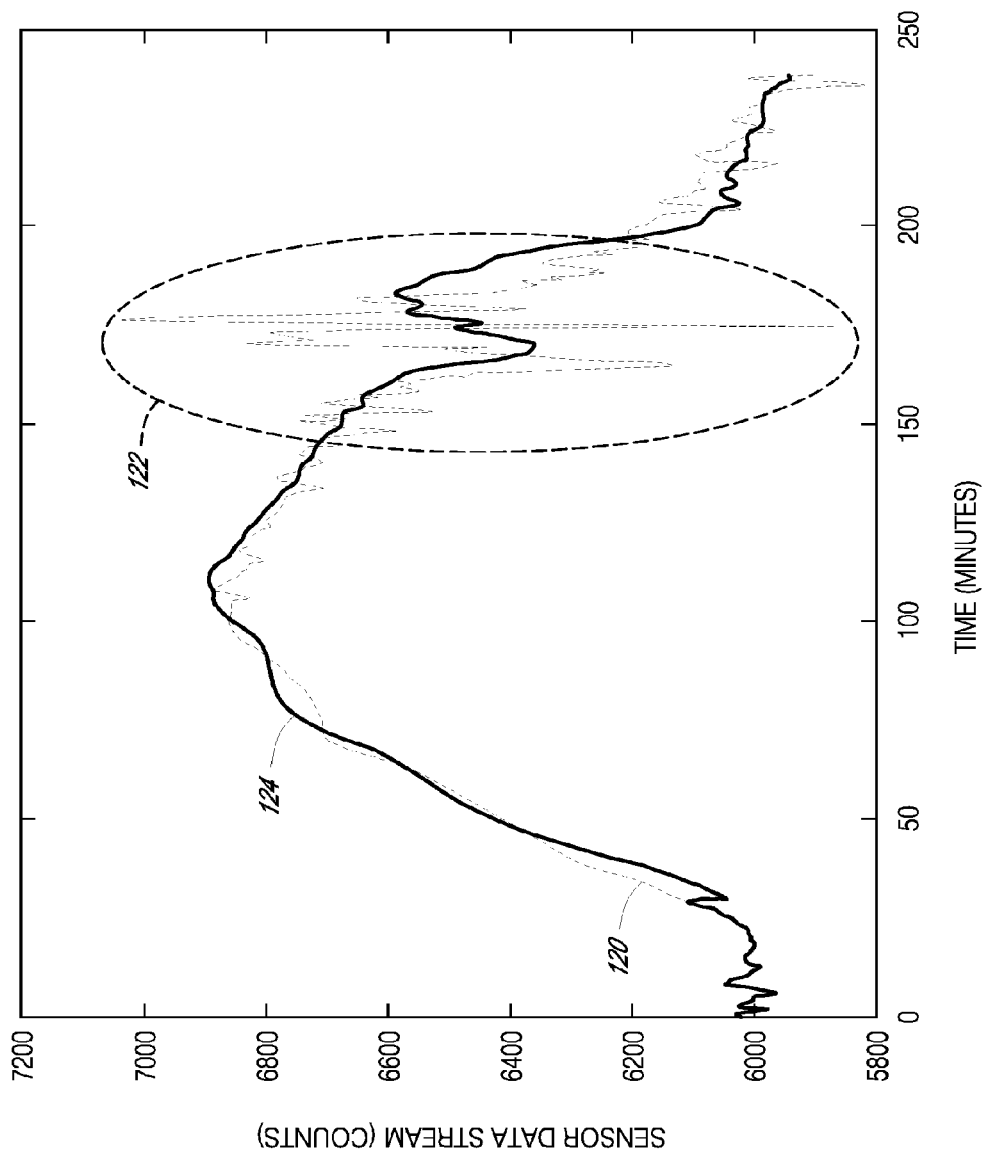
FIG. 12 is a graph that illustrates a data stream obtained from a glucose sensor and a signal smoothed by trimmed linear regression that can be used to replace some of or the entire raw data stream in one embodiment.

FIG. 12 is a graph that illustrates a raw data stream from a glucose sensor and a trimmed regression that can be used to replace some of or the entire data stream. The x-axis represents time in minutes; the y-axis represents sensor data output in counts. A raw data signal 120, which is illustrated as a dotted line, shows a data stream wherein some system noise can be detected, however signal artifacts 122 can be particularly seen in a portion thereof (and can be detected by methods such as described above). The trimmed regression line 124, which is illustrated as a solid line, is the data stream after signal estimation using a trimmed linear regression algorithm, such as described above, and appears at least somewhat "smoothed" on the graph. In this particular example, the trimmed regression uses the most recent 60 points (30 minutes) and trims out the highest and lowest values, then uses the leftover 58 points to project the next point. It is noted that the trimmed regression 124 provides a good estimate throughout the majority data stream, however is only somewhat effective in smoothing the data in during signal artifacts 122. To provide an optimized estimate of the glucose data values, the trimmed regression can be optimized by changing the parameters of the algorithm, for example by trimming more or less raw glucose data from the top and/or bottom of the signal artifacts 122 prior to regression. Additionally It is noted that trimmed regression, because of its inherent properties, can be particularly suited for noise of a certain amplitude and/or characteristic. In one embodiment, for example trimmed regression can be selectively applied based on the severity of the signal artifacts, which is described in more detail below with reference to FIGS. 15 to 17.

In another embodiment of Signal Artifacts Replacement, the microprocessor runs a non-recursive filter, such as a finite impulse response (FIR) filter. A FIR filter is a digital signal filter, in which every sample of output is the weighted sum of past and current samples of input, using only some finite number of past samples.

Figure 13:
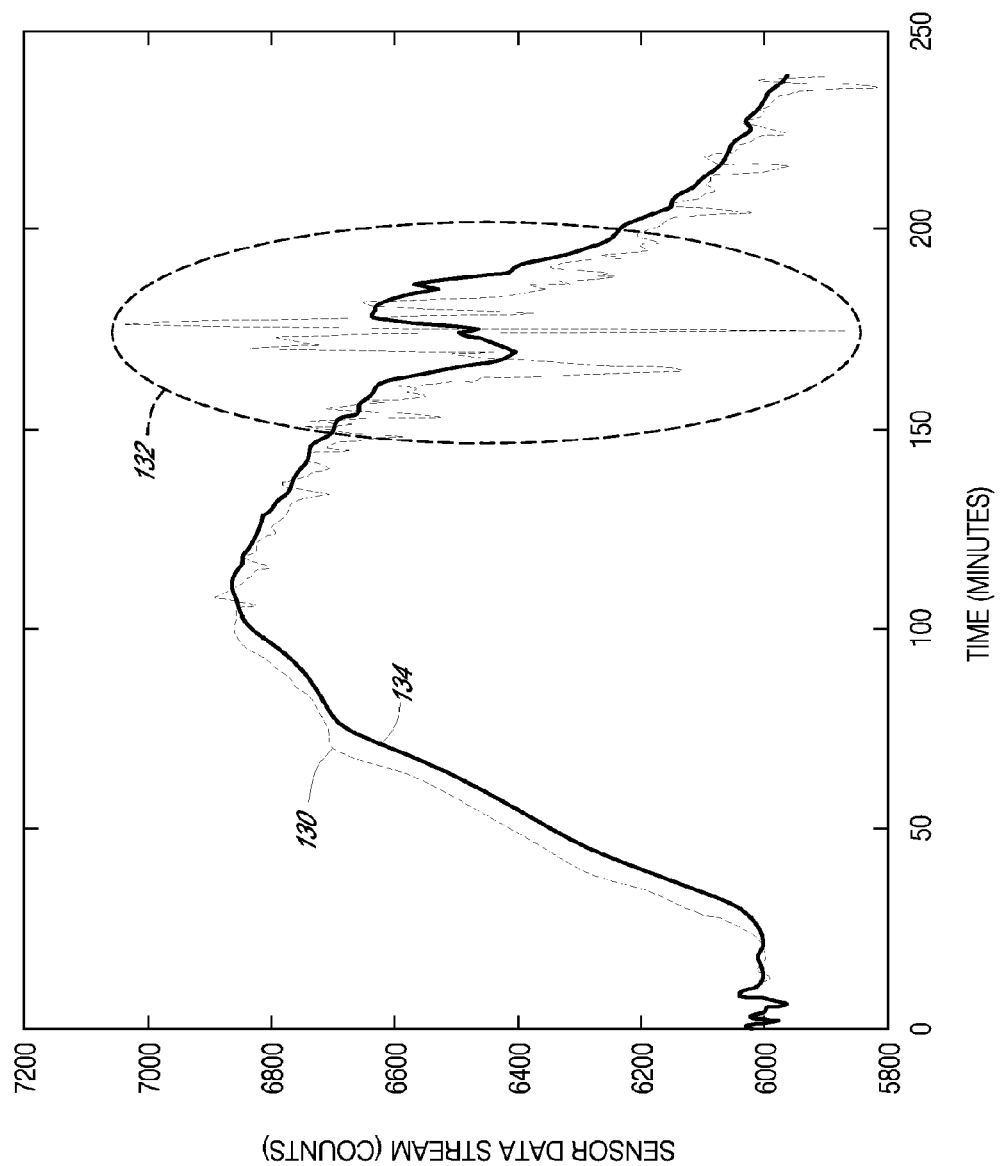
FIG. 13 is a graph that illustrates a data stream obtained from a glucose sensor and a FIR-smoothed data signal that can be used to replace some of or the entire raw data stream in one embodiment.

FIG. 13 a graph that illustrates a raw data stream from a glucose sensor and an FIR-estimated signal that can be used to replace some of or the entire data stream. The x-axis represents time in minutes; the y-axis represents sensor data output in counts. A raw data signal 130, which is illustrated as a dotted line, shows a data stream wherein some system noise can be detected, however signal artifacts 132 can be particularly seen in a portion thereof (and can be detected by methods such as described above). The FIR-estimated signal 134, which is illustrated as a solid line, is the data stream after signal estimation using a FIR filter, such as described above, and appears at least somewhat "smoothed" on the graph. It is noted that the FIR-estimated signal provides a good estimate throughout the majority of the data stream, however like trimmed regression it is only somewhat effective in smoothing the data during signal artifacts 132. To provide an optimized estimate of the glucose data values, the FIR filter can be optimized by changing the parameters of the algorithm, for example the tuning of the filter, particularly the frequencies of the pass band and the stop band. Additionally It is noted that the FIR filter, because of its inherent properties, can be particularly suited for noise of a certain amplitude and/or characteristic. In one embodiment, for example the FIR filter can be selectively applied based on the severity of the signal artifacts, which is described in more detail below with reference to FIGS. 15 to 17. It is noted that the FIR-estimated signal induces a time lag on the data stream, which can be increased or decreased in order to optimize the filtering or to minimize the time lag, for example.

In another embodiment of Signal Artifacts Replacement, the microprocessor runs a recursive filter, such as an infinite impulse response (IIR) filter. An IIR filter is a type of digital signal filter, in which every sample of output is the weighted sum of past and current samples of input. In one exemplary implementation of an IIR filter, the output is computed using 6 additions/subtractions and 7 multiplications as shown in the following equation:

$$y(n) = \frac{a_0 * x(n) + a_1 * x(n-1) + a_2 * x(n-2) + a_3 * x(n-3) - b_1 * y(n-1) - b_2 * y(n-2) - b_3 * y(n-3)}{b_0}$$

This polynomial equation includes coefficients that are dependent on sample rate and frequency behavior of the filter. Frequency behavior passes low frequencies up to cycle lengths of 40 minutes, and is based on a 30 second sample rate. In alternative implementations, the sample rate and cycle lengths can be more or less. See Lynn "Recursive Digital Filters for Biological Signals" Med. & Biol. Engineering, Vol. 9, pp. 37-43, which is incorporated herein by reference in its entirety.

Figure 14:
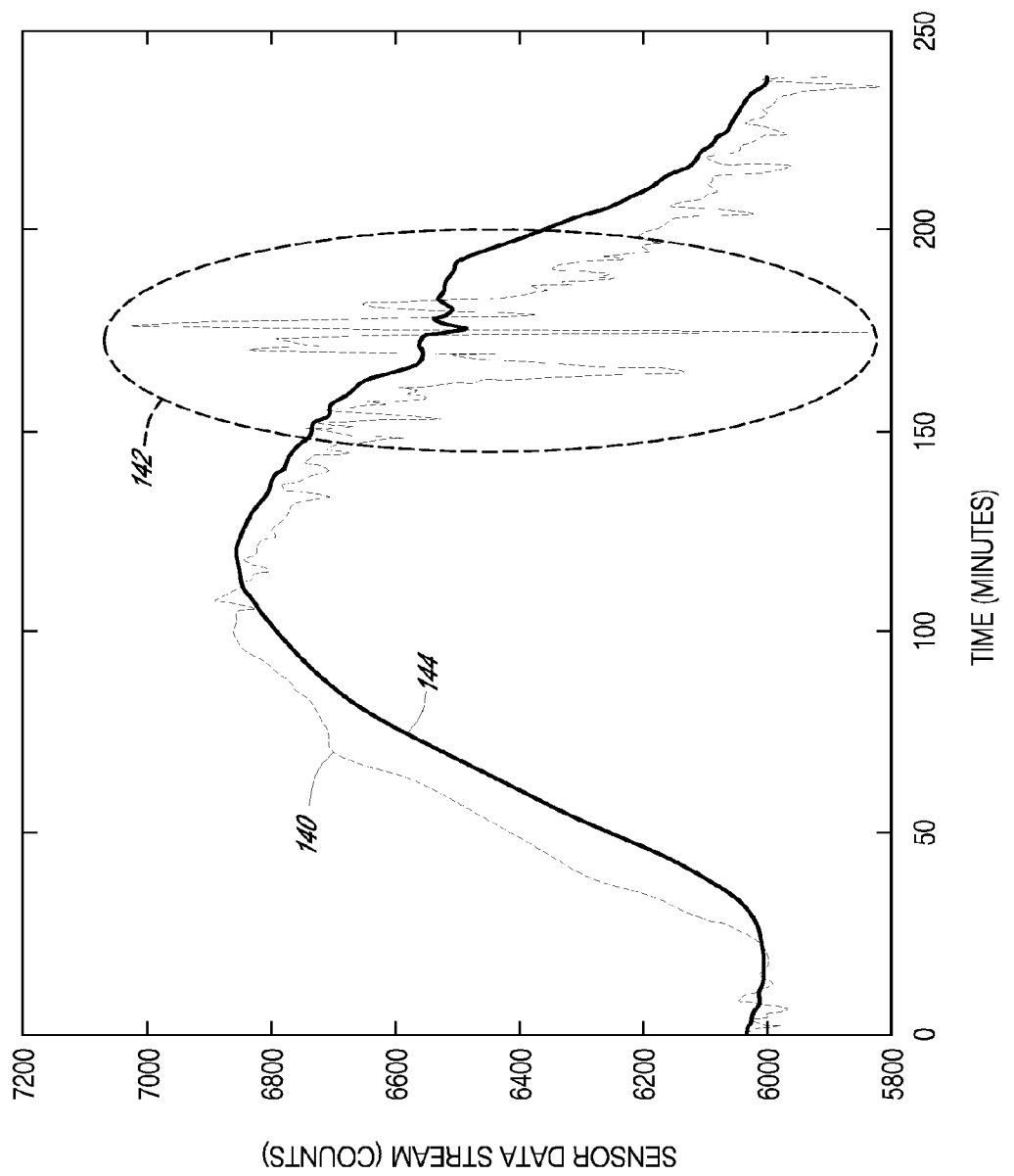
FIG. 14 is a graph that illustrates a data stream obtained from a glucose sensor and an IIR-smoothed data signal that can be used to replace some of or the entire raw data stream in one embodiment.

FIG. 14 is a graph that illustrates a raw data stream from a glucose sensor and an IIR-estimated signal that can be used to replace some of or the entire data stream. The x-axis represents time in minutes; the y-axis represents sensor data output in counts. A raw data signal 140, which is illustrated as a dotted line, shows a data stream wherein some system noise can be detected, however signal artifacts 142 can be particularly seen in a portion thereof (and can be detected by methods such as described above). The IIR-estimated signal 144, which is illustrated as a solid line, represents the data stream after signal estimation using an IIR filter, such as described above, and appears at least somewhat "smoothed" on the graph. It is noted that the IIR-estimated signal induces a time lag on the data stream, however it appears to be a particularly good estimate of glucose data values during signal artifacts 142, as compared to the FIR filter (FIG. 13), for example.

To optimize the estimation of the glucose data values, the parameters of the IIR filter can be optimized, for example by increasing or decreasing the cycle lengths (e.g., 10 minutes, 20 minute, 40 minutes, 60 minutes) that are used in the algorithm. Although an increased cycle length can increase the time lag induced by the IIR filter, an increased cycle length can also better estimate glucose data values during severe signal artifacts. In other words, It is noted that the IIR filter, because of its inherent properties, can be particularly suited for noise of a certain amplitude and/or characteristic. In one exemplary embodiment, the IIR filter can be continually applied, however the parameters such as described above can be selectively altered based on the severity of the signal artifacts; in another exemplary embodiment, the IIR filter can be applied only after positive detection of signal artifacts. Selective application of the IIR filter based on the severity of the signal artifacts is described in more detail below with reference to FIGS. 15 to 17.

It is noted that a comparison of linear regression, an FIR filter, and an IIR filter can be advantageous for optimizing their usage in the preferred embodiments. That is, an understanding the design considerations for each algorithm can lead to optimized selection and implementation of the algorithm, as described in the section entitled, "Selective Application of Signal Replacement Algorithms" herein. During system noise, as defined herein, all of the above algorithms can be successfully implemented during system noise with relative ease. During signal artifacts, however, computational efficiency is greater with an IIR-filter as compared with linear regression and FIR-filter. Additionally, although the time lag associated with an IIR filter can be substantially greater than that of the linear regression or FIR-filter, this can be advantageous during severe signal artifacts in order to assign greater weight toward the previous, less noisy data in signal estimation.

In another embodiment of Signal Artifacts Replacement, the microprocessor runs a maximum-average (max-average) filtering algorithm. The max-average algorithm smoothes data based on the discovery that the substantial majority of signal artifacts observed after implantation of glucose sensors in humans, for example, is not distributed evenly above and below the actual blood glucose levels. It has been observed that many data sets are actually characterized by extended periods in which the noise appears to trend downwardly from maximum values with occasional high spikes such as described in more detail above with reference to FIG. 7B, section 74b, which is likely in response to limitations in the system that do not allow he glucose to fully react at the enzyme layer and/or proper reduction of $H_2O_2$ at the counter electrode, for example. To overcome these downward trending signal artifacts, the max-average calculation tracks with the highest sensor values, and discards the bulk of the lower values. Additionally, the max-average method is designed to reduce the contamination of the data with unphysiologically high data from the high spikes.

The max-average calculation smoothes data at a sampling interval (e.g., every 30 seconds) for transmission to the receiver at a less frequent transmission interval (e.g., every 5 minutes) to minimize the effects of low non-physiological data. First, the microprocessor finds and stores a maximum sensor counts value in a first set of sampled data points (e.g., 5 consecutive, accepted, thirty-second data points). A frame shift time window finds a maximum sensor counts value for each set of sampled data (e.g., each 5-point cycle length) and stores each maximum value. The microprocessor then computes a rolling average (e.g., 5-point average) of these maxima for each sampling interval (e.g., every 30 seconds) and stores these data. Periodically (e.g., every $10^{th}$ interval), the sensor outputs to the receiver the current maximum of the rolling average (e.g., over the last 10 thirty-second intervals as a smoothed value for that time period (e.g., 5 minutes)). In one example implementation, a 10-point window can be used, and at the $10^{th}$ interval, the microprocessor computes the average of the most recent 5 or 10 average maxima as the smoothed value for a 5 minute time period.

In some embodiments of the max-average algorithm, an acceptance filter can also be applied to new sensor data to minimize effects of high non-physiological data. In the acceptance filter, each sampled data point (e.g., every 30-seconds) is tested for acceptance into the maximum average calculation. Each new point is compared against the most representative estimate of the sensor curve at the previous sampling interface (e.g., 30-second time point), or at a projection to a current estimated value. To reject high data, the current data point is compared to the most recent value of the average maximum values over a time period (e.g., 5 sampled data points over a 2.5 minute period). If the ratio of current value to the comparison value is greater than a certain threshold (e.g., about 1.02), then the current data point is replaced with a previously accepted value (e.g., 30-second value). If the ratio of current value to the comparison value is in at or within a certain range (e.g., about 1.02 to 0.90), then the current data point is accepted. If the ratio of current value to the comparison value is less than a certain threshold (e.g., about 0.90), then the current data point is replaced with a previously accepted value. The acceptance filter step and max-average calculation are continuously run throughout the data set (e.g., fixed 5-minute windows) on a rolling window basis (e.g., every 30 seconds).

In some implementations of the acceptance filter, the comparison value for acceptance could also be the most recent maximum of 5 accepted sensor points (more sensitive) or the most recent average over 10 averages of 5 maximum values (least sensitive), for example. In some exemplary implementations of the acceptance filter, the projected value for the current time point can be based on regression of the last 4 accepted 30-second values and/or the last 2 to 4 (5 to 15 min) of the 5-minute smoothed values, for example. In some exemplary implementations of the acceptance filter, the percentage comparisons of +2% and -10% of counts value would be replaced by percentage comparisons based on the most recent 24 hour range of counts values; this method would provide improved sensor specificity as compared to a method based on total counts.

In another embodiment of Signal Artifacts Replacement, the microprocessor runs a "Cone of Possibility Replacement Method." It is noted that this method can be performed in the sensor and/or in the receiver. The Cone of Possibility Detection Method utilizes physiological information along with glucose signal values in order define a "cone" of physiologically feasible glucose signal values within a human. Particularly, physiological information depends upon the physiological parameters obtained from continuous studies in the literature as well as our own observations. A first physiological parameter uses a maximal sustained rate of change of glucose in humans (e.g., about 4 to 5 mg/dl/min) and a maximum sustained acceleration of that rate of change (e.g., about 0.1 to 0.2 mg/min/min). A second physiological parameter uses the knowledge that rate of change of glucose is lowest at the maxima and minima, which are the areas of greatest risk in patient treatment, such as described with reference to Cone of Possibility Detection, above. A third physiological parameter uses the fact that the best solution for the shape of the curve at any point along the curve over a certain time period (e.g., about 20-25 minutes) is a straight line. It is noted that the maximum rate of change can be narrowed in some instances. Therefore, additional physiological data can be used to modify the limits imposed upon the Cone of Possibility Replacement Method for sensor glucose values. For example, the maximum per minute rate change can be lower when the subject is lying down or sleeping; on the other hand, the maximum per minute rate change can be higher when the subject is exercising, for example.

The Cone of Possibility Replacement Method utilizes physiological information along with blood glucose data in order to improve the estimation of blood glucose values within a human in an embodiment of Signal Artifacts Replacement. The Cone of Possibility Replacement Method can be performed on raw data in the sensor, on raw data in the receiver, or on smoothed data (e.g., data that has been replaced/estimated in the sensor or receiver by one of the methods described above) in the receiver.

In a first implementation of the Cone of Possibility Replacement Method, a centerline of the cone can be projected from a number of previous, optionally smoothed, incremental data points (e.g., previous four, 5-minute data points). Each predicted cone centerline point (e.g., 5 minute point) increases by the slope (S) (e.g., for the regression in counts/minute) multiplied by the data point increment (e.g., 5 minutes). Counts/mg/dL is estimated from glucose and sensor range calculation over the data set.

In this first implementation of the Cone of Possibility Replacement Method, positive and negative cone limits are simple linear functions. Periodically (e.g., every 5 minutes), each sensor data point (optionally smoothed) is compared to the cone limits projected from the last four points. If the sensor value observed is within the cone limits, the sensor value is retained and used to generate the cone for the next data point increment (e.g., 5-minute point). If the sensor value observed falls outside the high or low cone limit, the value is replaced by the cone limit value, and that value is used to project the next data point increment (e.g., 5 minute point, high point, or low point). For example, if the difference between two adjacent 5-minute points exceeds 20 mg/dL, then cone limits are capped at 20 mg/dL increments per 5 minutes, with the positive limit of the cone being generated by the addition of $0.5*A*t^2$ to mid cone value, where A is 0.1 mg/dL/min/min and t is 5 minute increments (A is converted to counts/min/min for the calculation), and the negative limit of the cone being generated by the addition of $-0.5*A*t^2$ to mid cone value. This implementation provides a high degree of accuracy and is minimally sensitive to non-physiological rapid changes.

The following table illustrates one example implementation of the Cone of Possibility Replacement Method, wherein the maximum sustained value observed for S is about +/−4 mg/dL/min and the maximum value observed for A is about +/−0.1 mg/dL/min$^2$:

| Time | Mid line (mg/dL) | Positive Cone Limit | Negative Cone Limit |
|---|---|---|---|
| 0 | 100 | 100 | 100 |
| 5 | 100 + 5*S | 100 + 5*S + 12.5*A | 100 + 5*S − 12.5A |
| 10 | 100 + 10*S | 100 + 10*S + 50*A | 100 + 10*S − 50*A |
| 15 | 100 + 15*S | 100 + 15*S + 112.5*A | 100 + 15*S − 112.5*A |
| 20 | 100 + 20*S | 100 + 20*S + 200*A | 100 + 20*S − 200*A |
| 25 | 100 + 25*S | 100 + 25*S + 312.5*A | 100 + 25*S − 312.5*A |

It is noted that the cone widens for each 5-minute increment for which a sensor value fails to fall inside the cone up to 30 minutes, such as can be seen in the table above. At 30 minutes, a cone has likely widened enough to capture an observed sensor value, which is used, and the cone collapses back to a 5-minute increment width. If no sensor values are captured within 30 minutes, the cone generation routine starts over using the next four observed points. In some implementations special rules can be applied, for example in a case where the change in counts in one 5-minute interval exceeds an estimated 30-mg/dL amount. In this case, the next acceptable point can be more than 20 to 30 minutes later. It is noted that an implementation of this algorithm includes utilizing the cone of possibility to predict glucose levels and alert patients to present or upcoming dangerous blood glucose levels.

In another alternative embodiment of cone widening, the cone can widen in set multiples (e.g., 20 mg/dL) of equivalent amounts for each additional time interval (e.g., 5 minutes), which rapidly widens the cone to accept data.

It is noted that the numerical parameters represent only one example implementation of the Cone of Possibility Replacement Method. The concepts can be applied to any numerical parameters as desired for various glucose sensor applications.

In another implementation of the Cone of Possibility Replacement Method, sensor calibration data is optimized using the Clarke Error Grid, the Consensus Grid, or an alternative error assessment that assigns risk levels based on the accuracy of matched data pairs. In an example using the Clarke Error Grid, because the 10 regions of the Clarke Error Grid are not all symmetric around the Y=X perfect regression, fits to the grid can be improved by using a multi-line regression to the data.

Accordingly the pivot point method for the counts vs. glucose regression fit can be used to optimize sensor calibration data to the Clarke Error Grid, Consensus Grid, or other clinical acceptability standard. First, the glucose range is divided according to meter values (e.g., at 200 mg/dL). Two linear fitting lines are used, which cross at the pivot point. The coordinates of the pivot point in counts and glucose value, plus the slope and intercept of the two lines are variable parameters. Some of pivot point coordinates (e.g., 4 out of 6) and slope or intercept of each line can be reset with each iteration, while the chosen coordinates define the remainder. The data are then re-plotted on the Clarke Error Grid, and changes in point placement and percentages in each region of the grid are evaluated. To optimize the fit of a data set to a Clark Error Grid, the regression of counts vs. reference glucose can be adjusted such that the maximum number of points are in the A+B zones without reducing the A+B percentage, and the number of points are optimized such that the highest percentage are in the A zone and lowest percentage are in the D, E and C zones. In general, the points should be distributed as evenly as possible around the Y=X line. In some embodiments, three distinct lines optimized for clinical acceptability can represent the regression line. In some embodiments, an additional useful criterion can be used to compute the root mean squared percentage bias for the data set. Better fits are characterized by reduction in the total root mean squared percentage bias. In an alternative implementation of the pivot point methods, a predetermined pivot (e.g., 10 degree) of the regression line can be applied when the estimated blood is above or below a set threshold (e.g., 150 mg/dL), wherein the pivot and threshold are determined from a retrospective analysis of the performance of a conversion function and its performance at a range of glucose concentrations.

In another embodiment of Signal Artifacts Replacement, reference changes in electrode potential can be used to estimate glucose sensor data during positive detection of signal artifacts from an electrochemical glucose sensor, the method hereinafter referred to as reference drift replacement. In this embodiment, the electrochemical glucose sensor comprises working, counter, and reference electrodes, such as described with reference to FIGS. 1, 2 and 10 above. This method exploits the function of the reference electrode as it drifts to compensate for counter electrode limitations during oxygen deficits, pH changes, and/or temperature changes such as described in more detail above with reference to FIGS. 10A, 10B, and 10C.

Such as described with in more detail with reference to FIG. 10A a potentiostat is generally designed so that a regulated potential difference between the reference electrode 102 and working electrode 100 is maintained as a constant. The potentiostat allows the counter electrode voltage to float within a certain voltage range (e.g., from between close to the +1.2V observed for the working electrode to as low as battery ground or 0.0V). The counter electrode voltage measurement will reside within this voltage range dependent on the magnitude and sign of current being measured at the working electrode and the electroactive species type and concentration available in the electrolyte adjacent to the counter electrode 104. This species will be electrochemically recruited (e.g., reduced/accepting electrons) to equal the current of opposite sign (e.g., oxidized/donating electrons) occurring at the working electrode 100. It has been discovered that the reduction of dissolved oxygen or hydrogen peroxide from oxygen converted in the enzyme layer are the primary species reacting at the counter electrode to provide this electronic current balance in this embodiment. If there are inadequate reducible species (e.g., oxygen) available for the counter electrode, or if other non-glucose reaction rate limiting phenomena occur (e.g., temperature or pH), the counter electrode can be driven in its electrochemical search for electrons all the way to ground or 0.0V. However, regardless of the voltage in the counter electrode, the working and counter electrode currents must still maintain substantially equivalent currents. Therefore, the reference electrode 102 will drift upward creating new oxidizing and reducing potentials that maintain equal currents at the working and counter electrodes.

Because of the function of the reference electrode 102, including the drift that occurs during periods of signal artifacts (e.g., ischemia), the reference electrode can be monitored to determine the severity of the signal artifacts on the data stream. Particularly, a substantially direct relationship between the reference electrode drift and signal artifacts has been discovered. Using the information contained within the CV curve (FIGS. 10B and/or 10C), the measured glucose signal ($I_{SENSE}$) can be automatically scaled accordingly to replace these undesired transient effects on the data stream. It is noted that the circuit described with reference to FIG. 10A can be used to determine the CV curve on a regularly scheduled basis or as needed. To this end, the desired reference voltage and applied potential are made variable, and the reference voltage can be changed at a defined rate while measuring the signal strength from the working electrode, which allows for generation of a CV curve while a sensor is in vivo.

In alternative implementations of the reference drift replacement method, a variety of algorithms can therefore be implemented that replaces the signal artifacts based on the changes measured in the reference electrode. Linear algorithms, and the like, are suitable for interpreting the direct relationship between reference electrode drift and the non-glucose rate limiting signal noise such that appropriate conversion to signal noise compensation can be derived.

In other embodiments of Signal Artifacts Replacement, prediction algorithms, also referred to as projection algorithms, can be used to replace glucose data signals for data which does not exist because 1) it has been discarded, 2) it is missing due to signal transmission errors or the like, or 3) it represents a time period (e.g., future) for which a data stream has not yet been obtained based on historic and/or present data. Prediction/projection algorithms include any of the above described Signal Artifacts Replacement algorithms, and differ only in the fact that they are implemented to replace time points/periods during which no data is available (e.g., for the above-described reasons), rather than including that existing data, within the algorithmic computation.

In some embodiments, signal replacement/estimation algorithms are used to predict where the glucose signal should be, and if the actual data stream varies beyond a certain threshold of that projected value, then signal artifacts are detected. In alternative embodiments, other data processing can be applied alone, or in combination with the above-described methods, to replace data signals during system noise and/or signal artifacts.

Selective Application of Signal Replacement Algorithms

Figure 15:
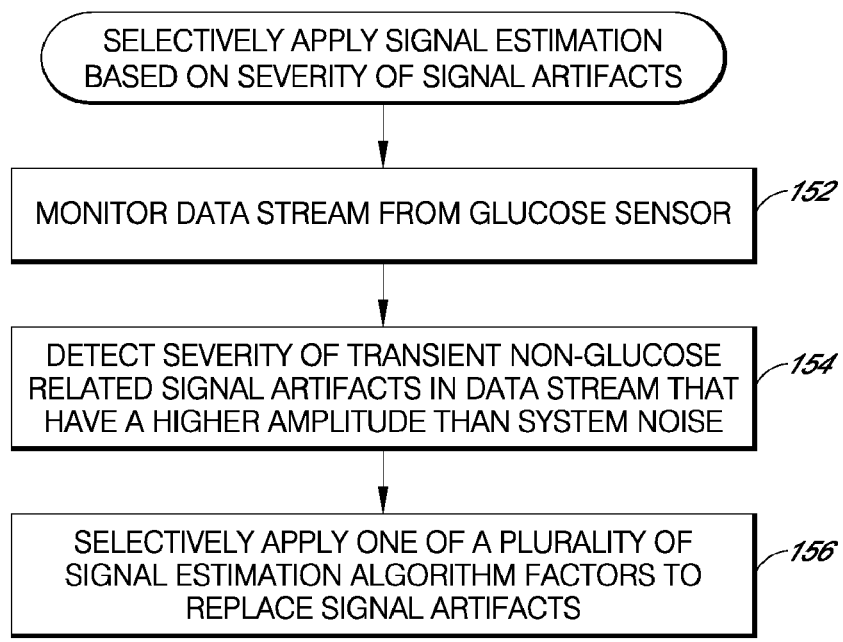
FIG. 15 is a flowchart that illustrates the process of selectively applying signal estimation based on the severity of signal artifacts on a data stream.

FIG. 15 is a flow chart that illustrates a process of selectively applying signal estimation in embodiments.

At block 152, a sensor data receiving module, also referred to as the sensor data module, receives sensor data (e.g., a data stream), including one or more time-spaced sensor data points, such as described in more detail with reference to block 82 in FIG. 8.

At block 154, a signal artifacts detection module, also referred to as the signal artifacts detector 154, is programmed to detect transient non-glucose related signal artifacts in the data stream that have a higher amplitude than system noise, such as described in more detail with reference to block 84 in FIG. 8. However, the signal artifacts detector of this embodiment can additionally detect a severity of signal artifacts. In some embodiments, the signal artifacts detector has one or more predetermined thresholds for the severity of the signal artifacts (e.g., low, medium, and high). In some embodiments, the signal artifacts detector numerically represents the severity of signal artifacts based on a calculation for example, which representation can be used to apply to the signal estimation algorithm factors, such as described in more detail with reference to block 156.

In one exemplary embodiment, the signal artifacts detection module evaluates the amplitude and/or frequency of the transient non-glucose related signal artifacts, which amplitude and/or frequency can be used to define the severity in terms of a threshold (e.g., high or low) or a numeric representation (e.g., a value from 1 to 10). In another exemplary embodiment, the signal artifacts detection module evaluates a duration of the transient non-glucose related signal artifacts, such that as the duration increases, a severity can be defined in terms of a threshold (e.g., short or long) or a numeric representation (e.g., 10, 20, 30, 40, 50, or 60 minutes). In another exemplary embodiment, the signal artifacts detection module evaluates the frequency content from a Fourier Transform and defines severity in terms of a threshold (e.g., above or below 30 cycles per hour) or a numeric representation (e.g., 50 cycles per hour). All of the signal artifacts detection methods described herein can be implemented to include determining a severity of the signal artifacts, threshold, and/or numerical representations.

At block 156, the signal artifacts replacement module, also referred to as the signal estimation module, selectively applies one of a plurality of signal estimation algorithm factors in response to the severity of said signal artifacts.

In one embodiment, signal artifacts replacement is normally turned off, except during detected signal artifacts. In another embodiment, a first signal estimation algorithm (e.g., linear regression, FIR filter etc.) is turned on all the time, and a second signal estimation algorithm optimized for signal artifacts (e.g., IIR filter, Cone of Possibility Replacement Method, etc.) is turned on only during positive detection of signal artifacts.

In another embodiment, the signal replacement module comprises programming to selectively switch on and off a plurality of distinct signal estimation algorithms based on the severity of the detected signal artifacts. For example, the severity of the signal artifacts can be defined as high and low. In such an example, a first filter (e.g., trimmed regression, linear regression, FIR, Reference Electrode Method, etc.) can be applied during low signal artifacts and a second filter (e.g., IIR, Cone of Possibility Method, etc.) can be applied during high signal artifacts. It is noted that all of the above signal replacement algorithms can be selectively applied in this manner based on the severity of the detected signal artifacts.

Figure 16:
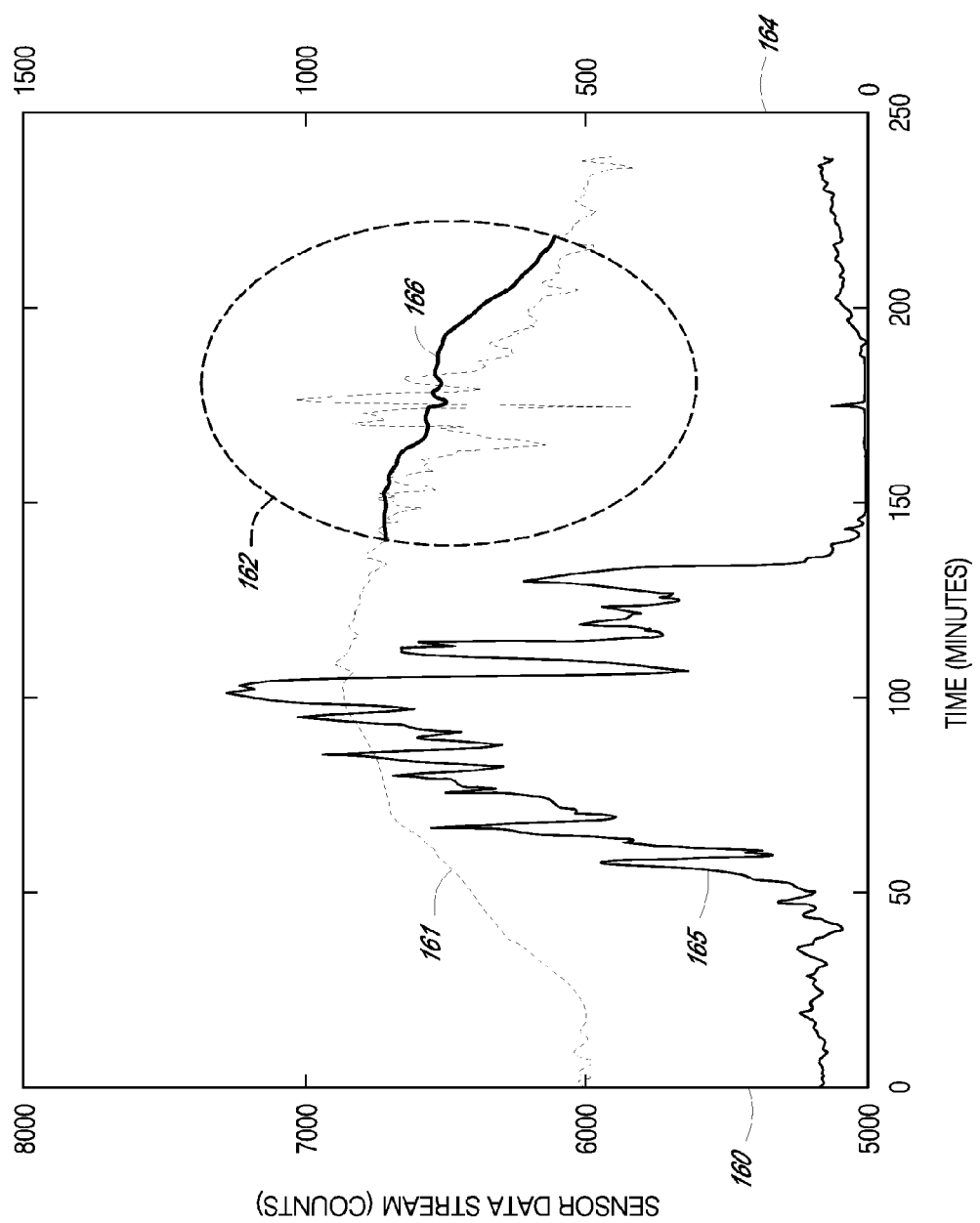
FIG. 16 is a graph that illustrates selectively applying a signal estimation algorithm responsive to positive detection of signal artifacts on the raw data stream.

FIG. 16 is a graph that illustrates a embodiment wherein the signal replacement module comprises programming to selectively switch on and off a signal artifacts replacement algorithm responsive to detection of signal artifacts. The x-axis represents time in minutes; the first y-axis 160 represents sensor data output in counts. A raw data signal 161, which is illustrated as a dotted line, shows a data stream wherein some system noise can be detected; however signal artifacts 162 can be particularly seen in a portion thereof. The second y-axis 164 represents counter-electrode voltage in counts; counter electrode voltage data 165 is illustrated as a solid line. It is noted that a counter voltage drop to approximately zero in this example, which is one of numerous methods provided for detecting signal artifacts, detects signal artifacts 162. Accordingly, when the system detects the signal artifacts 162, an IIR-filter is selectively switched on in order to replace the signal artifact with an IIR-estimated glucose signal 166, which is illustrated as a heavy solid line. The IIR filter is switched off upon detection of negligible signal artifacts (e.g., counter electrode voltage increasing from about zero in this embodiment).

Figure 17:
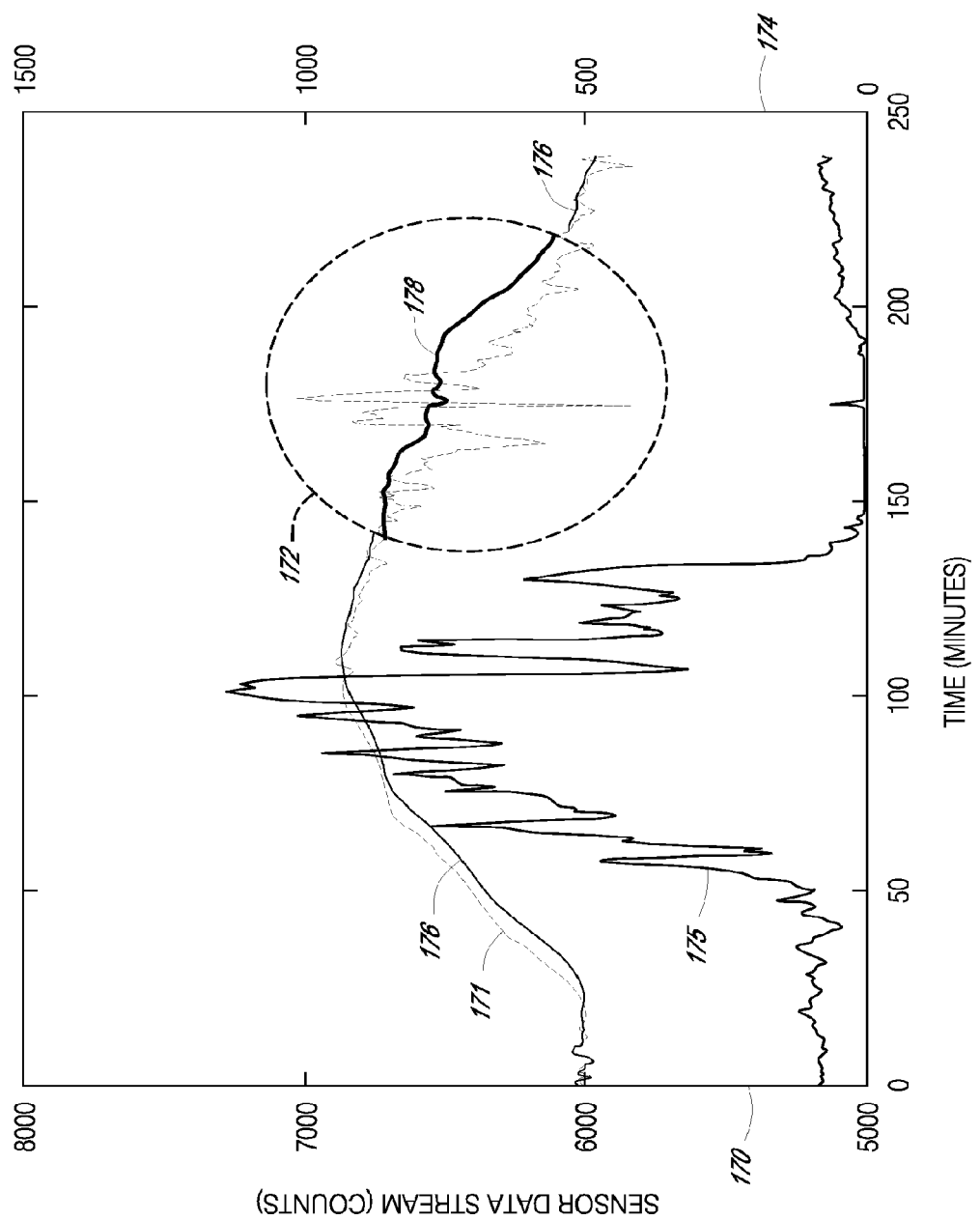
FIG. 17 is a graph that illustrates selectively applying a plurality of signal estimation algorithm factors responsive to a severity of signal artifacts on the raw data stream.

FIG. 17 is a graph that illustrates a embodiment wherein the signal artifacts replacement module comprises programming to selectively apply different signal artifacts replacement algorithms responsive to detection of signal artifacts. The x-axis represents time in minutes; the first y-axis 170 represents sensor data output in counts. A raw data signal 171, which is illustrated as a dotted line, shows a data stream wherein some system noise can be detected; however signal artifacts 172 can be particularly seen in a portion thereof. The second y-axis 174 represents counter-electrode voltage in counts; counter electrode voltage data 175 is illustrated as a solid line. It is noted that a counter voltage drop to approximately zero in this example, which is one of numerous methods provided for detecting signal artifacts, detects signal artifacts 172.

In this embodiment, an FIR filter is applied to the data stream during detection of negligible or no signal artifacts (e.g., during no noise to system noise in the data stream). Accordingly, normal signal noise (e.g., system noise) can be filtered to replace the data stream with an FIR-filtered data signal 176, which is illustrated by a slightly heavy solid line. However, upon positive detection of signal artifacts (e.g., detected by approximately zero counter electrode voltage in this embodiment), the FIR filter is switched off and an IIR-filter is switched on in order to replace the signal artifacts with an IIR-filtered glucose signal 178, which is illustrated as a heavy solid line. The IIR filter is subsequently switched off and the FIR filter is switched back on upon detection of negligible signal artifacts (e.g., counter electrode voltage increasing from about zero in this embodiment).

In another embodiment, the signal replacement module comprises programming to selectively apply different parameters to a single signal artifacts replacement algorithm (e.g., IIR, Cone of Possibility Replacement Method, etc.). As an example, the parameters of an algorithm can be switched according to signal artifacts detection; in such an example, an IIR filter with a 30-minute cycle length can be used during times of no noise or system noise and a 60-minute cycle length can be used during signal artifacts. As another example, the severity of the signal artifacts can be defined as short and long; in such an example, an IIR filter with a 30-minute cycle length can be used during the short signal artifacts and a 60-minute cycle length can be used during long signal artifacts. As yet another example, the severity of the signal artifacts can be defined by a numerical representation; in such an example, the numerical representation can be used to calculate the parameters of the signal replacement algorithm (e.g., IIR, Cone of Possibility Replacement Method, and Reference Drift Method).

The above description provides several methods and materials of the invention. This invention is susceptible to modifications in the methods and materials, as well as alterations in the fabrication methods and equipment. Such modifications will become apparent to those skilled in the art from a consideration of this application or practice of the invention provided herein. Consequently, it is not intended that this invention be limited to the specific embodiments provided herein, but that it cover all modifications and alternatives coming within the true scope and spirit of the invention as embodied in the attached claims. All patents, applications, and other references cited herein are hereby incorporated by reference in their entirety.

What is claimed is:

1. A system for processing a data stream obtained from a glucose sensor, the system comprising:
a signal processing module configured to monitor a data stream from a continuous glucose sensor over a period of time;
a detection module configured to determine a severity of signal artifacts in the data stream based on an amplitude and a duration of the signal artifacts;
a signal estimation module configured to selectively apply one or more coefficients or parameters to a signal estimation algorithm based on the severity of the signal artifacts and to apply the signal estimation algorithm to the data stream to generate an estimated signal.

2. The system of claim 1, wherein the signal estimation algorithm comprises a recursive filter.

3. The system of claim 2, wherein the signal estimation algorithm comprises an infinite impulse response filter.

4. The system of claim 1, wherein the signal estimation algorithm comprises a non-recursive filter.

5. The system of claim 4, wherein the signal estimation algorithm comprises an finite impulse response filter.

6. The system of claim 1, wherein the severity of signal artifacts comprise a numeric value.

7. The system of claim 6, wherein signal estimation module is configured to calculate the one or more coefficients or parameters from the numeric value.

8. The system of claim 1, further comprising an output module configured to transmit or display a representation of the estimated signal.

9. A method for processing a data stream obtained from a glucose sensor, the method comprising:
monitoring a data stream from a continuous glucose sensor over a period of time;
determining, using processing electronics, a severity of signal artifacts in the data stream based on an amplitude and a duration of the signal artifacts;
selectively applying one or more coefficients or parameters to a signal estimation algorithm based on the severity of the signal artifacts; and
applying the signal estimation algorithm to the data stream to generate an estimated signal.

10. The method of claim 9, wherein the signal estimation algorithm comprises a recursive filter.

11. The method of claim 10, wherein the signal estimation algorithm comprises an infinite impulse response filter.

12. The method of claim 10, wherein the signal estimation algorithm comprises an finite impulse response filter.

13. The method of claim 9, wherein the signal estimation algorithm comprises a non-recursive filter.

14. The method of claim 9, wherein the severity of signal artifacts comprise a numeric value.

15. The method of claim 14, wherein selectively applying comprises calculating the one or more coefficients or parameters from the numeric value.

16. The method of claim 9, further comprising transmitting or displaying a representation of the estimated signal.

* * * * *

UNITED STATES PATENT AND TRADEMARK OFFICE
CERTIFICATE OF CORRECTION

PATENT NO. : 8,491,474 B2
APPLICATION NO. : 13/015208
DATED : July 23, 2013
INVENTOR(S) : Goode, Jr. et al.

It is certified that error appears in the above-identified patent and that said Letters Patent is hereby corrected as shown below:

On the Title Page

In column 2 (page 6 item 56) at line 18, Under Other Publications, change "Filder" to --Filter--.

In column 1 (page 7 item 56) at line 50, Under Other Publications, change "hypoglycaemic" to --hypoglycemic--.

In column 2 (page 7 item 56) at line 3, Under Other Publications, change "Thechnol." to --Technol.--.

In column 2 (page 7 item 56) at line 8, Under Other Publications, change "Senso" to --Sensor--.

In column 2 (page 7 item 56) at line 26, Under Other Publications, change "543-48." to --S43-48.--.

In column 1 (page 8 item 56) at line 1, Under Other Publications, change "basedon" to --based--.

In column 1 (page 8 item 56) at line 28, Under Other Publications, change "impintable," to --implantable,--.

In column 1 (page 8 item 56) at line 33, Under Other Publications, change "reliablity" to --reliability--.

In column 1 (page 8 item 56) at line 47, Under Other Publications, change "Enzymlology," to --Enzymology,--.

In column 1 (page 8 item 56) at line 58, Under Other Publications, change "systme" to --system--.

In column 1 (page 8 item 56) at line 64, Under Other Publications, change "artifical" to --artificial--.

Signed and Sealed this
Fifteenth Day of April, 2014

Michelle K. Lee
*Deputy Director of the United States Patent and Trademark Office*

In column 2 (page 8 item 56) at line 15, Under Other Publications, change "your and your" to --you and your--.

In column 2 (page 8 item 56) at line 28, Under Other Publications, change "dynamcs" to --dynamics--.

In column 2 (page 8 item 56) at line 31, Under Other Publications, change "glocuse" to --glucose--.

In column 2 (page 8 item 56) at line 32, Under Other Publications, change "Diabetese" to --Diabetes--.

In column 2 (page 8 item 56) at line 45, Under Other Publications, change "Hypoglycaemia" to --Hypoglycemia--.

In column 2 (page 8 item 56) at line 61, Under Other Publications, change "Thechnol." to --Technol.--.

In column 2 (page 8 item 56) at line 66, Under Other Publications, change "Diabetese" to --Diabetes--.

In column 1 (page 9 item 56) at line 15, Under Other Publications, change "inactiviation" to --inactivation--.

In column 1 (page 9 item 56) at line 24, Under Other Publications, change "519-26." to --S19-26.--.

In column 1 (page 9 item 56) at line 29, Under Other Publications, change "patents" to --patients--.

In column 2 (page 9 item 56) at line 10, Under Other Publications, change "Aniodic" to --Anodic--.

In column 2 (page 9 item 56) at line 34, Under Other Publications, change "biotelemeter" to --biotelemetry--.

In column 1 (page 10 item 56) at line 21, Under Other Publications, change "activitiy," to --activity,--.

In column 1 (page 10 item 56) at line 42, Under Other Publications, change "Biosensors& Beioelectronics," to --Biosensors & Bioelectronics,--.

In column 1 (page 10 item 56) at line 43, Under Other Publications, change "glocuse" to --glucose--.

In column 1 (page 10 item 56) at line 60, Under Other Publications, change "valication" to --validation--.

In column 1 (page 10 item 56) at line 61, Under Other Publications, change "iunsulin interaaction in tyhpe 1" to --insulin interaction in type 1--.

CERTIFICATE OF CORRECTION (continued)
U.S. Pat. No. 8,491,474 B2

In column 2 (page 10 item 56) at line 34, Under Other Publications, change "artifical" to --artificial--.

In column 2 (page 10 item 56) at line 51, Under Other Publications, change "amperometeric" to --amperometric--.

In column 2 (page 10 item 56) at line 58, Under Other Publications, change "Thechnol." to --Technol.--.

In column 1 (page 11 item 56) at line 35, Under Other Publications, change "termistor" to --thermistor--.

In column 1 (page 11 item 56) at line 36, Under Other Publications, change "metobolites," to --metabolites,--.

In column 1 (page 11 item 56) at line 38, Under Other Publications, change "cholesteral and cholesteral" to --cholesterol and cholesterol--.

In column 1 (page 11 item 56) at line 45, Under Other Publications, change "Apllied" to --Applied--.

In column 1 (page 12 item 56) at line 19, Under Other Publications, change "assitance" to --assistance--.

In column 1 (page 12 item 56) at line 20, Under Other Publications, change "Thechnol." to --Technol.--.

In column 1 (page 12 item 56) at line 31, Under Other Publications, change "Membran," to --Membrane,--.

In column 1 (page 12 item 56) at line 54, Under Other Publications, change "Aced" to --Acad--.

In column 2 (page 12 item 56) at line 1, Under Other Publications, change "pancrease" to --pancreas--.

In column 2 (page 12 item 56) at line 22, Under Other Publications, change "Thechnol." to --Technol.--.

In column 2 (page 12 item 56) at line 57, Under Other Publications, change "Membrance" to --Membrane--.

In column 2 (page 12 item 56) at line 65, Under Other Publications, change "cholesteral" to --cholesterol--.

In column 1 (page 13 item 56) at line 19, Under Other Publications, change "Deabetes" to --Diabetes--.

In column 1 (page 13 item 56) at line 52, Under Other Publications, change "Tranducers" to --Transducers--.

CERTIFICATE OF CORRECTION (continued)
U.S. Pat. No. 8,491,474 B2

In column 1 (page 14 item 56) at line 44, Under Other Publications, change "n." to --in--.

In column 2 (page 14 item 56) at line 39, Under Other Publications, change "http://www.merriam-webstercom/dictionary/nominal" to --http://www.merriam-webster.com/dictionary/nominal--.

In the Specification

In column 7 at line 28, change "to for" to --for--.

In column 14 at line 19, change "O2" to --$O_2$--.

In column 14 at line 20, change "H2O2," to --$H_2O_2$,--.

In column 27 at line 26, change "there" to --their--.

In column 32 at line 60, change "an/or" to --and/or--.

In column 37 at line 8, change "Additionally It" to --Additionally, it--.

In column 37 at line 38, change "Additionally It" to --Additionally, it--.

In column 38 at line 27, change "It" to --it--.

In column 38 at line 67, change "he" to --the--.